(12) United States Patent
Vaux et al.

(10) Patent No.: US 9,822,078 B2
(45) Date of Patent: Nov. 21, 2017

(54) QUINOLINE COMPOUNDS

(71) Applicant: Oxford University Innovation Limited, Oxford (GB)

(72) Inventors: David Vaux, Oxford (GB); Letitia Jean, Oxford (GB); Stephen Davies, Oxford (GB); Angela Russell, Oxford (GB); Graham Wynne, Oxford (GB); Carole Bataille, Oxford (GB); Méabh Brennan, London (GB)

(73) Assignee: Oxford University Innovation Limited, Oxford (GB)

( * ) Notice: Subject to any disclaimer, the term of this patent is extended or adjusted under 35 U.S.C. 154(b) by 0 days.

(21) Appl. No.: 15/121,973

(22) PCT Filed: Feb. 27, 2015

(86) PCT No.: PCT/GB2015/050588
§ 371 (c)(1),
(2) Date: Aug. 26, 2016

(87) PCT Pub. No.: WO2015/128674
PCT Pub. Date: Sep. 3, 2015

(65) Prior Publication Data
US 2017/0008849 A1  Jan. 12, 2017

(30) Foreign Application Priority Data

Feb. 28, 2014  (GB) .................................. 1403595.0

(51) Int. Cl.
| C07D 215/00 | (2006.01) |
| C07D 215/26 | (2006.01) |
| C07D 413/14 | (2006.01) |
| C07D 401/06 | (2006.01) |
| A61K 31/47 | (2006.01) |
| A61K 31/4709 | (2006.01) |
| A61K 31/5377 | (2006.01) |
| C07D 405/06 | (2006.01) |

(52) U.S. Cl.
CPC ............ *C07D 215/26* (2013.01); *A61K 31/47* (2013.01); *A61K 31/4709* (2013.01); *A61K 31/5377* (2013.01); *C07D 401/06* (2013.01); *C07D 405/06* (2013.01); *C07D 413/14* (2013.01)

(58) Field of Classification Search
CPC .................................................. C07D 215/00
USPC ....................................................... 546/152
See application file for complete search history.

(56) References Cited

U.S. PATENT DOCUMENTS

| 4,769,461 A | 9/1988 | Musser et al. |
| 2009/0163545 A1* | 6/2009 | Goldfarb ............. A61K 31/122 514/312 |
| 2011/0224242 A1 | 9/2011 | Giethlen et al. |

FOREIGN PATENT DOCUMENTS

| EP | 2149557 A1 | 2/2010 |
| WO | WO-2004/007461 A1 | 1/2004 |
| WO | WO-2006/129134 A1 | 12/2006 |
| WO | WO-2014/179785 A1 | 11/2014 |

OTHER PUBLICATIONS

Chang, Pei-Teh, et al.; "An Improved Screening Model to Identify Inhibitors Targeting Zinc-Enhanced Amyloid Aggregation," Analytical Chemistry; 81(16): 6944-6951 (Aug. 15, 2009).
Cieslik, Wioleta, et al.; "Contribution to investigation of antimicrobial activity of styrylquinolines," Biorganic & Medicinal Chemistry; 20(24): 6960-6968 (2012).
Noblin, Devin, J., et al.; "A HaloTag-Based Small Molecule Microarray Screening Methodology with Increased Sensitivity and Multiplex Capabilities," 7(12): 2055-2063 (2012).
Zouhiri, Fatima, et al. "Structure-Activity Relationships and Binding Mode of Styrylquinolines as Potent Inhibitors of HIV-1 Integrase and Replication of HIV-1 in Cell Culture," 43(8): 1533-1540 (2000).
XP002737812, Database Registry, Chemical Abstracts Service, Database accession No. 314045-71-1; RN=314-45-71-1 (Jan. 16, 2001).
International Search Report and Written Opinion for PCT/GB2015/050588 dated Apr. 17, 2015.
UK Search Report for GB1403595.0 dated Sep. 23, 2014.

* cited by examiner

Primary Examiner — Niloofar Rahmani
(74) Attorney, Agent, or Firm — Foley Hoag LLP

(57) ABSTRACT

The present invention relates to quinoline compounds as defined by Formula I below. Such quinoline compounds have been shown to inhibit the formation of amyloid deposits (e.g., amyloid oligomers, fibrils or plaques). Consequently, these compounds are suitable for treating a range of diseases and disorders in which amyloid deposits are implicated, such as type-2 diabetes and Alzheimer's disease.

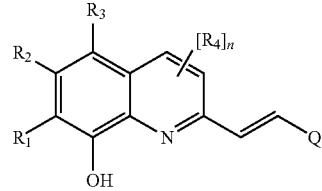

Formula I

13 Claims, 44 Drawing Sheets

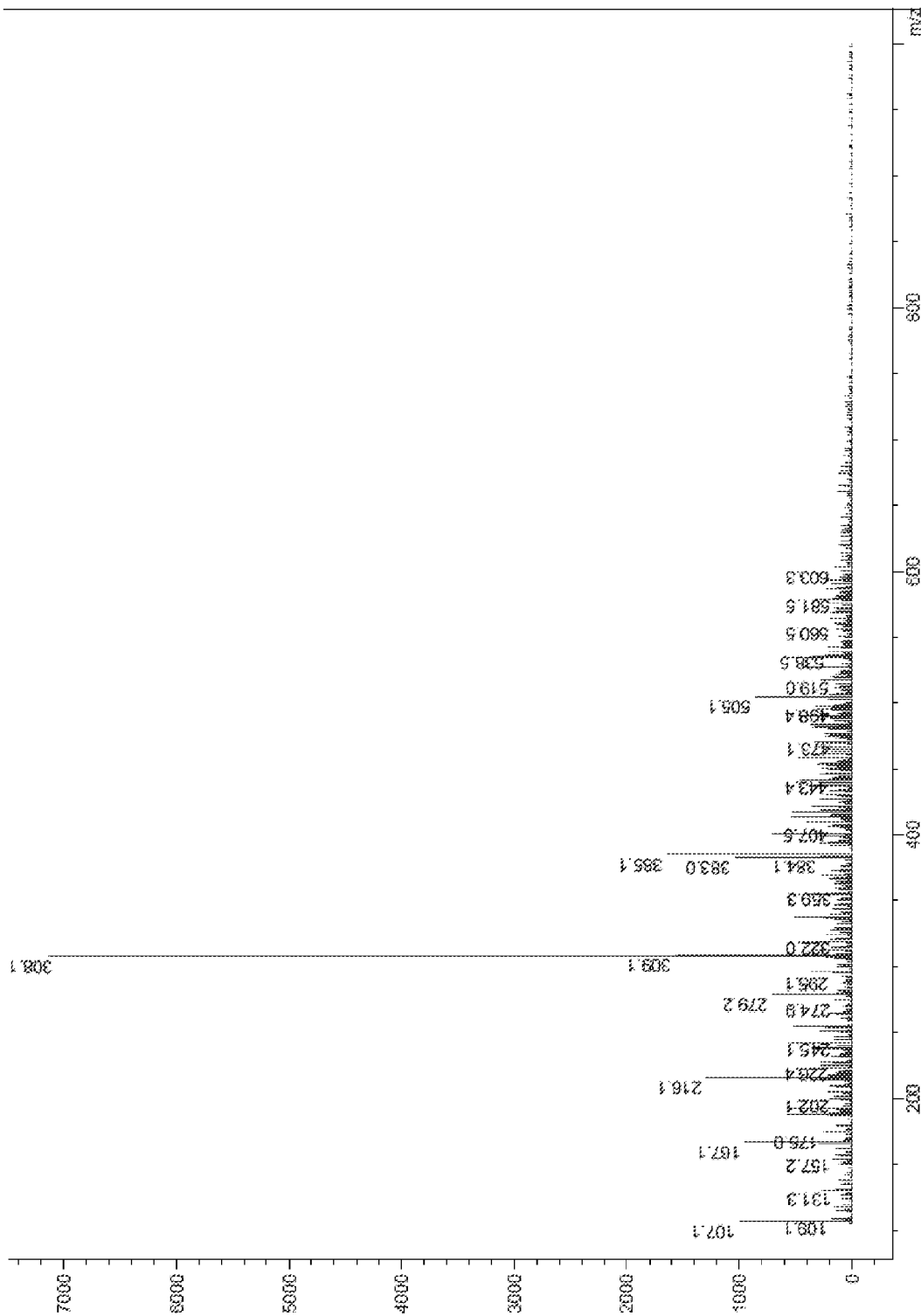

QUINOLINE COMPOUNDS

RELATED APPLICATIONS

This application is a §371 national stage application based on Patent Cooperation Treaty Application serial number PCT/GB2015/050588, filed Feb. 27, 2015, which claims the benefit of priority to GB 1403595.0, filed Feb. 28, 2014. The entire contents of each of these applications are hereby incorporated by reference.

INTRODUCTION

The present invention relates to certain quinoline compounds. More specifically, the present invention relates to certain quinoline compounds that inhibit the formation of amyloid deposits (e.g. amyloid plaques or fibrils). Consequently, these compounds are suitably for treating diseases and disorders associated with the formation of amyloid deposits, such as, for example, type-2 diabetes and/or Alzheimer's disease. The present invention also relates to processes for the preparation of these compounds, to pharmaceutical compositions comprising them, and to their use in the treatment of relevant disorders, such as, for example, type-2 diabetes and/or Alzheimer's disease.

BACKGROUND

Amyloids are insoluble fibrous protein aggregates (also known as "amyloid fibrils" or "amyloid plaques") which form in vivo, typically at hydrophobic-hydrophilic interfaces (HHIs), when naturally-occurring proteins and polypeptides misfold and inadvertently interact with one another and/or with other cell components to form aggregates. Amyloid plaques/fibrils, and consequencial amyloidosis, are believed to be responsible, at least in part, for numerous human diseases, including but not limited to Alzheimer's disease and type-2 diabetes.

Amyloid-beta (Aβ) peptides are the principle component of amyloid plaques found in the brains of Alzheimer's patients, and are thought to result from an amyloid precursor protein (APP) which when cut by particular enzymes yield Aβ peptides which misfold and aggregate to yield first oligomers and fibrils and ultimately amyloid plaques, amongst which sequence of conformers are those that are toxic to nerve cells.

Amylin (or Islet Amyloid Polypeptide—IAPP) is the principle component of amyloid deposits commonly found in pancreatic islets of type-2 diabetes patients. Such deposits of IAPP are thought to be typically initiated by unprocessed proIAPP seeds. It is thought that amylin, much like the related Aβ peptides associated with Alzheimer's disease, can induce apoptotic or excitotoxic cell-death in insulin-producing beta cells. It is thought that this effect may be relevant to the development of type 2 diabetes (Lorenzo A, Razzaboni B, Weir G C, Yankner B A (April 1994). "Pancreatic islet cell toxicity of amylin associated with type-2 diabetes mellitus". *Nature* 368 (6473): 756-60).

Most proteins contain hydrophobic and hydrophilic domains and their adsorption to hydrophobic-hydrophilic interfaces (HHIs) is due to this amphiphilic character, conferring upon them surfactant properties. Protein adsorption, a complex process dependent on both protein and interface characteristics, is governed by bulk diffusion and results in interface adsorption. Once the interface becomes crowded, the adsorbed molecules will begin to align themselves at the interface (Wu et al 1993; Graham et al 1979; Ariola et al 2006). This conformation change may lead to intermolecular attractions between molecules, which in turn may result in the formation of interfacial multi-layers (Schmidt et al 1990). Protein adsorption also has significant implications in the activity of proteins toward membranes; amphiphilicity of proteins or peptides allow them to bind to membrane interfaces.

Amyloid peptides are amphiphilic and surface active (Lopes et al 2007; Cottingham M et al 2004; Soreghan et al 1994). This amphiphilicity has been exploited by amyloid precursor species to bind to membranes and to use this interaction to facilitate assembly into amyloid fibrils (Knight and Miranker 2004; Knight et al 2006; Lopes et al 2007; Terzi et al 1997). The eventual appearance of macroscopic amyloid deposits is a hallmark of protein misfolding diseases such as type II diabetes mellitus and Alzheimer's disease. During fibrillisation, amyloid peptides undergo a conformational change to form extended β-strands, facilitated by interaction with an HHI, whether membrane or AWI (air-water interface). This is due to a concentration effect of amphiphilic amyloids at the interface, which in turn alters the thermodynamic equilibrium and promotes peptide chains alignment (Lopes et al 2007; Terzi et al 1997; Soreghan et al 1994; Jean et al 2010). Recent attention has focused on determining the effects that lipids have on amyloid fibrillogenesis; in the presence of an AWI, anionic lipids were shown to enhance amyloid nucleation whereas zwitterionic lipids had no effect (Knight and Miranker 2004; Knight et al 2006; Chi et al 2008). However, this enhancing effect of anionic lipids on amyloidogenesis was demonstrated to be at its greatest in a context more closely mirroring in vivo conditions (the absence of an AWI; see Jean et al 2010). Thus, to understand fully fibrillisation enhancement by phospholipid bilayers, the biophysical consequences of amyloid surfactant activity and the potential importance of a competing AWI need to be taken into account.

Many proteins that adsorb at interfaces are able to form multi-layered proteinaceous networks, which can be stabilised by interfacial gel formation. The interfacial gel layer itself can be stabilised by numerous non-covalent interactions to form a meshwork of aggregates (e.g. fibres), typical of assembled amyloid polypeptides. To date gel formation has only been demonstrated for non-pathological amyloidogenic polypeptides (e.g. *Escherichia coli curli*, class II hydrophobins, b-lactoglobulin, spider silk) and for fragments of pathological amyloidogenic polypeptides (Wu et al 2012, Cox et al 2007, Bolisetty et al 2012, Yang et al 2012, Rijkers et al 2002, Krysmann et al 2008, Lepere et al 2007, Lakshmanan et al 2013, Manno M et al 2010). We have recently shown by direct rheological measurement that hydrated gel formation by pathological amyloid precursors including Aβ and islet amyloid precursor polypeptide (IAPP) does indeed occur at HHIs.

The pathologically relevant mechanisms of amyloid cytotoxicity are uncertain, although recent attention has focused on the concentration of amyloid peptides at membrane HHIs, which can cause disruption by a variety of mechanisms such as pore formation and membrane thinning (Kayed et al 2004; Quist et al 2005; Demuro et al 2005; Butterfield and Lashuel 2010). However, it seems probable that gel formation by amyloid species on the surface of cellular membranes could have important additional consequences for membrane integrity and cellular functions.

It is an object of the present invention to provide compounds that are capable of inhibiting the formation of amyloid deposits by acting at an early stage such that the production of the cytotoxic species, whether oligomer or fibril, is inhibited. Such compounds are potentially useful agents for the treatment of diseases such as Alzheimer's disease and/or type-2 diabetes.

SUMMARY OF THE INVENTION

According to a first aspect of the present invention, there is provided a compound, or a pharmaceutically acceptable salt, hydrate or solvate thereof, as defined herein.

According to a further aspect of the present invention, there is provided a pharmaceutical composition comprising a compound as defined herein, or a pharmaceutically acceptable salt, hydrate or solvate thereof, in admixture with a pharmaceutically acceptable diluent or carrier.

According to a further aspect of the present invention, there is provided a method of inhibiting the formation of amyloid deposits (in vivo or in vitro), said method comprising contacting a tissue or cell with an effective amount of a compound or a pharmaceutically acceptable salt, hydrate or solvate thereof as defined herein.

According to a further aspect of the present invention, there is provided a method of inhibiting amyloidosis (in vivo or in vitro), said method comprising contacting a tissue or cell with an effective amount of a compound or a pharmaceutically acceptable salt, hydrate or solvate thereof as defined herein.

According to a further aspect of the present invention, there is provided a method of inhibiting the formation of amyloid-beta (Aβ) peptide cytotoxic aggregates (in vivo or in vitro), said method comprising contacting a tissue or cell with an effective amount of a compound or a pharmaceutically acceptable salt, hydrate or solvate thereof as defined herein.

According to a further aspect of the present invention, there is provided a method of inhibiting the formation of Islet Amyloid Polypeptide (IAPP) cytotoxic aggregates (in vivo or in vitro), said method comprising contacting a tissue or cell with an effective amount of a compound or a pharmaceutically acceptable salt, hydrate or solvate thereof as defined herein.

According to a further aspect of the present invention, there is provided a method of inhibiting apoptotic or excitotoxic cell-death, in vitro or in vivo, said method comprising contacting a cell with an effective amount of a compound or a pharmaceutically acceptable salt, hydrate or solvate thereof as defined herein, or a pharmaceutical composition as defined herein.

According to a further aspect of the present invention, there is provided a method of treating a disease or disorder in which amyloid deposits or amyloidosis is implicated in a patient in need of such treatment, said method comprising administering to said patient a therapeutically effective amount of a compound or a pharmaceutically acceptable salt, hydrate or solvate thereof as defined herein, or a pharmaceutical composition as defined herein.

According to a further aspect of the present invention, there is provided a method of treating Alzheimer's disease, or the symptoms thereof, in a patient in need of such treatment, said method comprising administering to said patient a therapeutically effective amount of a compound or a pharmaceutically acceptable salt, hydrate or solvate thereof as defined herein, or a pharmaceutical composition as defined herein.

According to a further aspect of the present invention, there is provided a method of treating type-2 diabetes, or the symptoms thereof, in a patient in need of such treatment, said method comprising administering to said patient a therapeutically effective amount of a compound or a pharmaceutically acceptable salt, hydrate or solvate thereof as defined herein, or a pharmaceutical composition as defined herein.

According to a further aspect of the present invention, there is provided a compound, or a pharmaceutically acceptable salt, hydrate or solvate thereof, or a pharmaceutical composition as defined herein for use in therapy.

According to a further aspect of the present invention, there is provided a compound or a pharmaceutically acceptable salt, hydrate or solvate thereof as defined herein, or a pharmaceutical composition as defined herein, for use in inhibiting the formation of amyloid deposits (in vivo or in vitro).

According to a further aspect of the present invention, there is provided a compound or a pharmaceutically acceptable salt, hydrate or solvate thereof as defined herein, or a pharmaceutical composition as defined herein, for use in inhibiting amyloidosis (in vivo or in vitro).

According to a further aspect of the present invention, there is provided a compound or a pharmaceutically acceptable salt, hydrate or solvate thereof as defined herein, or a pharmaceutical composition as defined herein, for use in inhibiting the formation of cytotoxic aggregates of amyloid-beta (Aβ) peptides (in vivo or in vitro).

According to a further aspect of the present invention, there is provided a compound or a pharmaceutically acceptable salt, hydrate or solvate thereof as defined herein, or a pharmaceutical composition as defined herein, for use in inhibiting the formation of cytotoxic aggregates of Islet Amyloid Polypeptide (IAPP) (in vivo or in vitro).

According to a further aspect of the present invention, there is provided a compound or a pharmaceutically acceptable salt, hydrate or solvate thereof as defined herein, or a pharmaceutical composition as defined herein, for use in inhibiting apoptotic or excitotoxic cell-death (in vivo or in vitro).

According to a further aspect of the present invention, there is provided a compound or a pharmaceutically acceptable salt, hydrate or solvate thereof as defined herein, or a pharmaceutical composition as defined herein, for use in treating a disease or disorder in which amyloid deposits or amyloidosis is implicated.

According to a further aspect of the present invention, there is provided a compound or a pharmaceutically acceptable salt, hydrate or solvate thereof as defined herein, or a pharmaceutical composition as defined herein, for use in treating Alzheimer's disease, or the symptoms thereof.

According to a further aspect of the present invention, there is provided a compound or a pharmaceutically acceptable salt, hydrate or solvate thereof as defined herein, or a pharmaceutical composition as defined herein, for use in treating type-2 diabetes, or the symptoms thereof.

According to a further aspect of the present invention, there is provided the use of a compound, or a pharmaceutically acceptable salt, hydrate or solvate thereof, as defined herein in the manufacture of a medicament for the treatment of a disease or disorder in which amyloid deposits or amyloidosis is implicated.

According to a further aspect of the present invention, there is provided the use of a compound, or a pharmaceutically acceptable salt, hydrate or solvate thereof, as defined herein in the manufacture of a medicament for the treatment of Alzheimer's disease, or the symptoms thereof.

According to a further aspect of the present invention, there is provided the use of a compound, or a pharmaceutically acceptable salt, hydrate or solvate thereof, as defined herein in the manufacture of a medicament for the treatment of type-2 diabetes, or the symptoms thereof.

According to a further aspect of the present invention, there is provided a process for preparing a compound, or a pharmaceutically acceptable salt, hydrate or solvate thereof, as defined herein.

According to a further aspect of the present invention, there is provided a compound, or a pharmaceutically acceptable salt, hydrate or solvate thereof, obtainable by, or obtained by, or directly obtained by a process of preparing a compound as defined herein.

According to a further aspect of the present invention, there are provided novel intermediates as defined herein which are suitable for use in any one of the synthetic methods set out herein.

Any features, including optional, suitable, and preferred features, described in relation to any particular aspect of the invention may also be features, including optional, suitable and preferred features, of any other aspect of the present invention.

BRIEF DESCRIPTION OF THE DRAWINGS

For a better understanding of the invention, and to show how embodiments of the same are put into effect, reference is now made, by way of example, to the following diagrammatic drawings, in which.

DETAILED DESCRIPTION OF THE INVENTION

Definitions

Figure 1A:
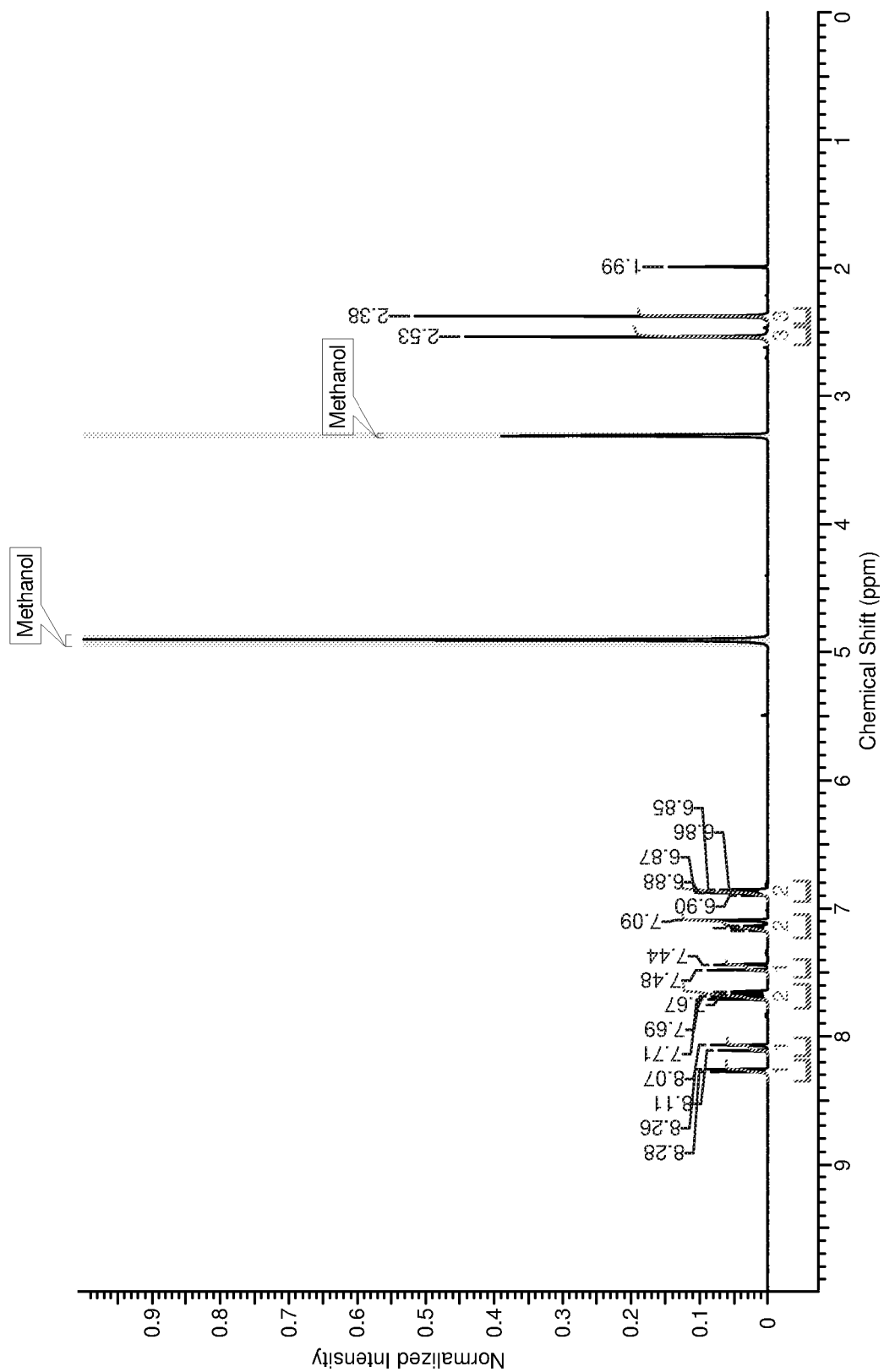
FIG. 1 shows the a) $^1$H NMR characterisation data and b) mass spectrometry characterisation data for compound 214.

Unless otherwise stated, the following terms used in the specification and claims have the following meanings set out below.

Herein, the term "amyloid deposit(s)" refers to amyloid oligomers, fibrils or plaques.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

The term "halo" or "halogeno" refers to fluoro, chloro, bromo and iodo.

The term "(m-nC)haloalkyl" or "(m-nC)haloalkoxy" respectively refers to halo-substituted "(m-nC)alkyl" or "(m-nC)alkoxy" moieties, wherein said "(m-nC)alkyl" or "(m-nC)alkoxy" moieties are substituted by one or more halo groups (e.g. mono, di, and tri-halo derivativs). For instance, (1-4C)haloalkyl may encompass trifluoromethyl, whereas (1-4C)haloalkoxy may encompass trifluoromethoxy. In some embodiments, the terms "(m-nC)haloalkyl" or "(m-nC)haloalkoxy" refer to mono-, di-, or tri-halo substituted derivatives of "(m-nC)alkyl" or "(m-nC) alkoxy" moieties.

The term "heterocyclyl", "heterocyclic" or "heterocycle" means a non-aromatic saturated or partially saturated monocyclic, fused, bridged, or spiro bicyclic heterocyclic ring system(s). The term heterocyclyl includes both monovalent species and divalent species. Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocycles contain from about 7 to about 17 ring atoms, suitably from 7 to 12 ring atoms. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

The term "optionally substituted" refers to either groups, structures, or molecules that are substituted and those that are not substituted. The term "wherein a/any CH, $CH_2$ or $CH_3$ group within a $R^1$ group is optionally substituted" suitably means that (any) one of the hydrogen radicals of the $R^1$ group is substituted by a relevant stipulated group.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

COMPOUNDS OF THE INVENTION

The present invention provides a compound of Formula I:

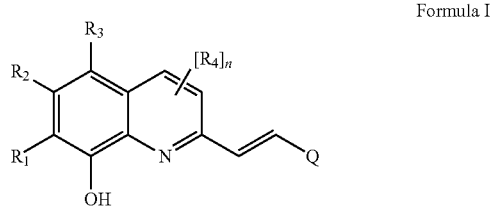

Formula I wherein:
$R_1$ is selected from halo, (1-3C)alkyl, (1-3C)haloalkyl, (1-3C)alkoxy, (1-3C)haloalkoxy;
$R_2$ is selected from hydrogen or fluoro;
$R_3$ is selected from halo, (1-3C)alkyl, (1-3C)haloalkyl, (1-3C)alkoxy, (1-3C)haloalkoxy;
$R_4$ is selected from halo, (1-3C)alkyl, (1-3C)haloalkyl;
n is 0, 1, or 2;

Q is a ring system selected from phenyl, 5- or 6-membered heteroaryl, or (5-7C)cycloalkyl, each of which is optionally fused to a 5- or 6-membered heterocyclyl (e.g. to form a methylenedioxy-substituted Q ring system) ring, and wherein the Q ring system isoptionally substituted by: one, two, or three $R_Q$ groups; wherein $R_Q$ is independently selected from halo, hydroxy, nitro, cyano, (1-4C)alkyl, (1-4C)haloalkyl, (1-4C)alkoxy, (1-4C)haloalkoxy, $NR_cR_c$, $C(O)R_c$, $C(O)OR_c$, $OC(O)R_c$, $C(O)N(R_d)R_c$, $N(R_c)C(O)R_d$, $S(O)_pR_c$ (where p is 0, 1 or 2), $SO_2N(R_c)R_d$, $N(R_c)SO_2R_d$, or a 4-, 5-, 6-membered heterocyclyl, wherein $R_c$ and $R_d$ are each independently selected from H or (1-4C)alkyl;

or a pharmaceutically acceptable salt, hydrate or solvate thereof;

with the proviso that when $R_1$ and $R_3$ are methyl, $R_2$ is H and n is 0, Q is not 2-aminophenyl.

Particular compounds of the invention include, for example, compounds of the formula I, or pharmaceutically acceptable salts and/or solvates thereof, wherein, unless otherwise stated, each of $R_1$, $R_2$, $R_3$, $R_4$, n, Q and any associated substituent groups has any of the meanings defined hereinbefore or in any of paragraphs (1) to (31) hereinafter:—

(1) $R_1$ is selected from (1-3C)alkyl, (1-3C)haloalkyl, (1-3C)alkoxy, (1-3C)haloalkoxy;
(2) $R_1$ is selected from (1-3C)alkyl, (1-3C)haloalkyl, (1-3C)alkoxy;
(3) $R_1$ is selected from (1-3C)alkyl, (1-3C)alkoxy;
(4) $R_1$ is (1-3C)alkyl;
(5) $R_1$ is selected from halo, methyl, halomethyl, methoxy, halomethoxy;
(6) $R_1$ is selected from methyl, halomethyl, methoxy, halomethoxy;
(7) $R_1$ is methyl;
(8) $R_2$ is hydrogen;
(9) $R_3$ is selected from (1-3C)alkyl, (1-3C)haloalkyl, (1-3C)alkoxy, (1-3C)haloalkoxy;
(10) $R_3$ is selected from halo, methyl, halomethyl, methoxy, halomethoxy;
(11) $R_3$ is selected from methyl, halomethyl, methoxy, halomethoxy;
(12) $R_3$ is (1-3C)alkyl;
(13) $R_3$ is methyl;
(14) $R_4$ is selected from halo, methyl, halomethyl;
(15) n is 0;
(16) Q is a ring system selected from phenyl, 5- or 6-membered heteroaryl, or (5-7C)cycloalkyl, each of which is optionally fused to a 5-membered heterocyclyl ring, and wherein the Q ring system is optionally substituted by: one, or two $R_Q$ groups; wherein $R_Q$ is independently selected from halo, hydroxy, nitro, cyano, (1-4C)alkyl, (1-4C)haloalkyl, (1-4C)alkoxy, (1-4C)haloalkoxy, $NR_cR_c$, $C(O)OR_c$, or a 6-membered heterocyclyl, wherein $R_c$ and $R_d$ are each H;
(17) Q is a ring system selected from phenyl, 5- or 6-membered heteroaryl, or (5-7C)cycloalkyl, each of which is optionally fused to a 5-membered heterocyclyl ring (e.g. to form a methylenedioxy-substituted ring system), and wherein the Q ring system is optionally substituted by: one, or two $R_Q$ groups; wherein $R_Q$ is independently selected from halo, hydroxy, nitro, cyano, (1-3C)alkyl, (1-3C)haloalkyl, (1-3C)alkoxy, (1-3C)haloalkoxy, $NR_cR_c$, $C(O)OR_c$, or a 6-membered heterocyclyl, wherein $R_c$ and $R_d$ are each H;

(18) Q is either:
(i) a ring system selected from the following:

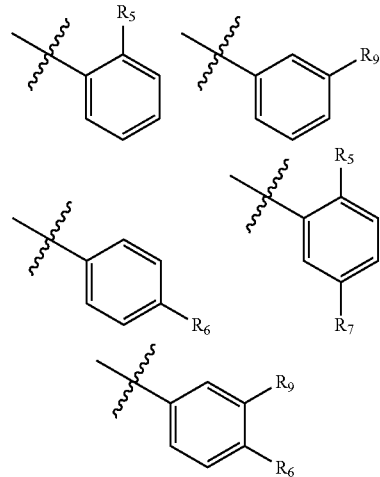

wherein, $R_5$, $R_6$, $R_7$ and $R_9$ are independently from halo, hydroxy, nitro, cyano, (1-2C)alkyl, trifluoromethyl, (1-2C)alkoxy, trifluoromethoxy, $NH_2$ or $C(O)OR_c$, wherein $R_c$ is H, and wherein, optionally, $R_6$ and $R_9$ may be linked to form a 5-membered methylenedioxy-substituted heterocyclyl ring;

(ii) or a 5- or 6-membered heteroaryl, or (5-7C)cycloalkyl, wherein said heteroaryl or cycloalkyl is optionally substituted by: one, or two $R_Q$ groups; wherein $R_Q$ is independently selected from halo, hydroxy, nitro, cyano, (1-3C)alkyl, trifluoromethyl, (1-3C)alkoxy, trifluoromethoxy, $NH_2$, $C(O)OR_c$, or a 6-membered heterocyclyl, wherein $R_c$ is H;

(19) Q is either:
(i) a ring system selected from the following:

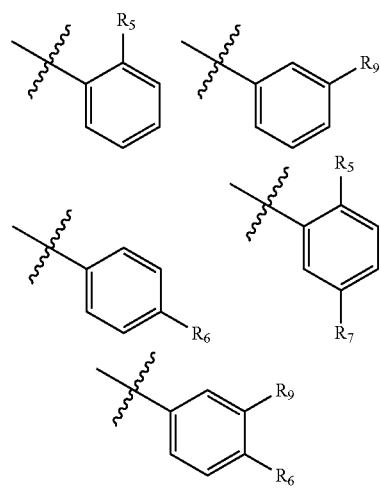

wherein, $R_5$ is selected from hydroxy, nitro, cyano or $NH_2$, $R_6$ is selected from hydroxyl, halo, (1-2C)alkoxy or trifluoromethoxy, $R_7$ is $C(O)OH$, and $R_9$ is selected from hydroxy, nitro, cyano or (1-2C)alkoxy, and wherein, optionally, $R_6$ and $R_9$ may be linked to form a 5-membered methylenedioxy-substituted heterocyclyl ring;

(ii) or a 5- or 6-membered heteroaryl, or (5-7C)cycloalkyl, wherein said heteroaryl or cycloalkyl is optionally substituted by: one, or two $R_Q$ groups; wherein $R_Q$ is independently selected from halo, hydroxy, nitro, cyano, (1-3C)alkyl, trifluoromethyl, (1-3C)alkoxy, trifluoromethoxy, $NH_2$, $C(O)OR_c$, or a 6-membered heterocyclyl, wherein $R_c$ is H;

(20) Q is an unsubstituted ring system selected from phenyl, 5- or 6-membered heteroaryl, or (5-7C)cycloalkyl;

(21) Q is a ring system selected from phenyl or 6-membered heteroaryl, each of which is optionally fused as defined hereinbefore in relation to Q, and wherein the Q ring system is optionally substituted as defined hereinbefore in relation to Q (for example as defined in any one of paragraphs (16) to (19) above);

(22) Q is a ring system selected from 5- or 6-membered heteroaryl or (5-7C)cycloalkyl, wherein the Q ring system is optionally substituted as defined hereinbefore in relation to Q (for example as defined in any one of paragraphs (16) to (19) above);

(23) Q is a ring system selected from 6-membered heteroaryl or cyclohexyl, wherein the Q ring system is optionally substituted as defined hereinbefore in relation to Q (for example as defined in any one of paragraphs (16) to (19) above);

(24) Q is a ring system selected from phenyl, furanyl, pyridyl, or cyclohexyl, each of which is optionally fused as defined hereinbefore in relation to Q, and wherein the Q ring system is optionally substituted as defined hereinbefore in relation to Q (for example as defined in any one of paragraphs (16) to (19) above);

(25) Q is a ring system selected from furanyl, pyridyl, or cyclohexyl, wherein the Q ring system is optionally substituted as defined hereinbefore in relation to Q (for example as defined in any one of paragraphs (14) to (17) above);

(26) Q is a ring system selected from phenyl or pyridyl, each of which is optionally fused as defined hereinbefore in relation to Q, and wherein the Q ring system is optionally substituted as defined hereinbefore in relation to Q (for example as defined in any one of paragraphs (16) to (19) above);

(27) Q is a pyridyl ring system, which is optionally fused as defined hereinbefore in relation to Q, and wherein the Q ring system is optionally substituted as defined hereinbefore in relation to Q (for example as defined in any one of paragraphs (16) to (19) above);

(28) Q is pyridyl ring system, wherein the Q ring system is optionally substituted with one or more substituents selected from halo, hydroxy, nitro, cyano, methyl, trifluoromethyl, (1-3C)alkoxy, trifluoromethoxy, $NH_2$, morpholino, or piperizino;

(29) Q is a 3-pyridyl ring system, which is optionally fused as defined hereinbefore in relation to Q, and wherein the Q ring system is optionally substituted as defined hereinbefore in relation to Q (for example as defined in any one of paragraphs (16) to (19) above);

(30) Q is a 3-pyridyl ring system, wherein the Q ring system is optionally substituted with one or more substituents selected from halo, hydroxy, nitro, cyano, methyl, trifluoromethyl, (1-3C)alkoxy, trifluoromethoxy, $NH_2$, morpholino, or piperizino;

(31) Q is an unsubstituted 3-pyridyl ring system.

Suitably, a heteroaryl or heterocyclyl group as defined herein is a monocyclic heteroaryl or heterocyclyl group comprising one, two or three heteroatoms selected from N, O or S.

In an embodiment of the compounds of formula I:
$R_1$ is as defined in any one of paragraphs (1) to (7) above;
$R_2$ is as defined in paragraph (8) above;
$R_3$ is as defined in any one of paragraph (9) to (13 above);
$R_4$ is as defined in paragraph (14) above;
n is 0 or 1;
Q is as defined in any one of paragraphs (16) to (31) above.

In an embodiment of the compounds of formula I:
$R_1$ is as defined in paragraph (4) above;
$R_2$ is as defined in paragraph (8) above;
$R_3$ is as defined in paragraph (12) above;
$R_4$ is as defined in paragraph (14) above;
n is 0 or 1;
Q is as defined in paragraph (22) or (24) above.

In an embodiment of the compounds of formula I:
$R_1$ is as defined in paragraph (4) above;
$R_2$ is as defined in paragraph (8) above;
$R_3$ is as defined in paragraph (12) above;
n is 0;
Q is as defined in paragraph (24) above.

In an embodiment of the compounds of formula I:
$R_1$ is as defined in paragraph (6) above;
$R_2$ is as defined in paragraph (8) above;
$R_3$ is as defined in paragraph (12) above;
n is 0;
Q is as defined in paragraph (22) or (24) above.

In a particular group of compounds of the invention, $R_2$ is H and n is 0, i.e. the compounds have the structural formula Ia (a sub-definition of formula I) shown below:

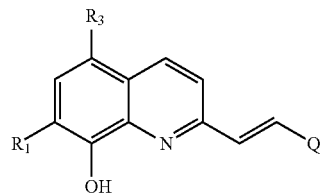

Formula Ia wherein $R_1$, $R_3$, and Q each have any one of the meanings defined herein;
or a pharmaceutically acceptable salt, hydrate and/or solvate thereof.

In a particular group of compounds of the invention, $R_1$ is methyl, $R_2$ is H, $R_3$ is methyl, and n is 0, i.e. the compounds have the structural formula Ib (a sub-definition of formula I) shown below:

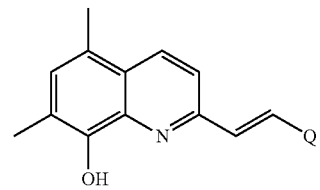

Formula Ib wherein Q has any one of the meanings defined herein;
or a pharmaceutically acceptable salt, hydrate and/or solvate thereof.

In a particular group of compounds of the invention, $R_1$ is methyl, $R_2$ is H, $R_3$ is methyl, n is 0, and Q is a 6-membered aryl or heteroaryl ring (most suitably heteroaryl comprising a single internal heteroatom in the 3-position), i.e. the compounds have the structural formula Ic (a sub-definition of formula I) shown below:

Formula Ic

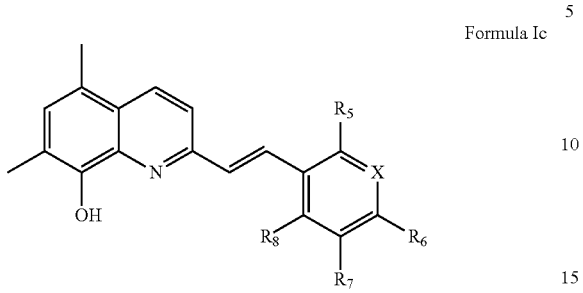

wherein X is CH or N, and $R_5$, $R_6$, $R_7$ and $R_8$ are each independently hydrogen or one of the optional substituents defined hereinbefore in relation to an optionally substituted Q ring system;
or a pharmaceutically acceptable salt, hydrate and/or solvate thereof.

In an embodiment, X is N in the compounds of formula Ic.

In a particular group of compounds of the invention, $R_1$ is methyl, $R_2$ is H, $R_3$ is methyl, n is 0, $R_7$ and $R_8$ are both H, and Q is a 6-membered aryl or heteroaryl ring (most suitably heteroaryl comprising a single internal nitrogen heteroatom in the 3-position), i.e. the compounds have the structural formula Id (a sub-definition of formula I) shown below:

Formula Id

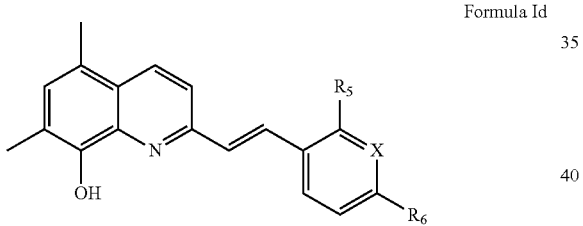

wherein X is CH or N, $R_5$ and $R_6$ are each independently hydrogen or one of the optional substituents defined hereinbefore in relation to an optionally substituted Q ring system;
or a pharmaceutically acceptable salt, hydrate and/or solvate thereof.

In an embodiment, X is N in the compounds of formula Id.

In embodiments where the compounds are of Formula 1c and 1d, $R_5$ is suitably selected from hydrogen, chloro, bromo, (1-4C)alkyl, (1-4C)alkoxy, $NR_cR_c$, or a 4-, 5-, 6-membered heterocyclyl, wherein $R_c$ and $R_d$ are each independently selected from H or (1-4C)alkyl. $R_5$ is suitably hydrogen, chloro, methyl, $NH_2$, or a 6-membered heterocyclyl (e.g. piperazine).

In embodiments where the compounds are of Formula 1c and 1d, $R_6$ is suitably selected from hydrogen, fluoro, (1-4C)alkyl, (1-4C)haloalkyl, (1-4C)alkoxy, (1-4C)haloalkoxy, or a 4-, 5-, 6-membered heterocyclyl, wherein $R_c$ and $R_d$ are each independently selected from H or (1-4C) alkyl. Suitably $R_6$ is hydrogen, (1-4C)alkyl, (1-4C)alkoxy, or a 4-, 5-, 6-membered heterocyclyl. Suitably $R_6$ is hydrogen, methyl, methoxy, or a 6-membered heterocyclyl (e.g. piperazine, morpholine).

Particular compounds of the invention include any one of the following:

(Compound #131)

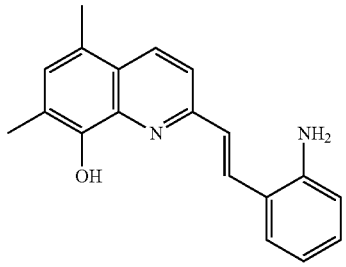

(E)-2-(2-aminostyryl)-5,7-dimethylquinolin-8-ol (Compound #214)

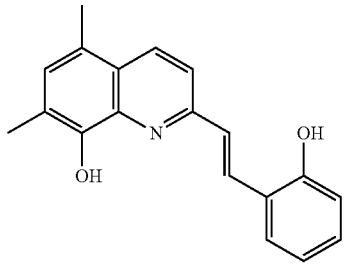

(E)-2-(2-hydroxystyryl)-5,7-dimethylquinolin-8-ol (Compound #221)

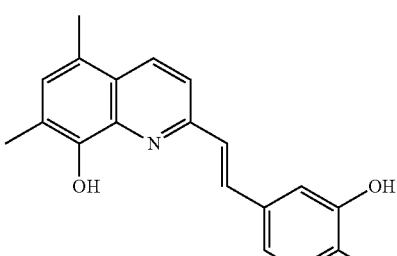

(E)-4-(2-(8-hydroxy-5,7-dimethylquinolin-2-yl)vinyl)benzene-1,2-diol (Compound #222)

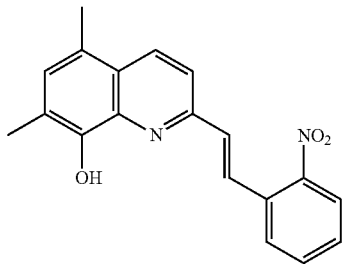

(E)-5,7-dimethyl-2-(2-nitrostyryl)quinolin-8-ol (Compound #225)

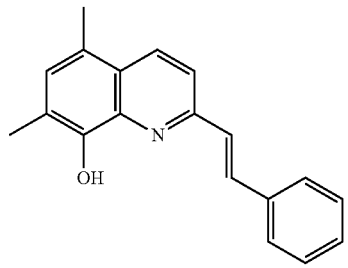

(E)-5,7-dimethyl-2-
styrylquinolin-8-ol (Compound #226)

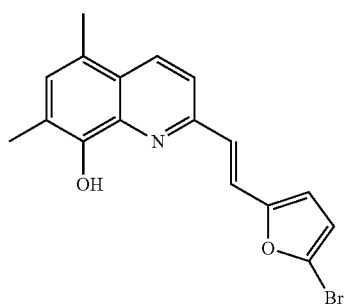

(E)-2-(2-(5-bromofuran-2-yl)vinyl)-
5,7-dimethylquinolin-8-ol (Compound #227)

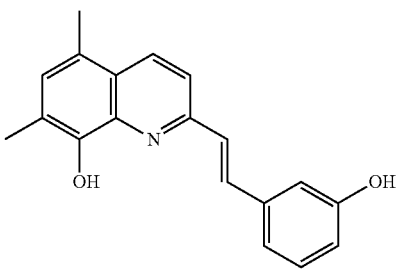

(E)-2-(3-hydroxystyryl)-5,7-
dimethylquinolin-8-ol (Compound #229)

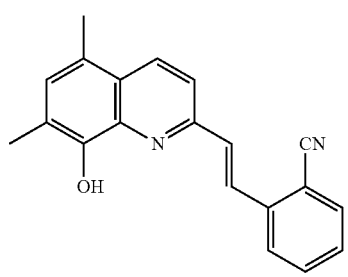

(E)-2-(2-(8-hydroxy-5,7-
dimethylquinolin-2-yl)vinyl)benzonitrile (Compound #234)

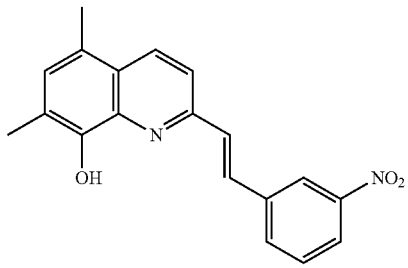

(E)-5,7-dimethyl-2-(3-
nitrostyryl)quinolin-8-ol (Compound #236)

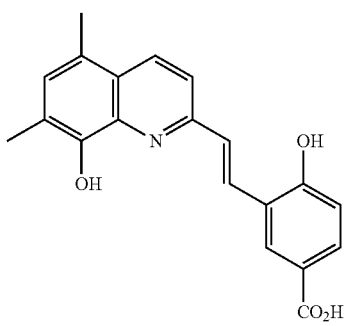

(E)-4-hydroxy-3-(2-(8-hydroxy-5,7-
dimethylquinolin-2-yl)vinyl)benzoic acid (Compound #238)

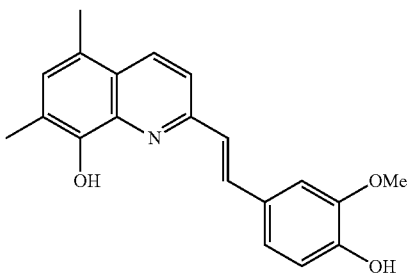

(E)-2-(4-hydroxy-3-methoxystyryl)-
5,7-dimethylquinolin-8-ol (Compound #239)

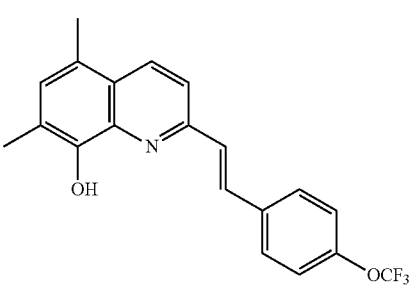

(E)-5,7-dimethyl-2-(4-
(trifluoromethoxy)styryl)quinolin-8-ol (Compound #241)

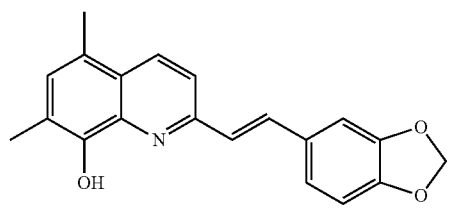

(E)-2-(2-benzo[d][1,3]dioxol-5-yl)vinyl)-
5,7-dimethylquinolin-8-ol (Compound #245)

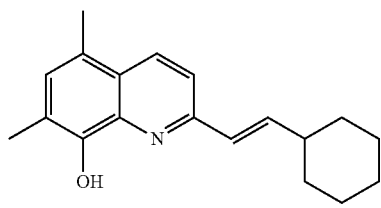

(E)-2-(2-cyclohexylvinyl)-5,7-
dimethylquinolin-8-ol (Compound #249)

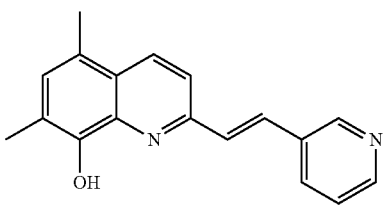

(E)-5,7-dimethyl-2-(2-(pyridin-3-
yl)vinyl)quinolin-8-ol (Compound #251)

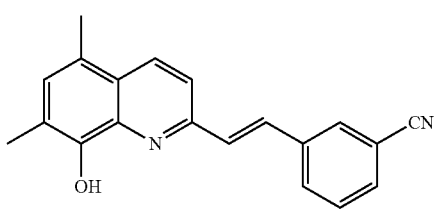

(E)-3-(2-(8-hydroxy-5,7-
dimethylquinolin-2-yl)vinyl)benzonitrile (Compound #252)

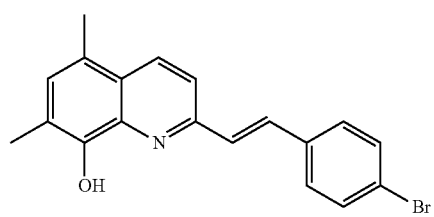

(E)-2-(4-bromostyryl)-5,7-
dimethylquinolin-8-ol (Compound #311)

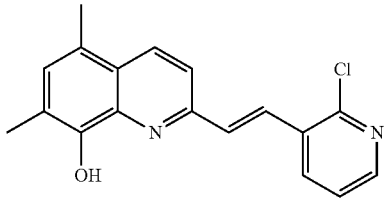

(E)-2-(2-(2-chloropyridine-3-yl)vinyl)-
5,7-dimethylquinolin-8-ol (Compound #312)

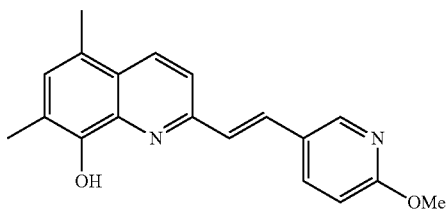

(E)-2-(2-(6-methoxypyridin-3-yl)vinyl)-
5,7-dimethylquinolin-8-ol (Compound #313)

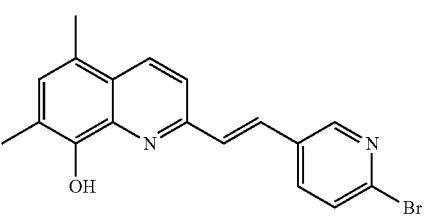

(E)-2-(2-(6-bromopyridin-3-yl)vinyl)-
5,7-dimethylquinolin-8-ol (Compound #314)

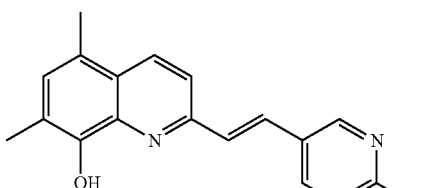

(E)-5,7-dimethyl-2-(2-(6-
(trifluoromethyl)pyridin-3-
yl)vinyl)quinolin-8-ol (Compound #315)

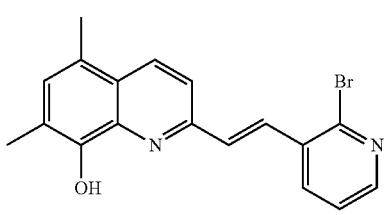

(E)-2-(2-(2-bromopyridin-3-yl)vinyl)-
5,7-dimethylquinolin-8-ol (Compound #316)

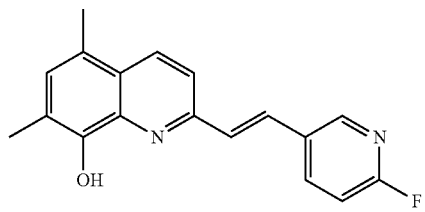

(E)-2-(2-(6-fluoropyridin-3-yl)vinyl)-5,7-
dimethylquinolin-8-ol (Compound #317)

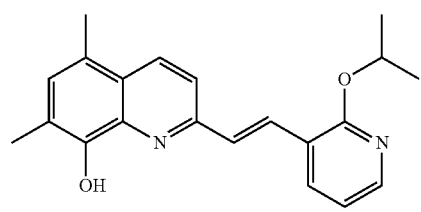

(E)-2-(2-(2-isopropoxypyridin-3-
yl)viny)5,7-dimethylquinolin-8-ol (Compound #318)

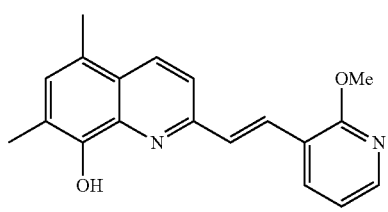

(E)-2-(2-(2-methoxypyridin-3-
yl)vinyl)5,7-dimethylquinolin-8-ol (Compound #319)

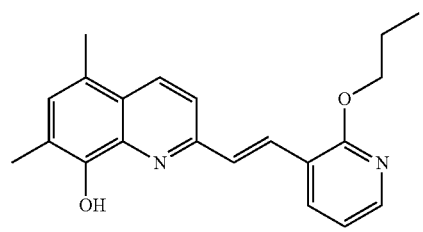

(E)-5,7-dimethyl-2-(2-(2-propoxypyridin-3-
yl)vinyl)quinolin-8-ol (Compound #321)

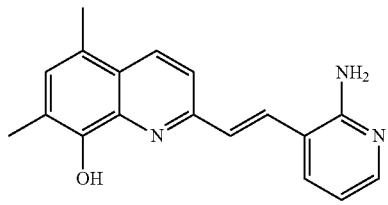

(E)-2-(2-(2-aminopyridin-3-yl)vinyl)-
5,7-dimethylquinolin-8-ol (Compound #322)

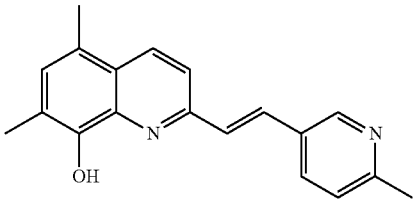

(E)-5,7-dimethyl-2-(2-(6-methylpyridin-3-
yl)vinyl)quinolin-8-ol (Compound #323)

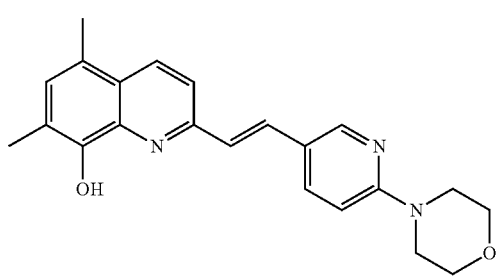

(E)-5,7-dimethyl-2-(2-(6-
morpholinopyridin-3-yl)vinyl)quinolin-8-ol (Compound #324)

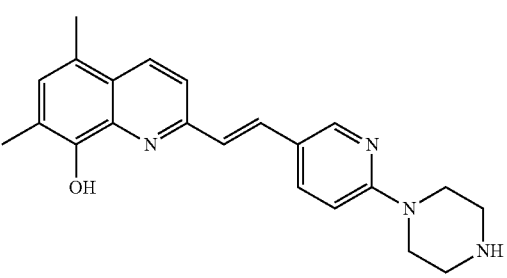

(E)-5,7-dimethyl-2-(2-(6-piperazin-1-
yl)pyridin-3-yl)vinyl)quinolin-8-ol (Compound #325)

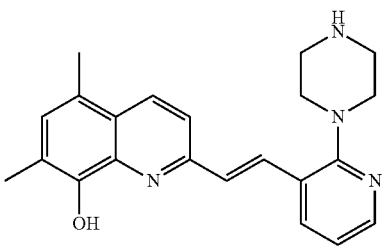

(E)-5,7-dimethyl-2-(2-(2-piperazin-
1-yl)pyridin-3-yl)vinyl)quinolin-8-ol (Compound #326)

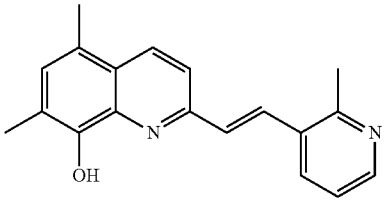

(E)-5,7-dimethyl-2-(2-(2-methylpyridin-
3-yl)vinyl)quinolin-8-ol or a pharmaceutically acceptable salt, hydrate or solvate thereof.

Particular compounds of the invention include any one of the following:

(Compound #249)

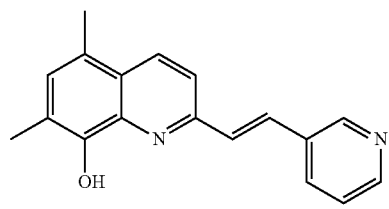

(E)-5,7-dimethyl-2-(2-(pyridin-3-yl)vinyl)quinolin-8-ol (Compound #311)

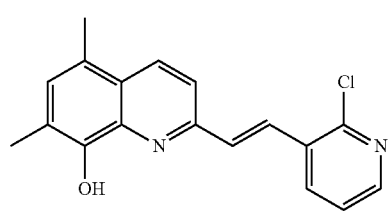

(E)-2-(2-(2-chloropyridin-3-yl)vinyl)-5,7-dimethylquinolin-8-ol (Compound #312)

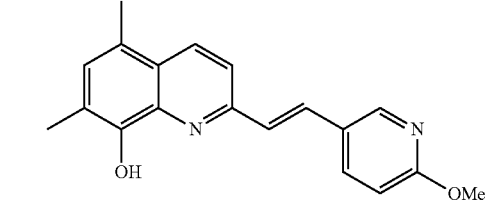

(E)-2-(2-(6-methoxypyridin-3-yl)vinyl)-5,7-dimethylquinolin-8-ol (Compound #313)

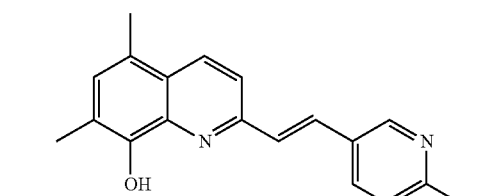

(E)-2-(2-(6-bromopyridin-3-yl)vinyl)-5,7-dimethylquinolin-8-ol (Compound #314)

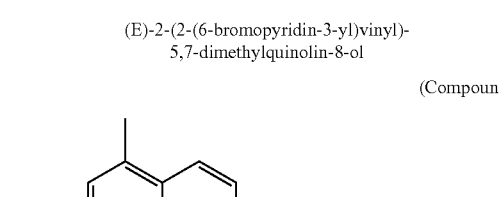

(E)-5,7-dimethyl-2-(2-(6-(trifluoromethyl)pyridin-3-yl)vinyl)quinolin-8-ol (Compound #315)

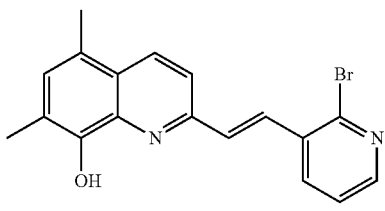

(E)-2-(2-(2-bromopyridin-3-yl)vinyl)-5,7-dimethylquinolin-8-ol (Compound #316)

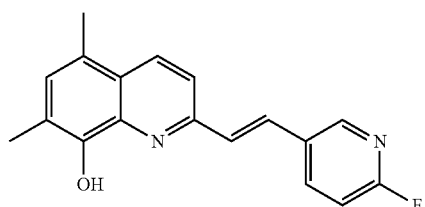

(E)-2-(2-(6-fluoropyridin-3-yl)vinyl)-5,7-dimethylquinolin-8-ol (Compound #317)

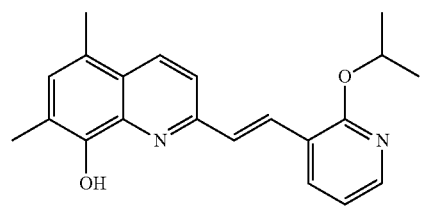

(E)-2-(2-(2-isopropoxypyridin-3-yl)vinyl)-5,7-dimethyquinolin-8-ol (Compound #318)

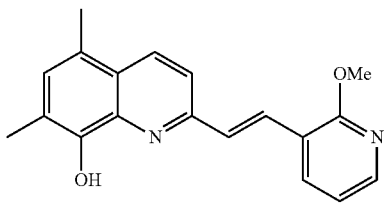

(E)-2-(2-(2-methoxypyridin-3-yl)vinyl)-5,7-dimethylquinolin-8-ol (Compound #319)

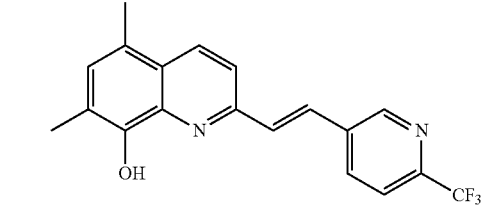

(E)-5,7-dimethyl-2-(2-(2-propoxypyridin-3-yl)vinyl)quinolin-8-ol (Compound #321)

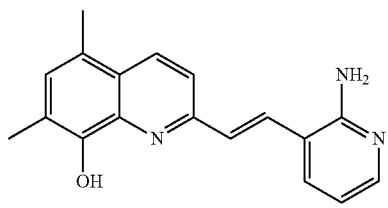

(E)-2-(2-(2-aminopyridin-3-yl)vinyl)-5,7-
dimethylquinolin-8-ol (Compound #322)

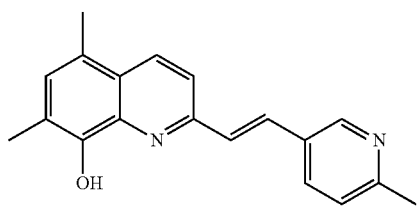

(E)-5,7-dimethyl-2-(2-(6-methylpyridin-3-
yl)vinyl)quinolin-8-ol (Compound #323)

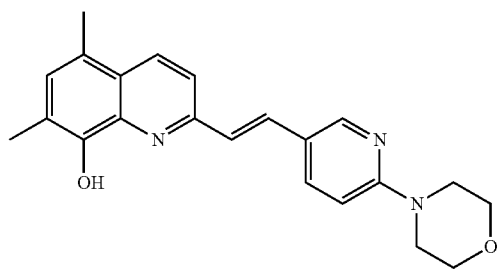

(E)-5,7-dimethyl-2-(2-(6-
morpholinopyridin-3-yl)vinyl)quinolin-8-ol (Compound #324)

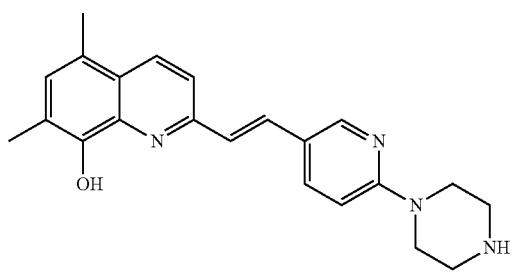

(E)-5,7-dimethyl-2-(2-(6-(piperazin-1-
yl)pyridin-3-yl)vinyl)quinolin-8-ol (Compound #325)

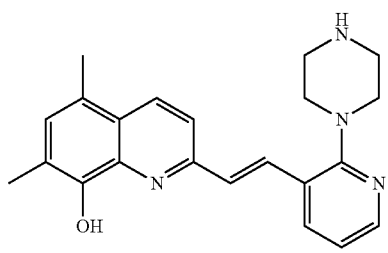

(E)-5,7-dimethyl-2-(2-(2-(piperazin-1-
yl)pyridin-3-yl)vinyl)quinolin-8-ol (Compound #326)

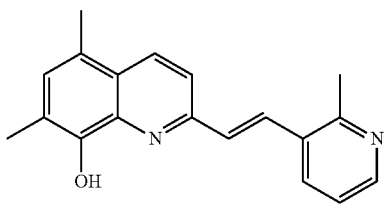

(E)-5,7-dimethyl-2-(2-(2-(methylpyridin-
3-yl)vinyl)quinolin-8-ol or a pharmaceutically acceptable salt, hydrate or solvate thereof.

Further particular compounds of the invention include any one of the following:

(Compound #249)

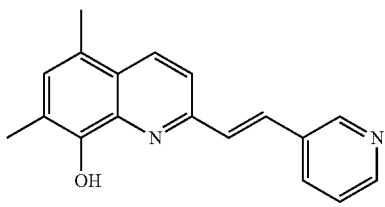

(E)-5,7-dimethyl-2-(2-(pyridin-3-
yl)vinyl)quinolin-8-ol (Compound #311)

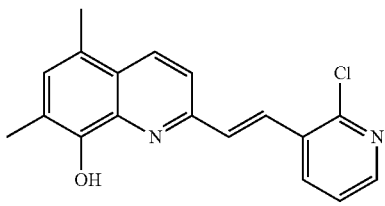

(E)-2-(2-(2-(chloropyridin-3-yl)vinyl)-
5,7-dimethylquinolin-8-ol (Compound #312)

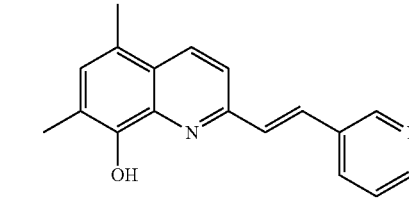

(E)-2-(2-(6-methoxypyridin-3-yl)vinyl)-
5,7-dimethylquinolin-8-ol (Compound #321)

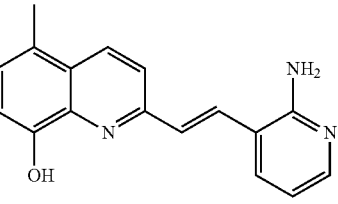

(E)-2-(2-(2-(aminopyridin-3-yl)vinyl)-
5,7-dimethylquinolin-8-ol

-continued

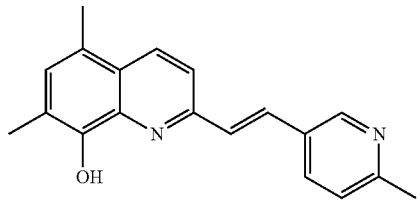

(E)-5,7-dimethyl-2-(2-(6-methylpyridin-3-yl)vinyl)quinolin-8-ol (Compound #323)

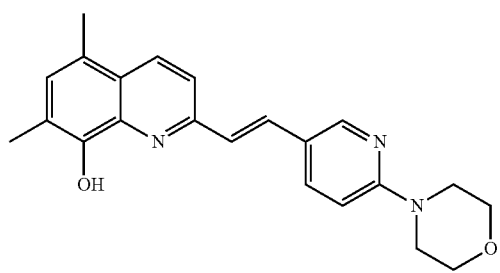

(E)-5,7-dimethyl-2-(2-(6-morpholinopyridin-3-yl)vinyl)quinolin-8-ol (Compound #324)

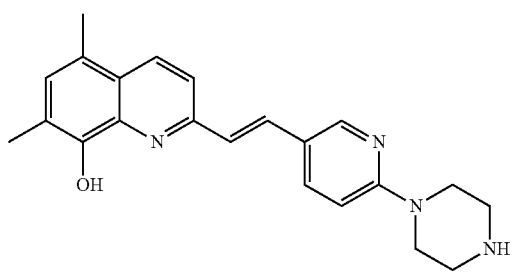

(E)-5,7-dimethyl-2-(2-(6-(piperazin-1-yl)pyridin-3-yl)vinyl)quinolin-8-ol (Compound #325)

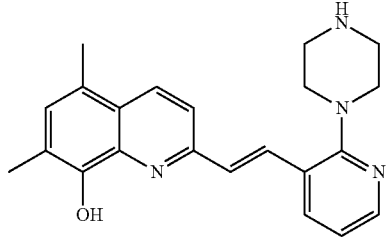

(E)-5,7-dimethyl-2-(2-(2-(piperazin-1-yl)pyridin-3-yl)vinyl)quinolin-8-ol (Compound #326)

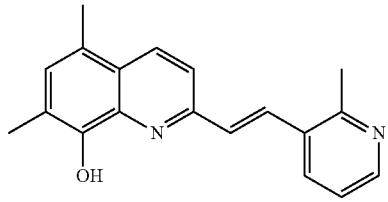

(E)-5,7-dimethyl-2-(2-(2-methylpyridin-3-yl)vinyl)quinolin-8-ol or a pharmaceutically acceptable salt, hydrate or solvate thereof.

Further particular compounds of the invention include any one of the following:

(Compound #249)

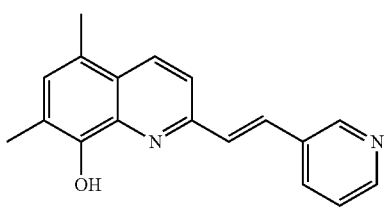

(E)-5,7-dimethyl-2-(2-(pyridin-3-yl)vinyl)quinolin-8-ol (Compound #312)

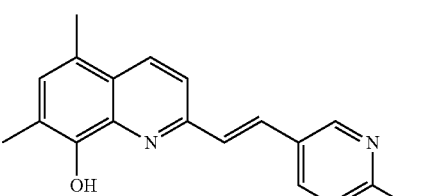

(E)-2-(2-(6-methoxypyridin-3-yl)vinyl)-5,7-dimethylquinolin-8-ol (Compound #321)

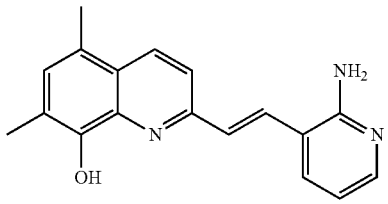

(E)-2-(2-(2-(aminopyridin-3-yl)vinyl)-5,7-dimethylquinolin-8-ol (Compound #322)

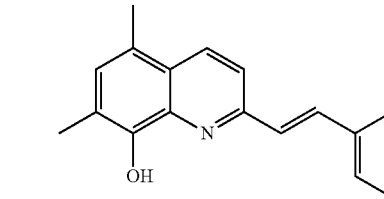

(E)-5,7-dimethyl-2-(2-(6-methylpyridin-3-yl)vinyl)quinolin-8-ol (Compound #323)

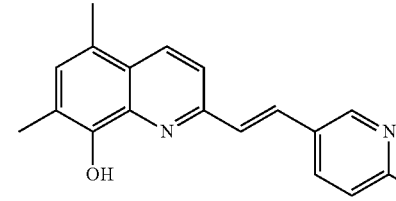

(E)-5,7-dimethyl-2-(2-(6-morpholinopyridin-3-yl)vinyl)quinolin-8-ol

-continued

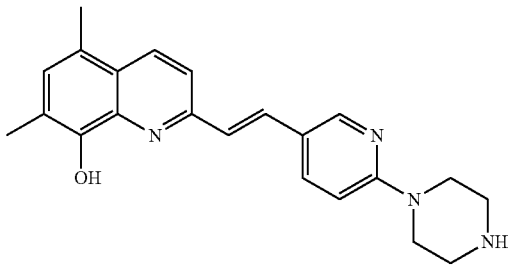

(Compound #324)

(E)-5,7-dimethyl-2-(2-(6-(piperazin-1-yl)pyridin-3-yl)vinyl)quinolin-8-ol

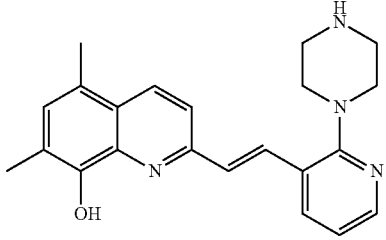

(Compound #325)

(E)-5,7-dimethyl-2-(2-(2-(piperazin-1-yl)pyridin-3-yl)vinyl)quinolin-8-ol

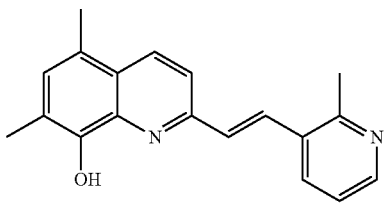

(Compound #326)

(E)-5,7-dimethyl-2-(2-(2-methylpyridin-3-yl)vinyl)quinolin-8-ol or a pharmaceutically acceptable salt, hydrate or solvate thereof.

In a particular embodiment, the compound of the invention is:

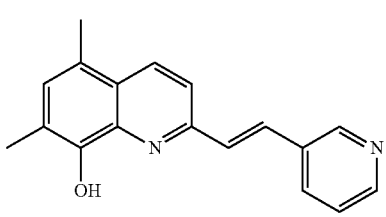

(Compound #249)

(E)-5,7-dimethyl-2-(2-(pyridin-3-yl)vinyl)quinolin-8-ol or a pharmaceutically acceptable salt, hydrate or solvate thereof.

The various functional groups and substituents making up the compounds of the formula I are typically chosen such that the molecular weight of the compound of the formula I does not exceed 1000. More usually, the molecular weight of the compound will be less than 750, for example less than 700, or less than 650, or less than 600, or less than 550. More preferably, the molecular weight is less than 525 and, for example, is 500 or less.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess the relevant activity.

The present invention also encompasses compounds of the invention as defined herein which comprise one or more isotopic substitutions. For example, H may be in any isotopic form, including $^1H$, $^2H(D)$, and $^3H$ (T); C may be in any isotopic form, including $^{12}C$, $^{13}C$, and $^{14}C$; and O may be in any isotopic form, including $^{16}O$ and $^{18}O$; and the like.

It is also to be understood that certain compounds of the formula I may exist in solvated as well as unsolvated forms such as, for example, hydrated forms. It is to be understood that the invention encompasses all such solvated forms that possess activity in the inhibition of amyloid deposit formation.

It is also to be understood that certain compounds of the formula I may exhibit polymorphism, and that the invention encompasses all such forms that possess activity in the inhibition of amyloid deposit formation.

Compounds of the formula I may exist in a number of different tautomeric forms and references to compounds of the formula I include all such forms. For the avoidance of doubt, where a compound can exist in one of several tautomeric forms, and only one is specifically described or shown, all others are nevertheless embraced by formula I. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

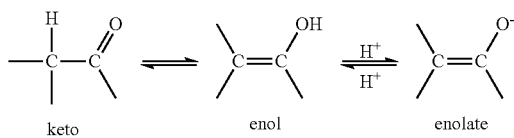

keto      enol      enolate

Compounds of the formula I containing an amine function may also form N-oxides. A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as dichloromethane.

The compounds of formula I may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the formula I and in-vivo cleavable amide derivatives that may be formed at a carboxy group or an amino group in a compound of the formula I.

Accordingly, the present invention includes those compounds of the formula I as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula I may be a synthetically-produced compound or a metabolically-produced compound.

A suitable pharmaceutically acceptable pro-drug of a compound of the formula I is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the formula I that possesses a carboxy group is, for example, an in vivo cleavable ester thereof. An in vivo cleavable ester of a compound of the formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the formula I that possesses a hydroxy group is, for example, an in vivo cleavable ester or ether thereof. An in vivo cleavable ester or ether of a compound of the formula I containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$ alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the formula I that possesses a carboxy group is, for example, an in vivo cleavable amide thereof, for example an amide formed with an amine such as ammonia, a $C_{1-4}$alkylamine such as methylamine, a $(C_{1-4}$alkyl$)_2$amine such as dimethylamine, N-ethyl-N-methylamine or diethylamine, a $C_{1-4}$alkoxy-$C_{2-4}$ alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of the formula I that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the formula I may be exerted in part by one or more metabolites that are formed within the human or animal body after administration of a compound of the formula I. As stated hereinbefore, the in vivo effects of a compound of the formula I may also be exerted by way of metabolism of a precursor compound (a pro-drug).

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Suitably, the present invention excludes any individual compounds not possessing the biological activity defined herein.

Suitably, (substantially) all compounds of the invention are suitable for treating type-2 diabetes. Compounds of the invention which are capable of crossing the blood-brain barrier, or those which may be otherwise formulated or derivatised (e.g. as a prodrug or appropriate salt) to do so, are suitably suitable for treating Alzheimer's disease.

Synthesis

The compounds of the present invention can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the invention in the processes defined herein, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The methodology employed to synthesise a compound of formula I will vary depending on the nature of $R_1$, $R_2$, $R_3$, $R_4$, n, and Q, and any substituent groups associated therewith. Suitable processes for their preparation are described further in the accompanying Examples.

Once a compound of formula I (or a protected precursor therefor) has been synthesised by any one of the processes defined herein, the processes may then further comprise the additional steps of:

(i) removing any protecting groups present;
(ii) converting the compound formula I into another compound of formula I;
(iii) forming a pharmaceutically acceptable salt, hydrate or solvate thereof; and/or
(iv) forming a prodrug thereof.

An example of (ii) above is when a compound of formula I is synthesised and then one or more of the groups of $R_1$, $R_2$, $R_3$, $R_4$, and Q, may be further reacted to change the nature of the group and provide an alternative compound of formula I.

The resultant compounds of formula I can be isolated and purified using techniques well known in the art.

The present invention provides a process for preparing a compound of formula I (as defined herein), the process comprising the steps of:
reacting a compound of formula A:

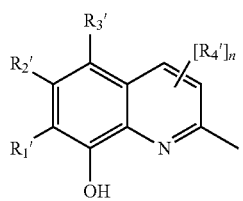

Formula A with a compound of formula B:

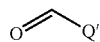

Formula B to form a compound of formula I':

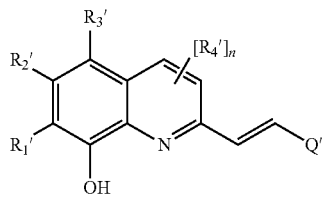

Formula I' wherein either:
a) all of $R_1'$, $R_2'$, $R_3'$, $R_4'$, n, and Q' have any one of the meanings defined herein in relation to the respectively labelled $R_1$, $R_2$, $R_3$, $R_4$, n and Q groups of Formula I such that the compound of Formula I' is a compound of Formula I; or
b) one or more of $R_1'$, $R_2'$, $R_3'$, $R_4'$, and Q' are precursors to the corresponding $R_1$, $R_2$, $R_3$, $R_4$ and Q groups in formula I as defined herein, in which case said compound of Formula I' is thereafter transformed into the compound of Formula I by further reaction to convert any such precursor groups into a group $R_1$, $R_2$, $R_3$, $R_4$, and Q of Formula I as defined herein;
and optionally thereafter (and if necessary):
(i) transforming the compound of Formula I into another compound of Formula I by, for example, converting one or more of $R_1$, $R_2$, $R_3$, $R_4$ (if n is non-zero), and Q into another group $R_1$, $R_2$, $R_3$, $R_4$ (if n is non-zero), and Q according to formula I defined herein;
(ii) removing any protecting groups present (e.g. from the alcohol/phenol group);
(iii) forming a pharmaceutically acceptable salt, hydrate or solvate thereof; and/or
(iv) forming a prodrug thereof.

Suitably the molar ratio of the compound of formula A to the compound of formula B is between 5:1 and 1:5, most suitably between 1:2 and 1:4. Most suitably, an excess of the compound of formula B is used relative to the compound of formula A.

Suitably, the process involves contacting the compounds of formula A and B with an electrophilic activator (e.g. acetic anhydride, acetyl chloride, etc.). Where acetic anhydride is the electrophilic activator compound, this may also serve as a solvent.

Suitably, the process takes place at elevated temperature, suitably with the reaction mixture at a temperature at or above 60° C., suitably at or above 100° C., suitably at or above 120° C.

Suitably, the process involves contacting both of the compounds of formula A and B with a base or nucleophilic activator (e.g. pyridine). Such a step may also proceed in the presence of a protic solvent, such as water. Where pyridine is the base or nucleophilic activator, this may also serve as a solvent or co-solvent. Suitably, such a step takes place at elevated temperature, suitably with the reaction mixture at a temperature at or above 60° C., suitably at or above 100° C., suitably at or above 120° C.

Where one or more of $R_1'$, $R_2'$, $R_3'$, $R_4'$ and Q' of Formula I' are precursors to the corresponding $R_1$, $R_2$, $R_3$, $R_4$ and Q groups in formula I, said one or more groups may be converted into a corresponding $R_1$, $R_2$, $R_3$, $R_4$, and Q group of Formula I by subjecting the compound of formula I' to appropriate deprotection conditions and/or by effecting a substitution of one or more of the $R_1'$, $R_2'$, $R_3'$, $R_4'$, n, and Q' group(s) with a corresponding $R_1$, $R_2$, $R_3$, $R_4$ and Q group of Formula I.

The final compound of formula I may be obtained after purification by, for example, chromatography (e.g. flash silica chromatography) and/or recrystallisation.

The compounds of Formula A and B are intermediates from which a variety of compounds of formula I can be made.

In a further aspect of the invention, there is provided a compound of formula I obtainable by a process as defined herein.

In a further aspect of the invention, there is provided a compound of formula I obtained by a process as defined herein.

In a further aspect of the invention, there is provided a compound of formula I directly obtained by a process as defined herein.

In a further aspect of the present invention there is provided a novel intermediate compound of formula A or B as defined herein.

Biological Activity

The biological assays described in Examples A and B herein may be used to measure the pharmacological effects of the compounds of the present invention. The pharmacological properties of compounds of the invention were studied by way of a dose response and IC50 against IAPP, a screen against Amyloid-beta (Aβ) peptides, and an in vivo screen with C. elegans.

Although the pharmacological properties of the compounds of formula I vary with structural change, as expected, the compounds of the invention were found to be active in the assays described in Example A and/or Example B, with the exception of (E)-2-(2-(6-chloropyridin-3-yl)vinyl)-5,7-dimethylquinolin-8-ol.

Pharmaceutical Compositions

According to a further aspect of the invention there is provided a pharmaceutical composition which comprises a compound of the invention as defined hereinbefore, or a pharmaceutically acceptable salt, hydrate or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The present invention provides compounds that inhibit the formation of amyloid deposits and/or amyloidosis. As such, the compounds of the invention are particular suitable for inhibiting apoptotic or excitotoxic cell-death and for treating a disease or disorder in which amyloid deposits or amyloidosis is implicated, such as type-2 diabetes or Alzheimer's disease.

The compounds for use in the therapeutic uses and applications of the present invention are those defined hereinbefore, except that the proviso recited herein before (whereby when $R_1$ and $R_3$ are methyl, $R_2$ is H and n is 0, then Q is not 2-aminophenyl) does not apply, i.e. the compounds for use in these are compounds of formula I in which:

wherein:
$R_1$ is selected from halo, (1-3C)alkyl, (1-3C)haloalkyl, (1-3C)alkoxy, (1-3C)haloalkoxy;
$R_2$ is selected from hydrogen or fluoro;
$R_3$ is selected from halo, (1-3C)alkyl, (1-3C)haloalkyl, (1-3C)alkoxy, (1-3C)haloalkoxy;
$R_4$ is selected from halo, (1-3C)alkyl, (1-3C)haloalkyl;
n is 0, 1, or 2;
Q is a ring system selected from phenyl, 5- or 6-membered heteroaryl, or (5-7C)cycloalkyl, each of which is optionally fused to a 5- or 6-membered heterocyclyl (e.g. to form a methylenedioxy-substituted Q ring system) ring, and wherein the Q ring system isoptionally substituted by: one, two, or three $R_Q$ groups; wherein $R_Q$ is independently selected from halo, hydroxy, nitro, cyano, (1-4C)alkyl, (1-4C)haloalkyl, (1-4C)alkoxy, (1-4C)haloalkoxy, $NR_cR_c$, $C(O)R_c$, $C(O)OR_c$, $OC(O)R_c$, $C(O)N(R_d)R_c$, $N(R_c)C(O)R_d$, $S(O)_pR_c$ (where p is 0, 1 or 2), $SO_2N(R_c)R_d$, $N(R_c)SO_2R_d$, or a 4-, 5-, 6-membered heterocyclyl, wherein $R_c$ and $R_d$ are each independently selected from H or (1-4C)alkyl;
or a pharmaceutically acceptable salt, hydrate or solvate thereof.

Therefore, the present invention provides a method of inhibiting the formation of amyloid deposits (in vivo or in vitro), said method comprising contacting a tissue or cell with an effective amount of a compound or a pharmaceutically acceptable salt, hydrate or solvate thereof as defined herein.

The present invention also provides a method of inhibiting amyloidosis (in vivo or in vitro), said method comprising contacting a tissue or cell with an effective amount of a compound or a pharmaceutically acceptable salt, hydrate or solvate thereof as defined herein.

According to a further aspect of the present invention, there is provided a method of inhibiting the formation of cytotoxic aggregates of amyloid-beta (Ab) peptides (in vivo or in vitro), said method comprising contacting a tissue or cell with an effective amount of a compound or a pharmaceutically acceptable salt, hydrate or solvate thereof as defined herein.

According to a further aspect of the present invention, there is provided a method of inhibiting the formation of cytotoxic aggregates of Islet Amyloid Polypeptide (IAPP) (in vivo or in vitro), said method comprising contacting a tissue or cell with an effective amount of a compound or a pharmaceutically acceptable salt, hydrate or solvate thereof as defined herein.

According to a further aspect of the present invention, there is provided a method of inhibiting apoptotic or excitotoxic cell-death, in vitro or in vivo, said method comprising contacting a cell with an effective amount of a compound or a pharmaceutically acceptable salt, hydrate or solvate thereof as defined herein, or a pharmaceutical composition as defined herein.

According to a further aspect of the present invention, there is provided a method of treating a disease or disorder in which amyloid deposits or amyloidosis is implicated in a patient in need of such treatment, said method comprising administering to said patient a therapeutically effective amount of a compound or a pharmaceutically acceptable salt, hydrate or solvate thereof as defined herein, or a pharmaceutical composition as defined herein.

According to a further aspect of the present invention, there is provided a method of treating Alzheimer's disease, or the symptoms thereof, in a patient in need of such treatment, said method comprising administering to said patient a therapeutically effective amount of a compound or a pharmaceutically acceptable salt, hydrate or solvate thereof as defined herein, or a pharmaceutical composition as defined herein.

According to a further aspect of the present invention, there is provided a method of treating type-2 diabetes, or the symptoms thereof, in a patient in need of such treatment, said method comprising administering to said patient a therapeutically effective amount of a compound or a pharmaceutically acceptable salt, hydrate or solvate thereof as defined herein, or a pharmaceutical composition as defined herein.

According to a further aspect of the present invention, there is provided a compound, or a pharmaceutically acceptable salt, hydrate or solvate thereof, or a pharmaceutical composition as defined herein for use in therapy.

According to a further aspect of the present invention, there is provided a compound or a pharmaceutically acceptable salt, hydrate or solvate thereof as defined herein, or a pharmaceutical composition as defined herein, for use in inhibiting the formation of amyloid deposits (in vivo or in vitro).

According to a further aspect of the present invention, there is provided a compound or a pharmaceutically acceptable salt, hydrate or solvate thereof as defined herein, or a pharmaceutical composition as defined herein, for use in inhibiting amyloidosis (in vivo or in vitro).

According to a further aspect of the present invention, there is provided a compound or a pharmaceutically acceptable salt, hydrate or solvate thereof as defined herein, or a pharmaceutical composition as defined herein, for use in inhibiting the formation of cytotoxic aggregates of amyloid-beta (Ab) peptides (in vivo or in vitro).

According to a further aspect of the present invention, there is provided a compound or a pharmaceutically acceptable salt, hydrate or solvate thereof as defined herein, or a pharmaceutical composition as defined herein, for use in inhibiting the formation of cytotoxic aggregates of Islet Amyloid Polypeptide (IAPP) (in vivo or in vitro).

According to a further aspect of the present invention, there is provided a compound or a pharmaceutically acceptable salt, hydrate or solvate thereof as defined herein, or a pharmaceutical composition as defined herein, for use in inhibiting apoptotic or excitotoxic cell-death (in vivo or in vitro).

According to a further aspect of the present invention, there is provided a compound or a pharmaceutically acceptable salt, hydrate or solvate thereof as defined herein, or a pharmaceutical composition as defined herein, for use in treating a disease or disorder in which amyloid deposits or amyloidosis is implicated.

According to a further aspect of the present invention, there is provided a compound or a pharmaceutically acceptable salt, hydrate or solvate thereof as defined herein, or a pharmaceutical composition as defined herein, for use in treating Alzheimer's disease, or the symptoms thereof.

According to a further aspect of the present invention, there is provided a compound or a pharmaceutically acceptable salt, hydrate or solvate thereof as defined herein, or a pharmaceutical composition as defined herein, for use in treating type-2 diabetes, or the symptoms thereof.

Amyloid deposits may suitably mean amyloid oligomers, fibrils or plaques.

Routes of Administration

The compounds of the invention or pharmaceutical compositions comprising these compounds may be administered to a subject by any convenient route of administration, whether systemically/peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The treatments defined hereinbefore may be applied as a sole therapy or may involve, in addition to the compound of the invention, conventional surgery or additional drug therapy. Such additional drug therapy may include one or more of the following categories of agents:—
  i. acetylcholinesterase inhibitors;
  ii. beta secretase inhibitors;
  iii. gamma secretase inhibitors;
  iv. antibodies to Abeta whether derived by passive or active immunisation.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination for use in the treatment of a disease or disorder in which amyloid deposits or amyloidosis is implicated (e.g. type-2 diabetes and/or Alzheimer's disease) comprising a compound of the invention as defined hereinbefore, or a pharmaceutically acceptable salt, hydrate or solvate thereof, and another therapeutic agent.

According to this aspect of the invention there is provided a combination for use in the treatment of a disease or disorder in which amyloid deposits or amyloidosis is implicated (e.g. type-2 diabetes and/or Alzheimer's disease) comprising a compound of the invention as defined hereinbefore, or a pharmaceutically acceptable salt, hydrate or solvate thereof, and any one of the agents listed herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt, hydrate or solvate thereof, in combination with an agent (optionally selected from one listed herein above), in association with a pharmaceutically acceptable diluent or carrier.

EXAMPLES

Materials and Equipment

All reactions involving organometallic or other moisture-sensitive reagents were carried out under a nitrogen or argon atmosphere using standard vacuum line techniques and flame-dried glassware that was cooled under nitrogen before use. Solvents were dried according to the procedure outlined by Grubbs (Pangborn, A. B. G., M. A; Grubbs, R. H; Rosen, R. K; Timmers, F. J 1996, 15, 1518). Solvents were degassed by sparging with nitrogen gas for 30 minutes prior to use. Water was purified by an Elix® UV-10 system. All other reagents were used as supplied (analytical or HPLC grade) without further purification. Organic layers were dried over $MgSO_4$. Petroleum ether (pet. ether) refers to the fraction of petrol boiling in the range of 40-60° C.; brine denotes a sat. aq. solution of NaCl. Thin layer chromatography was performed on aluminium plates coated with 60 $F_{254}$ silica. Plates were visualised using UV light (254 nm), iodine, or 1% aq. $KMnO_4$. Flash column chromatography was performed on Macherery-Nagel Kieselgel 60M silica on a glass column. Melting points were recorded on a Gallenkamp Hot Stage apparatus and are reported uncorrected. IR spectra were recorded on a Bruker Tensor 27 FT-IR spectrometer with a diamond ATR module; selected characteristic peaks are reported in $cm^{-1}$. NMR spectra were recorded on Bruker Advance spectrometers in $d_6$-DMSO or $CDCl_3$ unless otherwise stated. Chemical shifts (δ) are reported in ppm relative to residual deuterated solvent and coupling constants (J) are reported in Hz and rounded to the nearest 0.1 Hz. The multiplicity of each signal is designated using the following abbreviations; s, d, dd, t, dt, q, quin, m, comp, denoting singlet, doublet, doublet of doublets, triplet, doublet of triplets, quartet, quintet, multiplet and composite multiplet of non-magnetically equivalent protons respectively. Spectra were recorded at ambient temperature, unless otherwise stated. Low-resolution mass spectra were recorded on either a VG MassLab 20-250 or a Micromass Platform 1 spectrometer. Accurate mass measurements were run on either a Bruker MicroTOP internally calibrated with polyalanine, or a Micromass GCT instrument fitted with a Scientific Glass Instruments BPX5 column (15 m×0.25 mm) using amyl acetate as a lock mass.

Preparation of Example Compounds

All compounds of the invention were formed via the general reaction schemes (Scheme 1 and 2) shown below.

Scheme 1

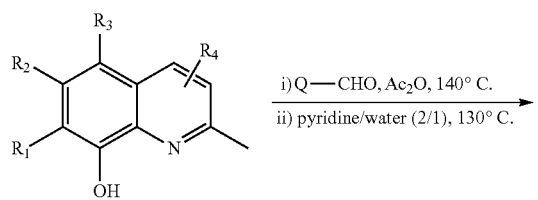

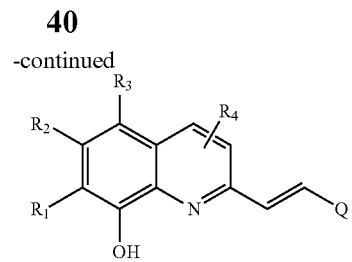

Scheme 2

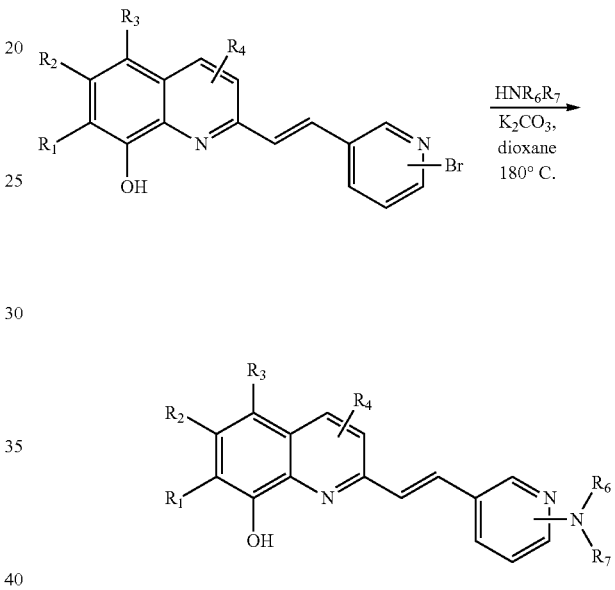

Styrene Formation (Scheme 1)

To a solution of the quinolinol derivative (1 eq) in $Ac_2O$ (8 mL per mmol) was added the requisite aldehyde (3 eq) in a microwave vial. The tube was sealed and the reaction heated to 140° C. for 16 h, cooled down and concentrated in vacuo. The residue was dissolved in pyridine/water (2/1-12 mL per mmol) and heated to 130° C. for 3 h. The reaction was allowed to cool down overnight and concentrated in vacuo. The desired product was obtained after purification on silica gel (EtOAc/pet) and recrystallisation from $Et_2O$/pet as required.

$S_NAr$ Reaction (Scheme 2) e.g. Cpds #324 and #325

Solid potassium carbonate (2 eq) and the requisite amine (2.5 eq) were added to a solution of the bromopyridine derivative (1 eq) in 1,4-dioxane (1M solution in bromopyridine), and the reaction vessel sealed and heated at ca. 180° C. for 1 h. The reaction was allowed to cool to ambient temperature, then concentrated in vacuo. The resulting residue was partitioned between ethyl acetate and water, and the aqueous phase extracted with additional ethyl acetate. The combined organic phases were dried, evaporated and purified by chromatography on silica gel, eluting with chloroform/methanol (95:5, to 9:1 v/v) to provide the desired product.

Using the above reaction schemes, the following specific compounds were prepared:

Example 1—Compound 131

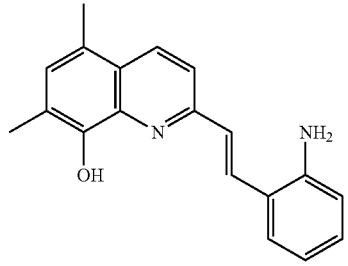

(Compound #131)

(E)-2-(2-aminostyryl)-5,7-dimethylquinolin-8-ol

Example 2—Compound 214

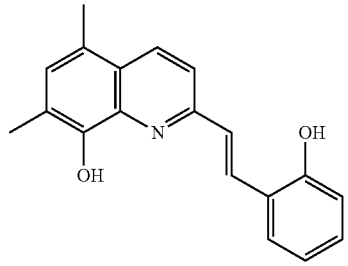

(Compound #214)

(E)-2-(2-hydroxystyryl)-5,7-dimethylquinolin-8-ol

Figure 1B:
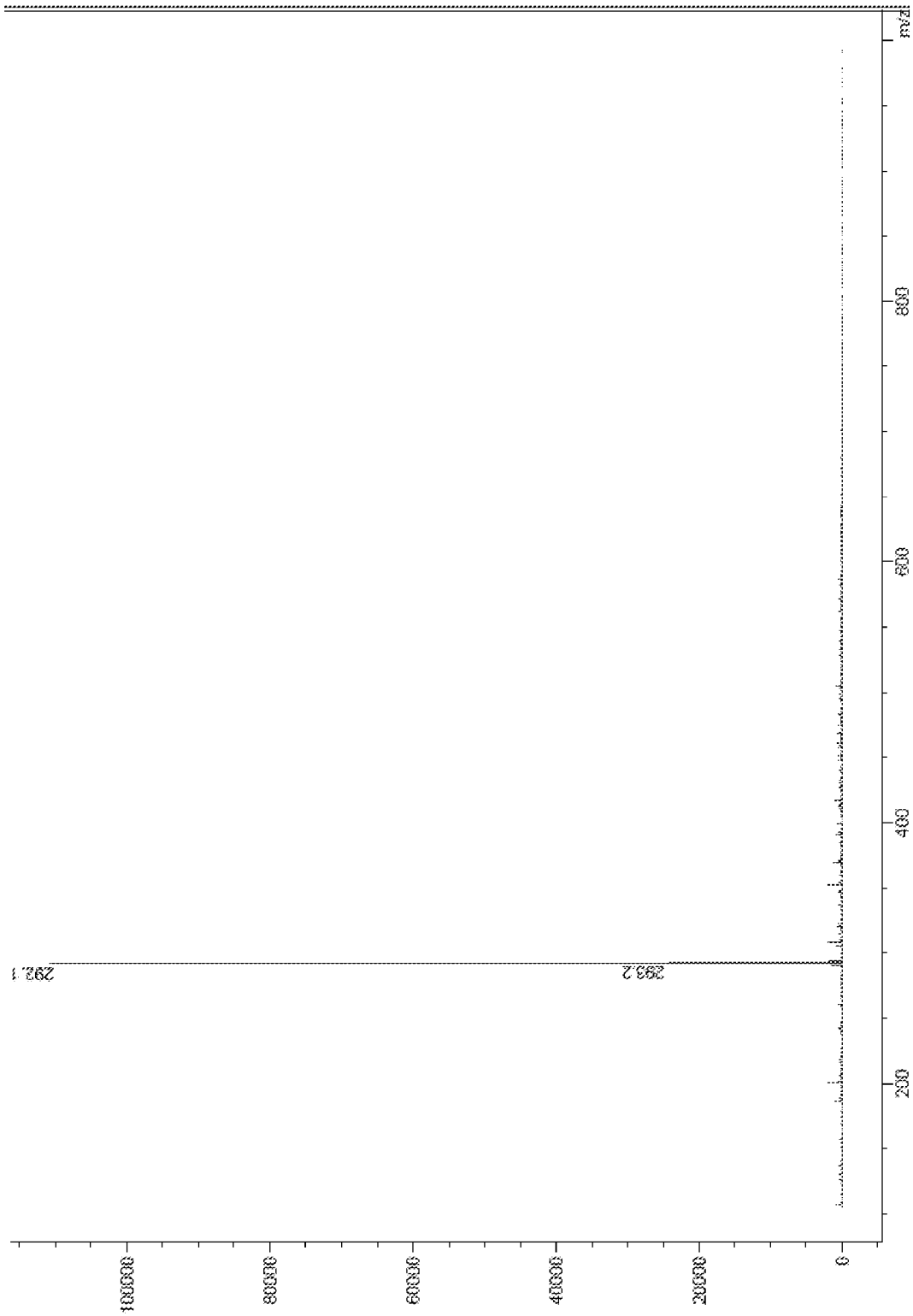

FIG. 1 shows spectroscopic ($^1$H NMR) and spectrometric (mass spec) characterisation of compound 214.

Example 3—Compound 221

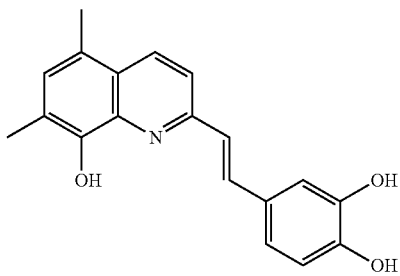

(Compound #221)

(E)-4-(2-(8-hydroxy-5,7-dimethylquinolin-2-yl)vinyl)benzene-1,2-diol

Figure 2A:
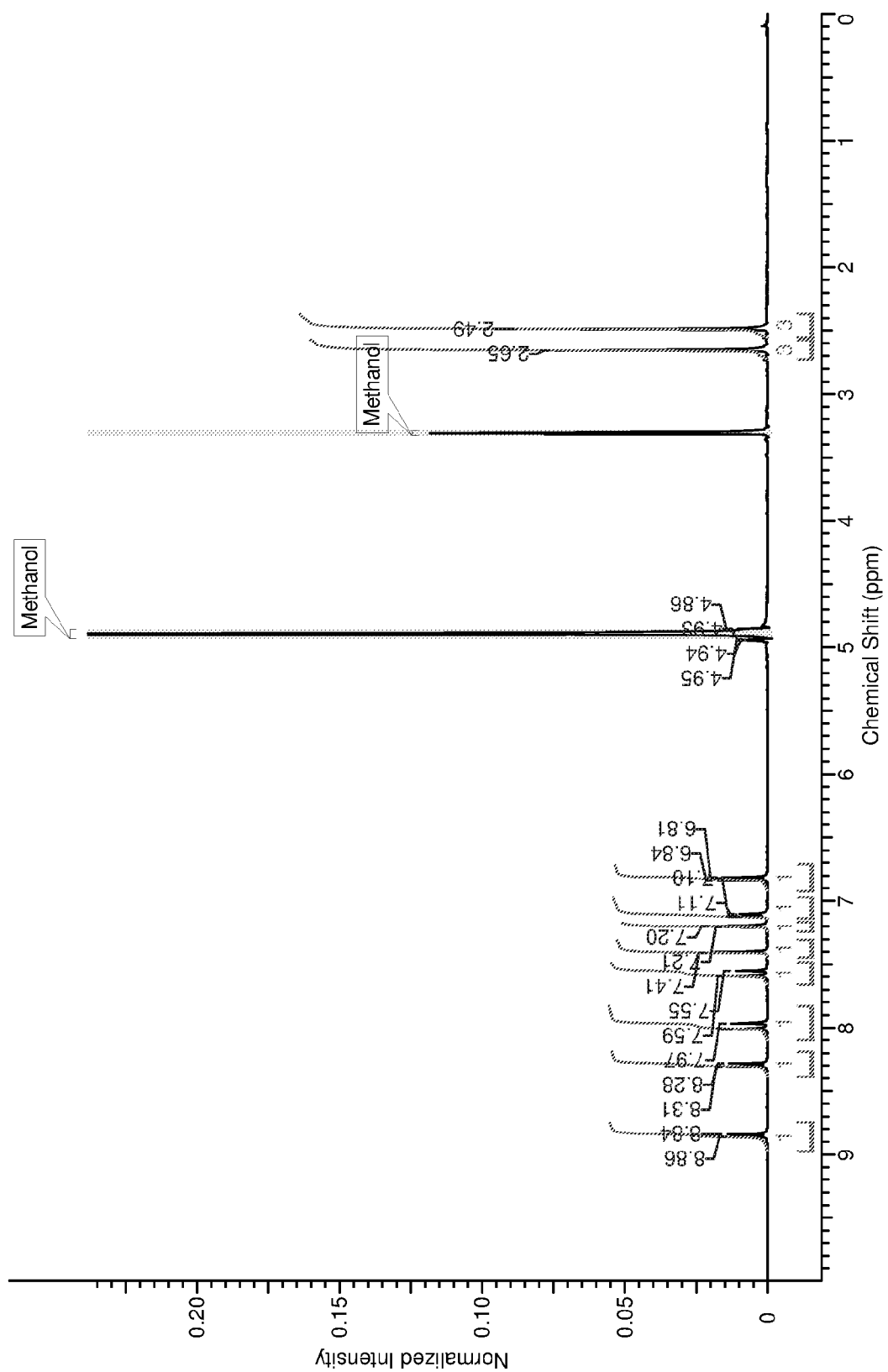
FIG. 2 shows the a) $^1$H NMR characterisation data and b) mass spectrometry characterisation data for compound 221.

FIG. 2 shows spectroscopic ($^1$H NMR) and spectrometric (mass spec) characterisation of compound 221.

Example 4—Compound 222

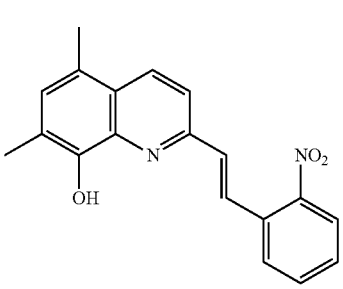

(Compound #222)

(E)-5,7-dimethyl-2-(2-nitrostyryl)quinolin-8-ol

Figure 3A:
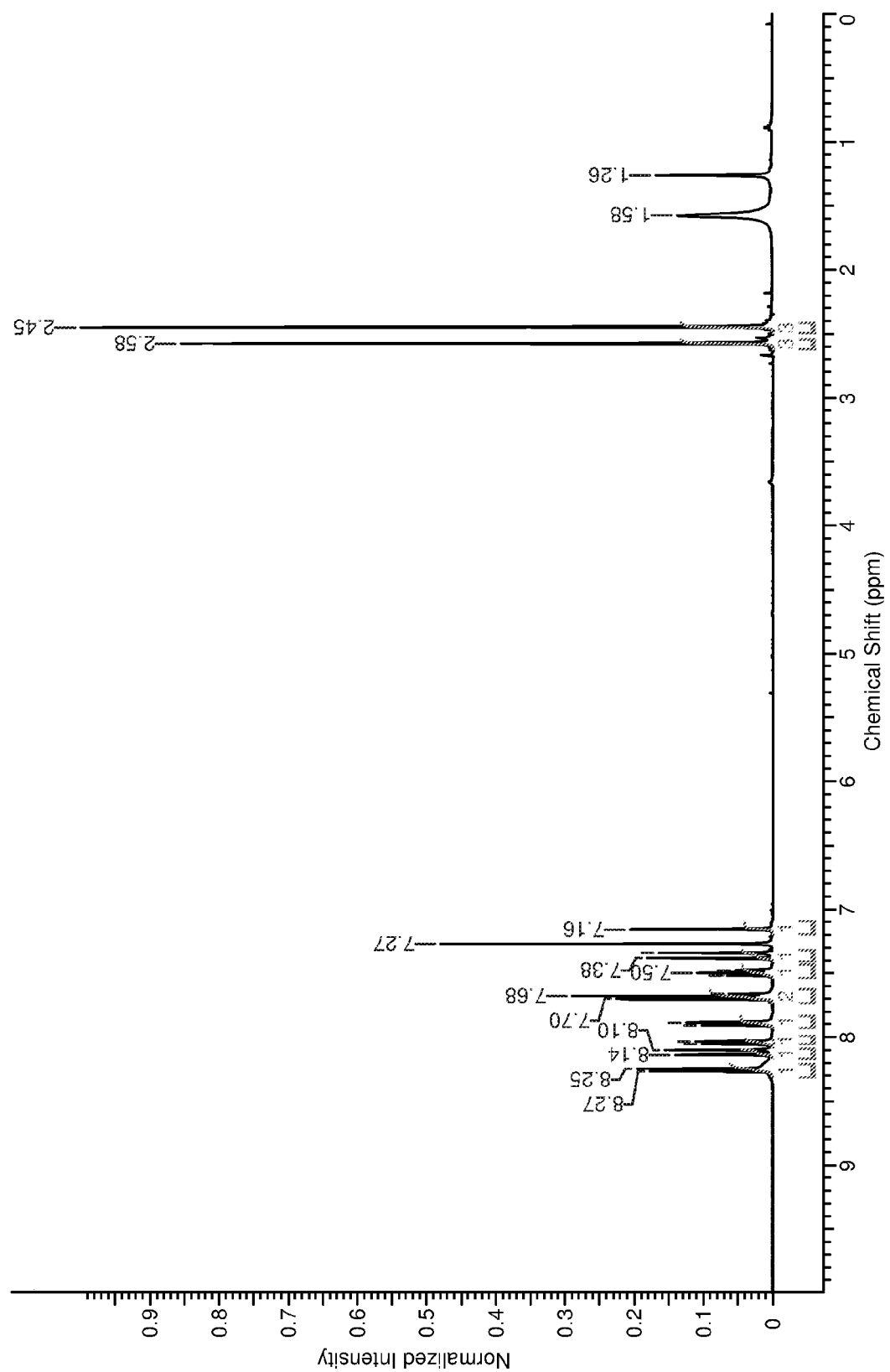
FIG. 3 shows the a) $^1$H NMR characterisation data and b) mass spectrometry characterisation data for compound 222.
Figure 3B:
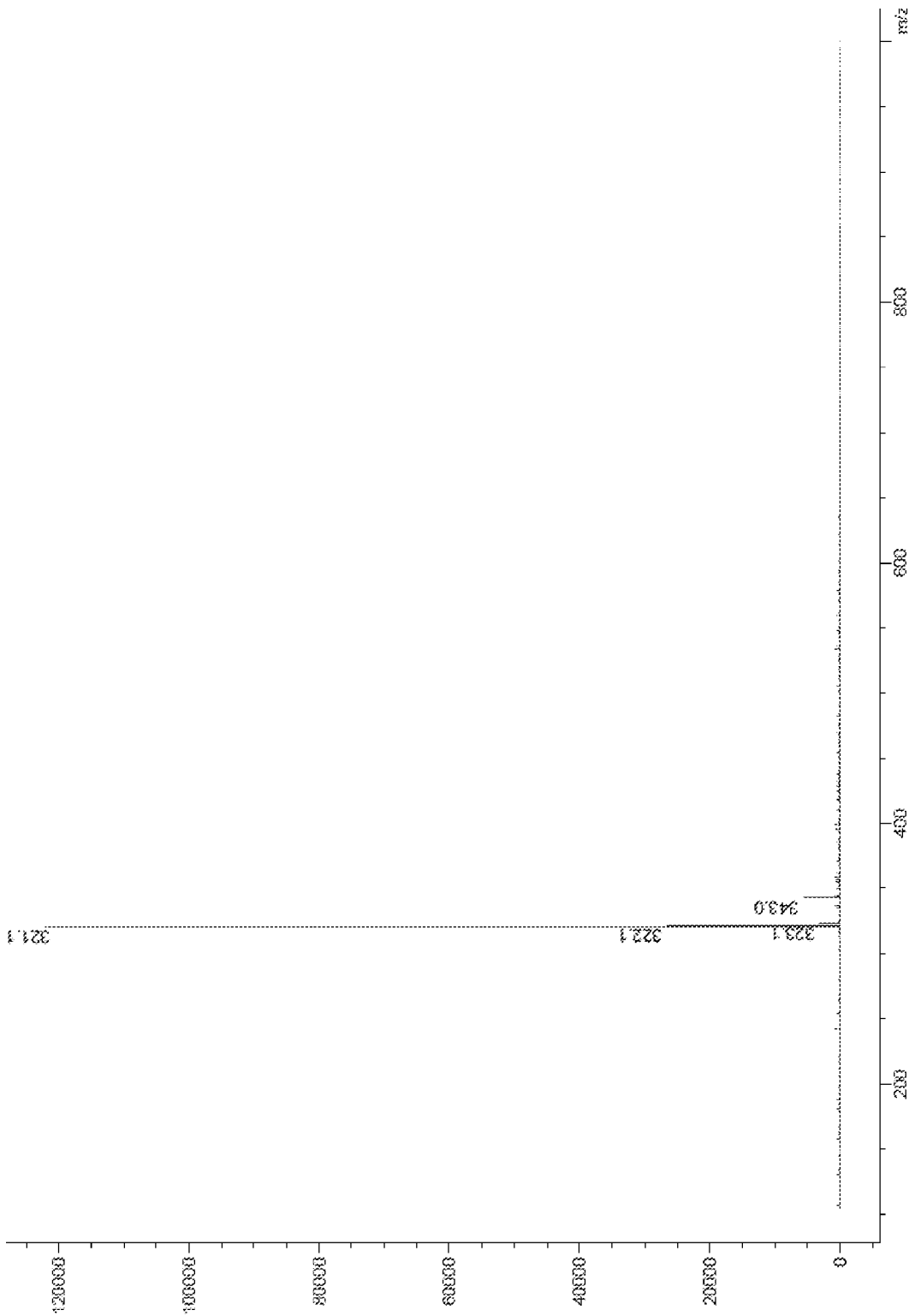

FIG. 3 shows spectroscopic ($^1$H NMR) and spectrometric (mass spec) characterisation of compound 222.

Example 5—Compound 225

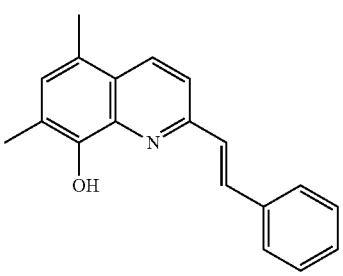

(Compound #225)

(E)-5,7-dimethyl-2-styrylquinolin-8-ol

Figure 4:
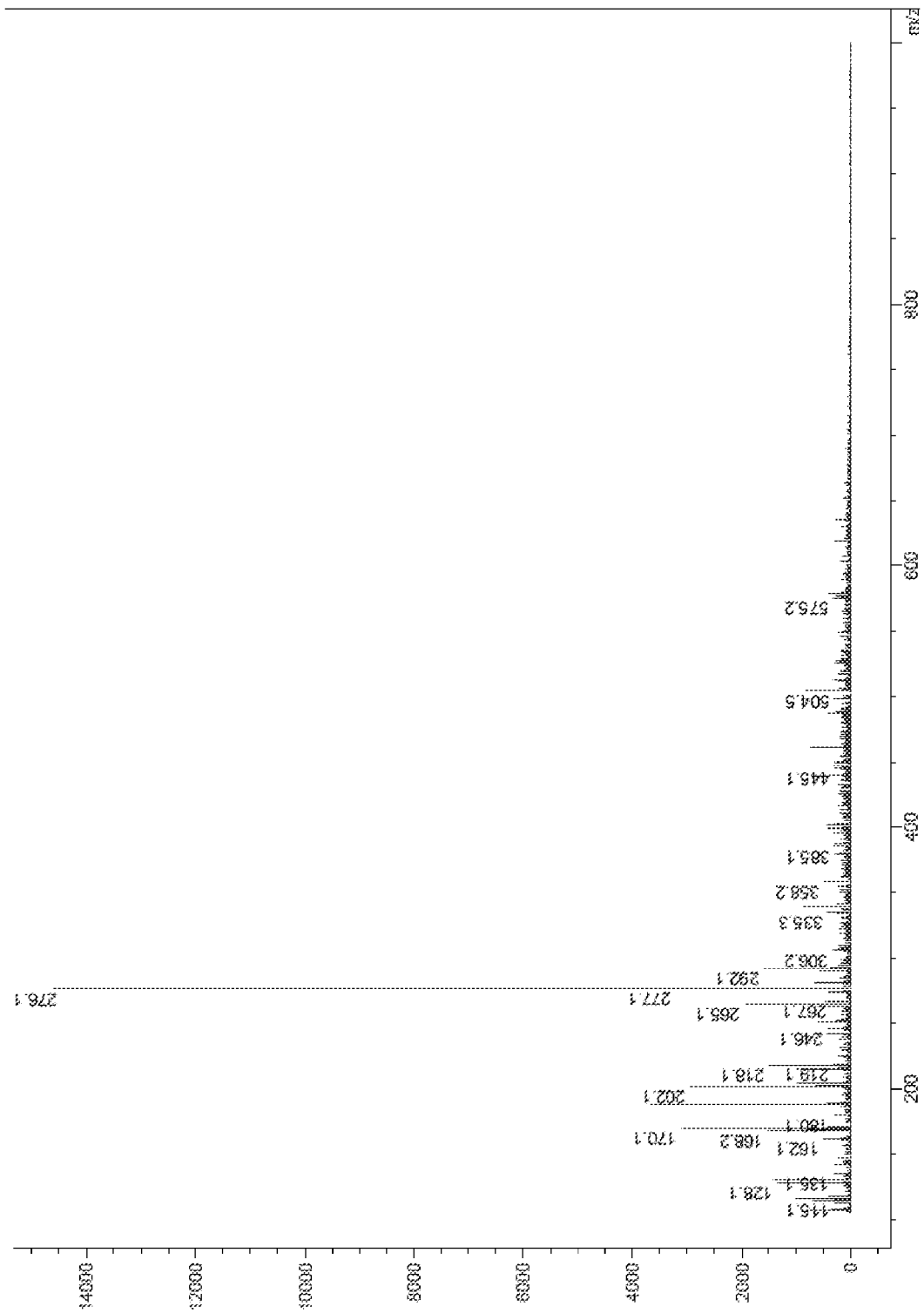
FIG. 4 shows mass spectrometry characterisation data for compound 225.

FIG. 4 shows spectrometric (mass spec) characterisation of compound 225.

Example 6—Compound 226

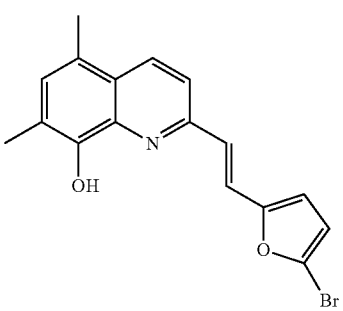

(Compound #226)

(E)-2-(2-(5-bromofuran-2-yl)vinyl)-5,7-dimethylquinolin-8-ol

Figure 5A:
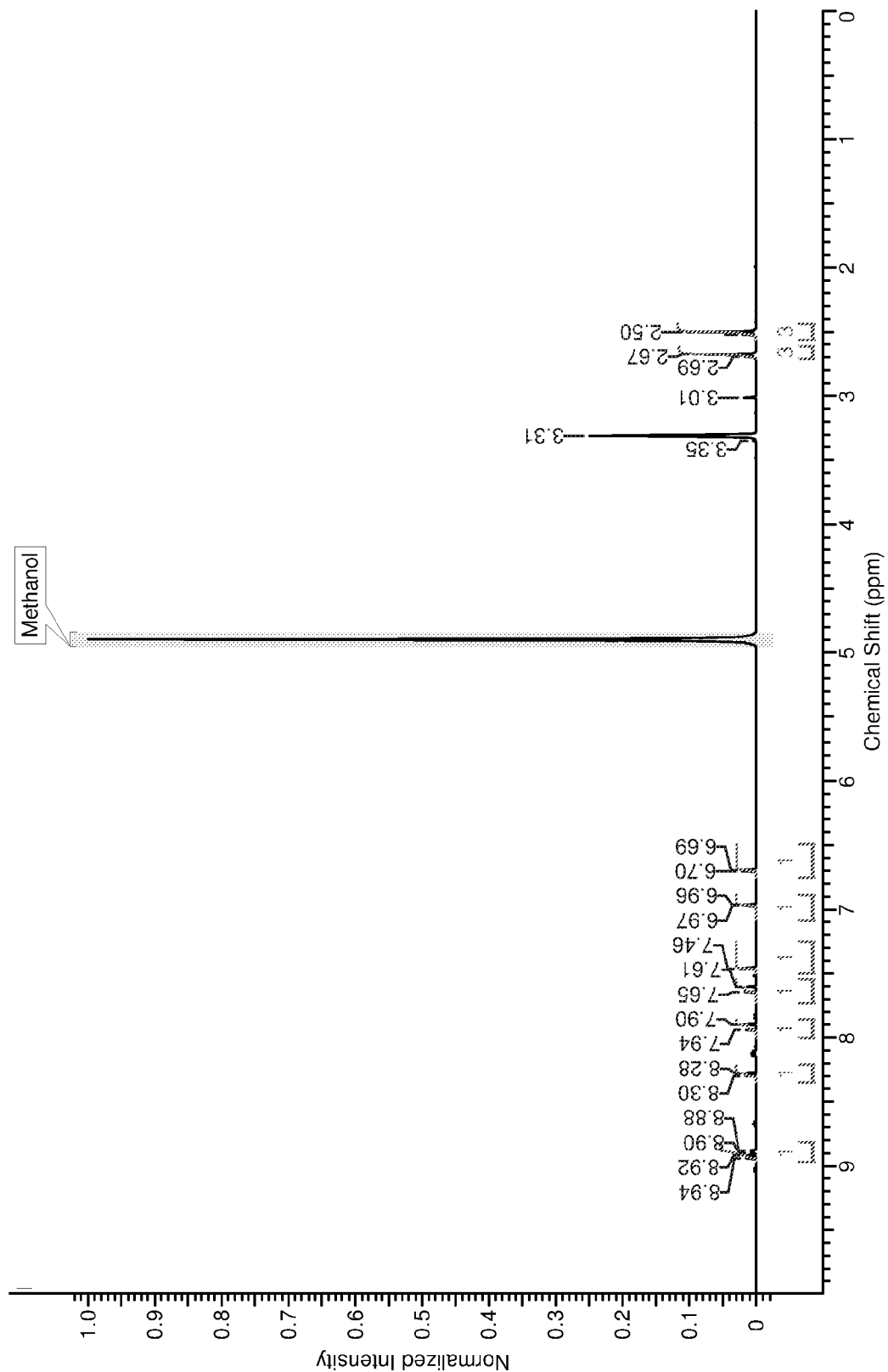
FIG. 5 shows the a) $^1$H NMR characterisation data and b) mass spectrometry characterisation data for compound 226.
Figure 5B:
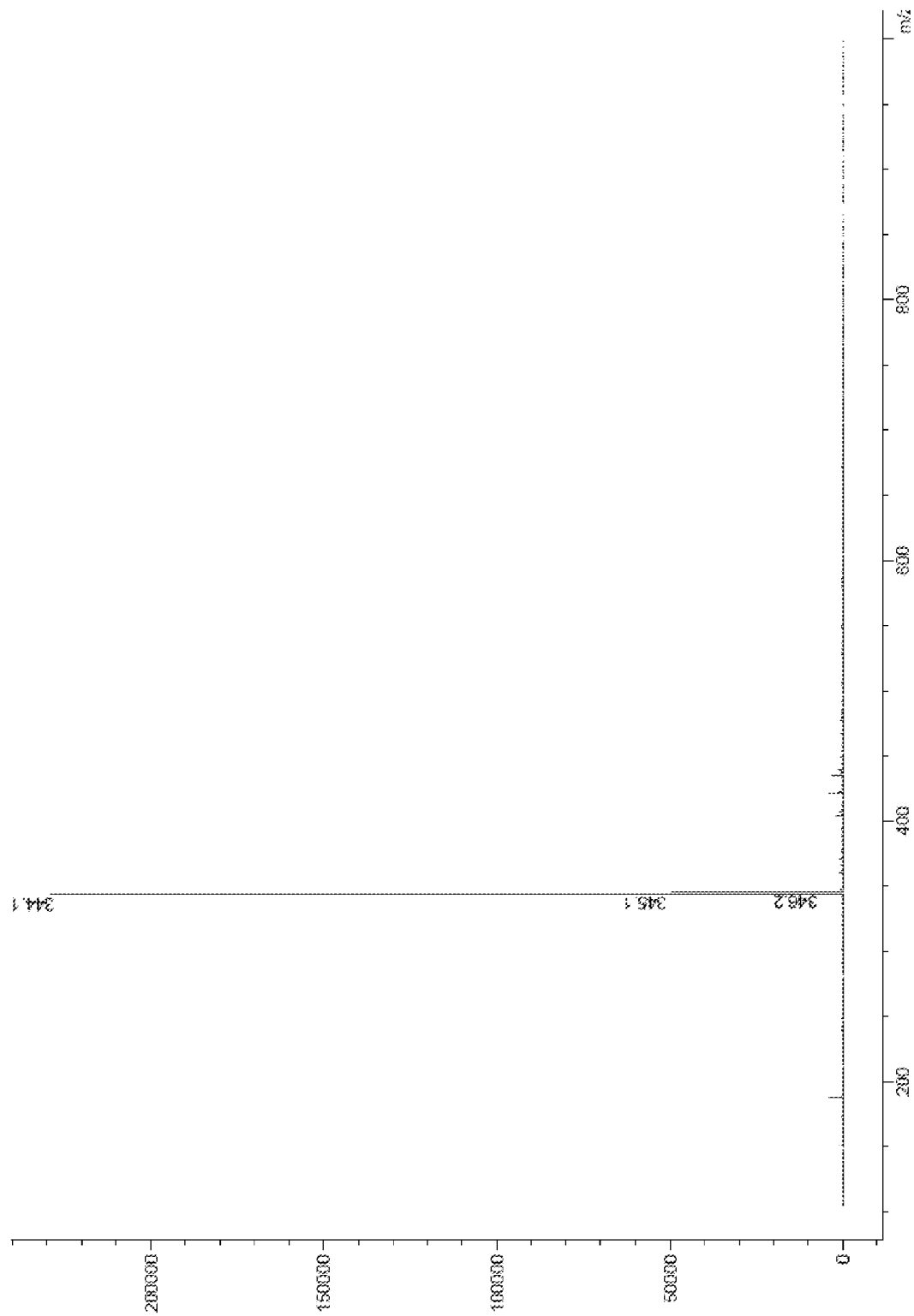

FIG. 5 shows spectroscopic ($^1$H NMR) and spectrometric (mass spec) characterisation of compound 226.

Example 7—Compound 227

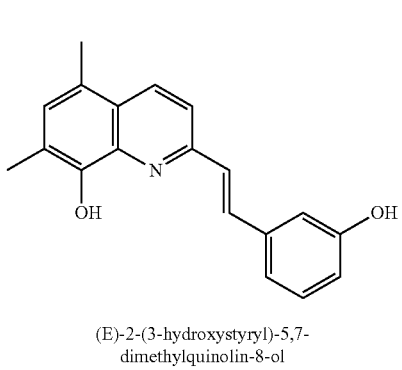

(Compound #227)

(E)-2-(3-hydroxystyryl)-5,7-dimethylquinolin-8-ol

Figure 6A:
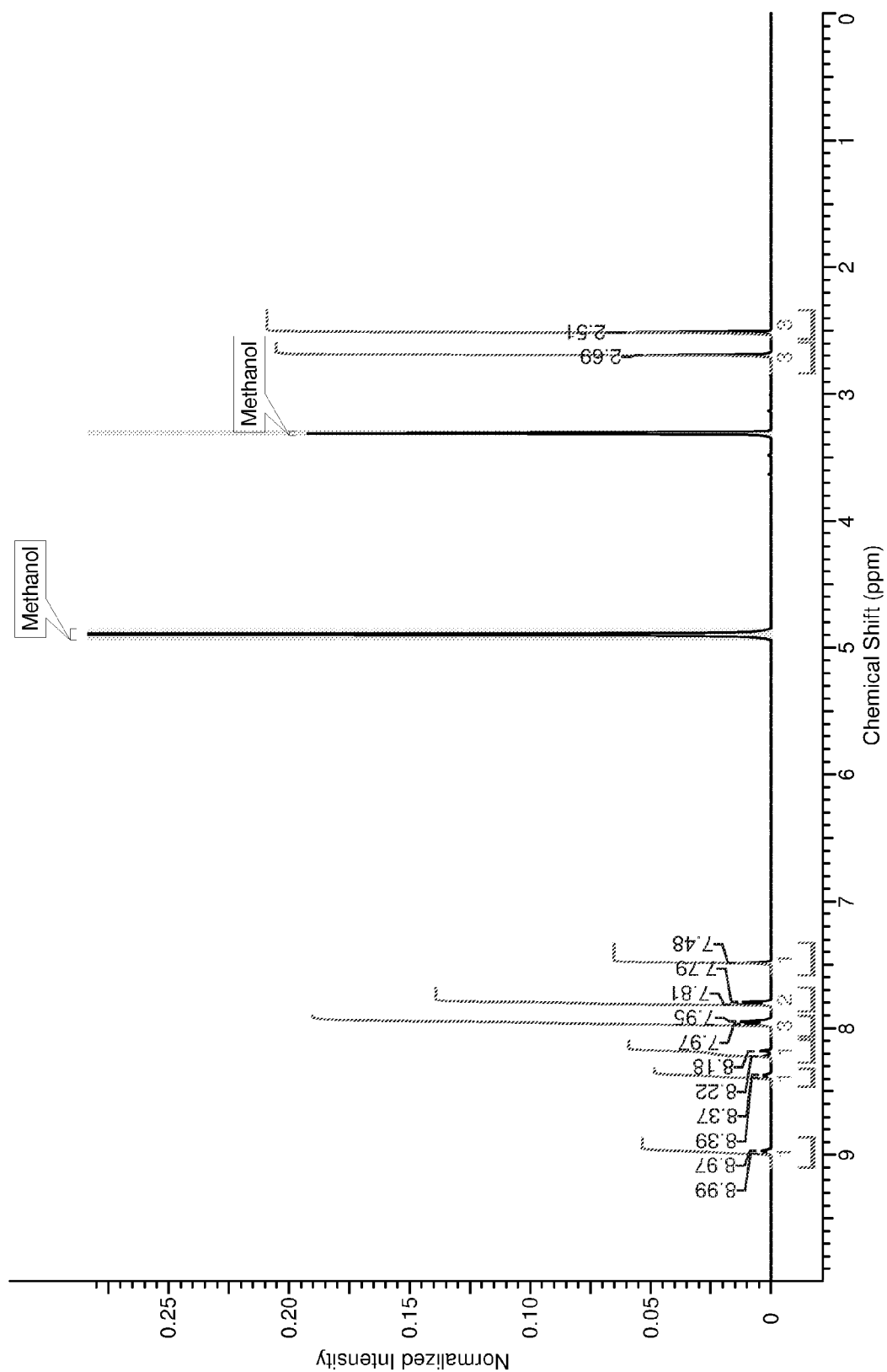
FIG. 6 the a) $^1$H NMR characterisation data and b) mass spectrometry characterisation data for compound 227.
Figure 6B:
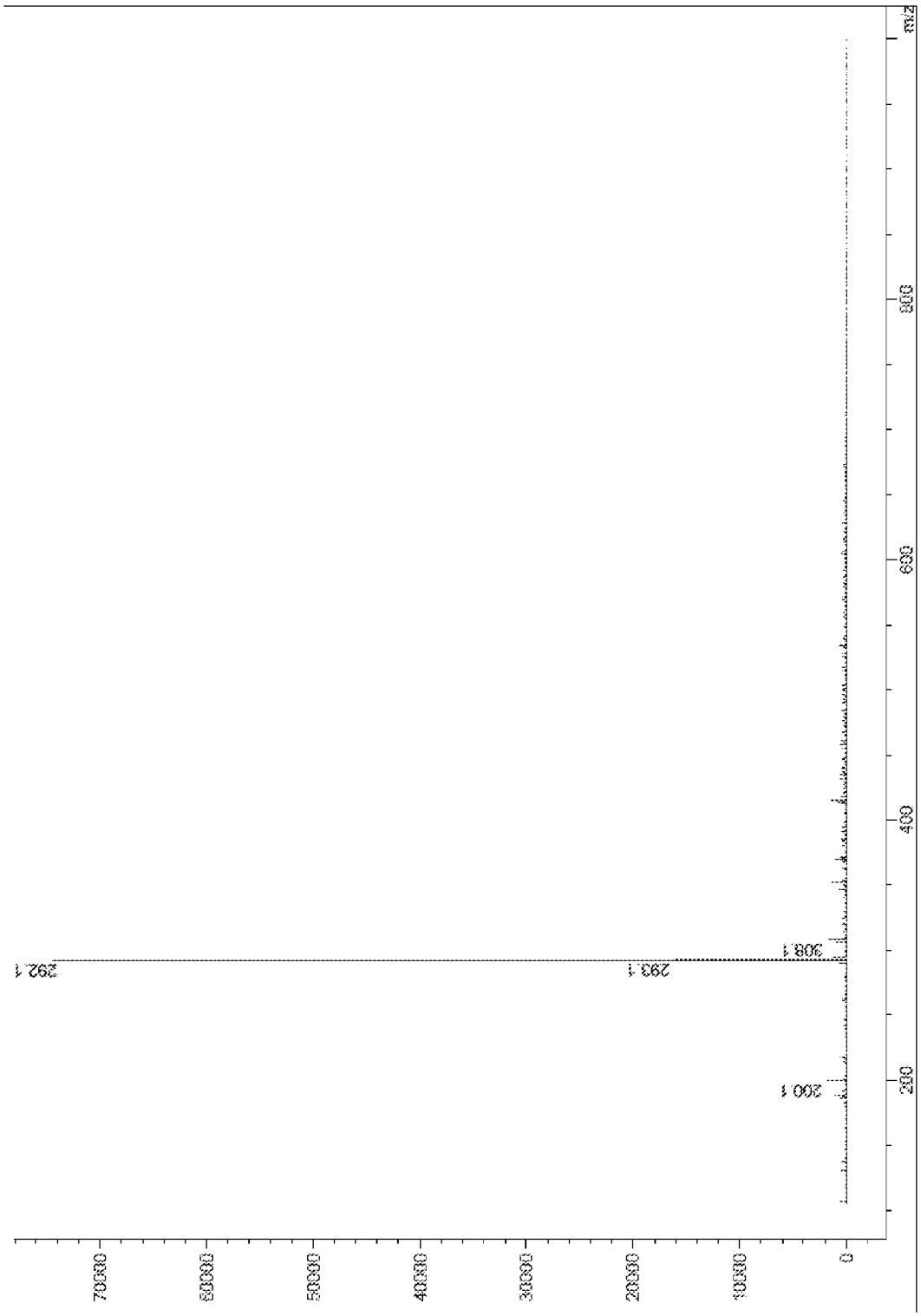

FIG. 6 shows spectroscopic ($^1$H NMR) and spectrometric (mass spec) characterisation of compound 227.

Example 8—Compound 229

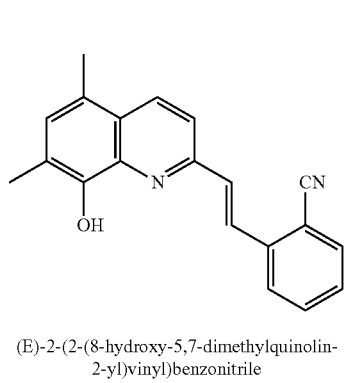

(Compound #229)

(E)-2-(2-(8-hydroxy-5,7-dimethylquinolin-2-yl)vinyl)benzonitrile

Figure 7A:
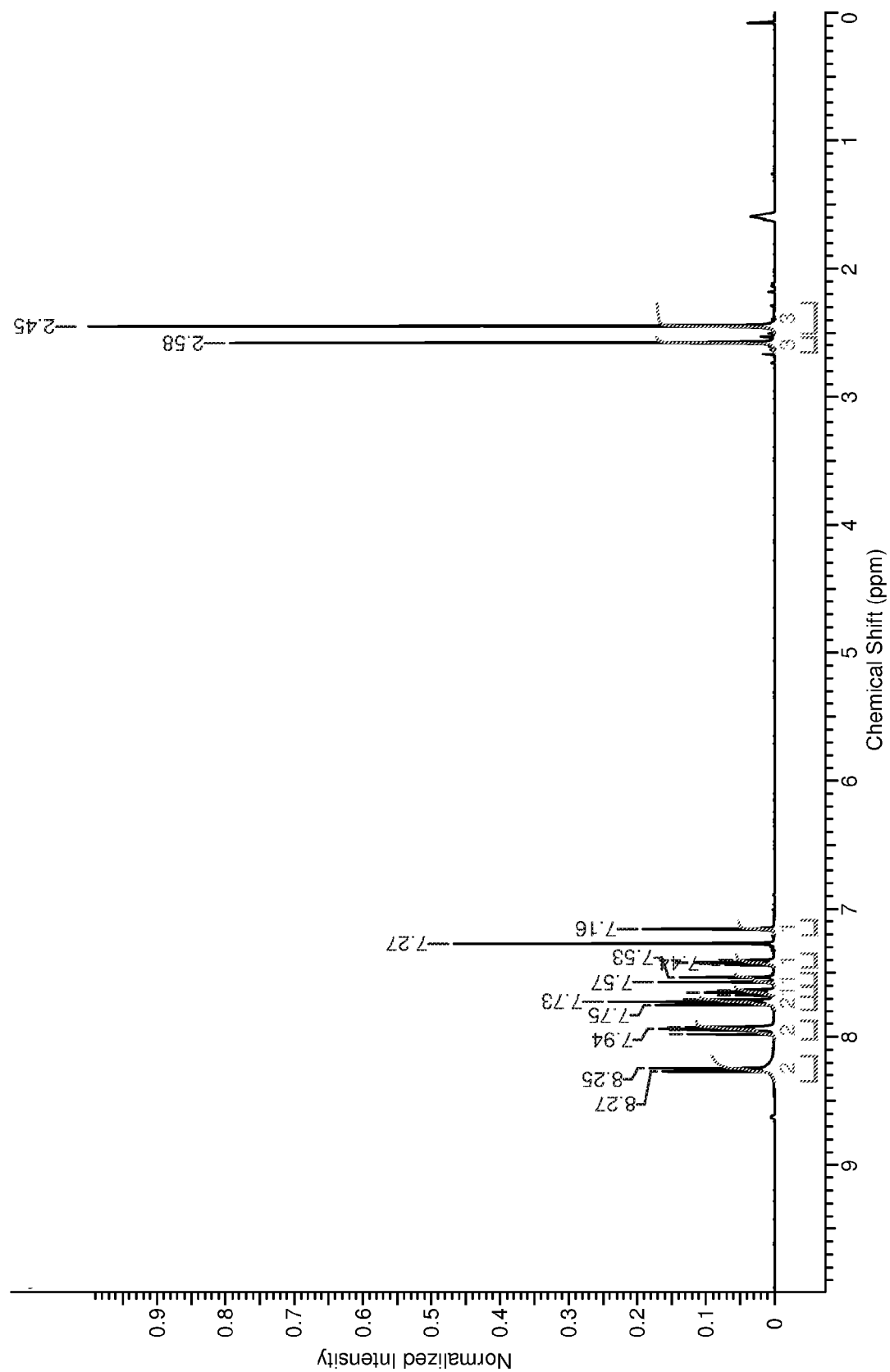
FIG. 7 shows the a) $^1$H NMR characterisation data and b) mass spectrometry characterisation data for compound 229.
Figure 7B:
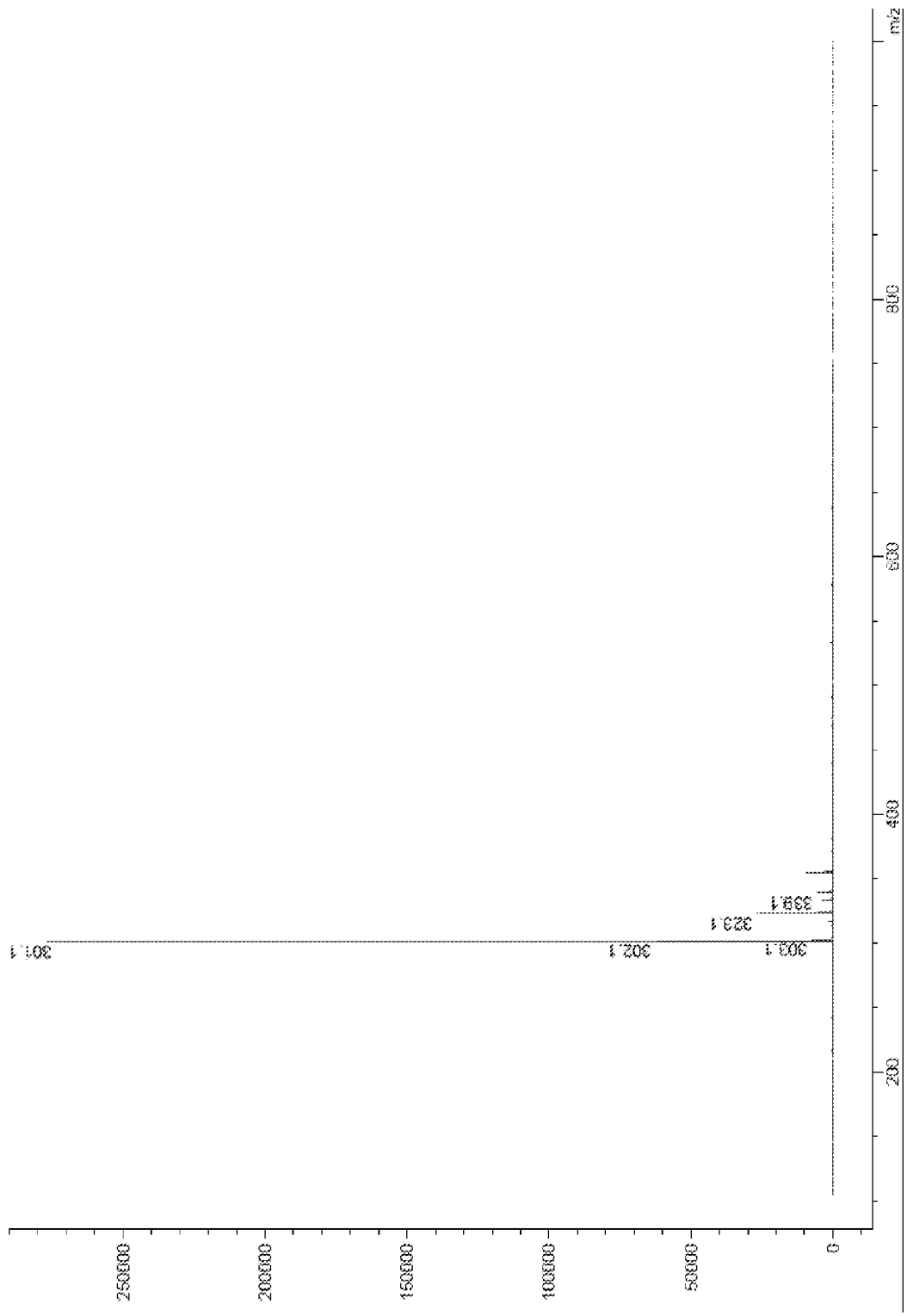

FIG. 7 shows spectroscopic ($^1$H NMR) and spectrometric (mass spec) characterisation of compound 229.

Example 9—Compound 234

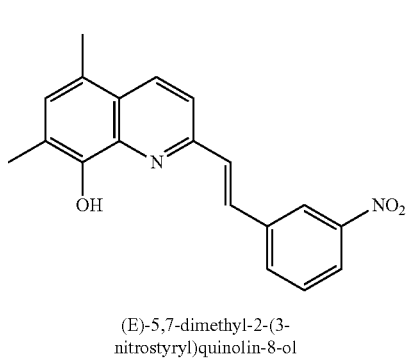

(Compound #234)

(E)-5,7-dimethyl-2-(3-nitrostyryl)quinolin-8-ol

Figure 8A:
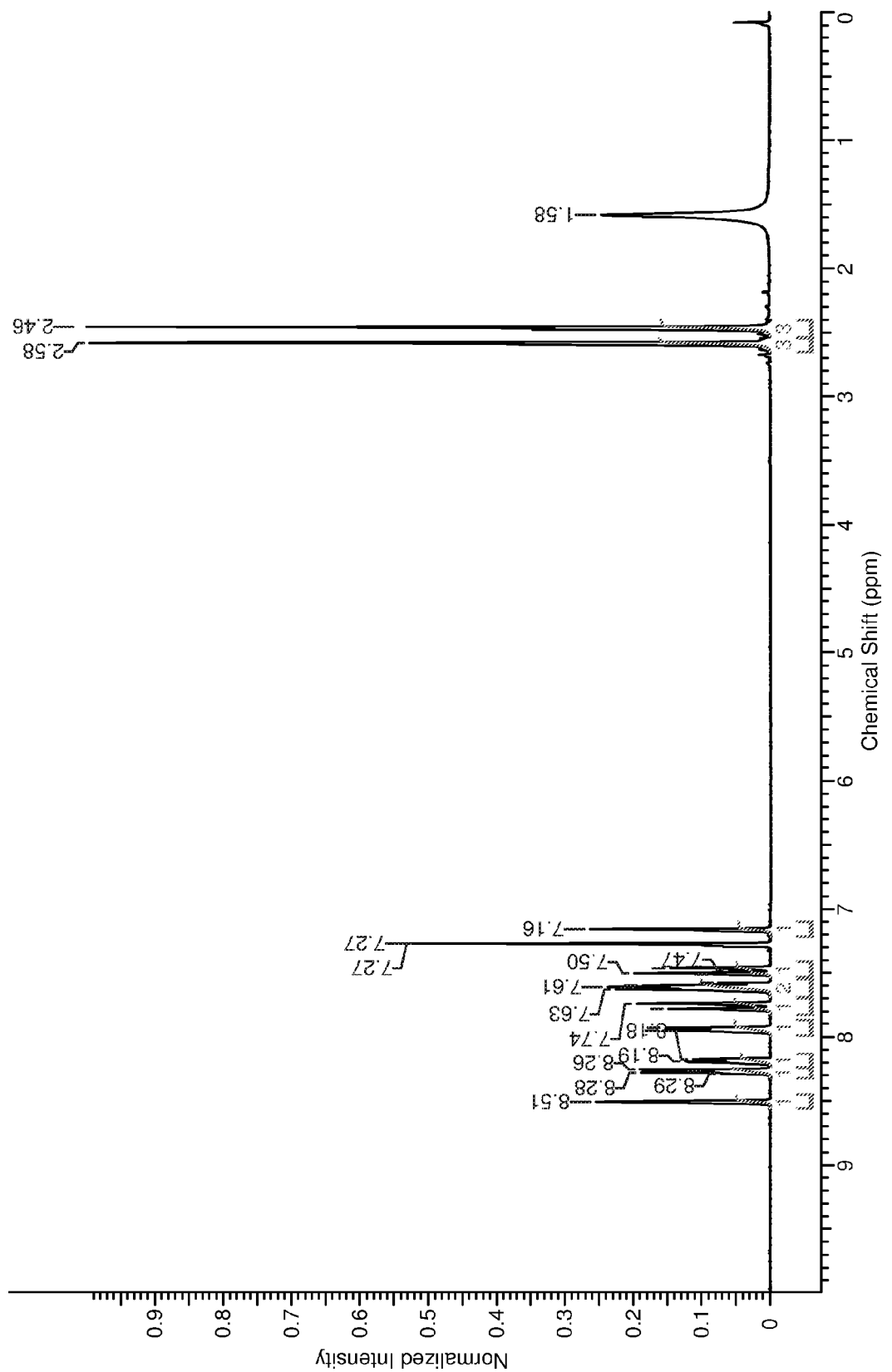
FIG. 8 shows the a) $^1$H NMR characterisation data and b) mass spectrometry characterisation data for compound 234.
Figure 8B:
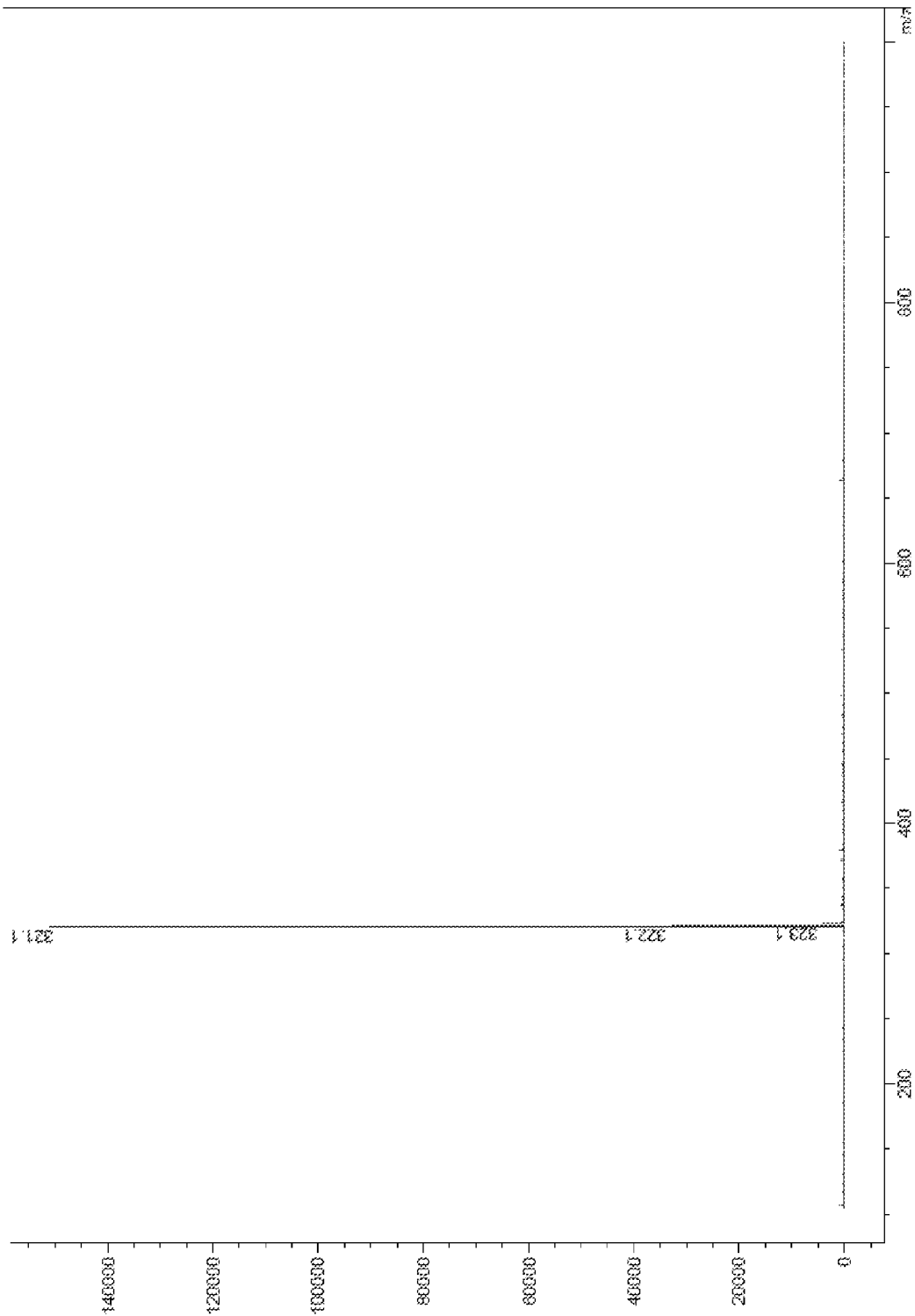

FIG. 8 shows spectroscopic ($^1$H NMR) and spectrometric (mass spec) characterisation of compound 234.

Example 10—Compound 236

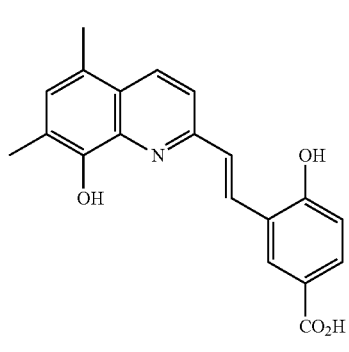

(Compound #236)

(E)-4-hydroxy-3-(2-(8-hydroxy-5,7-dimethylquinolin-2-yl)vinyl)benzoic acid

Figure 9:
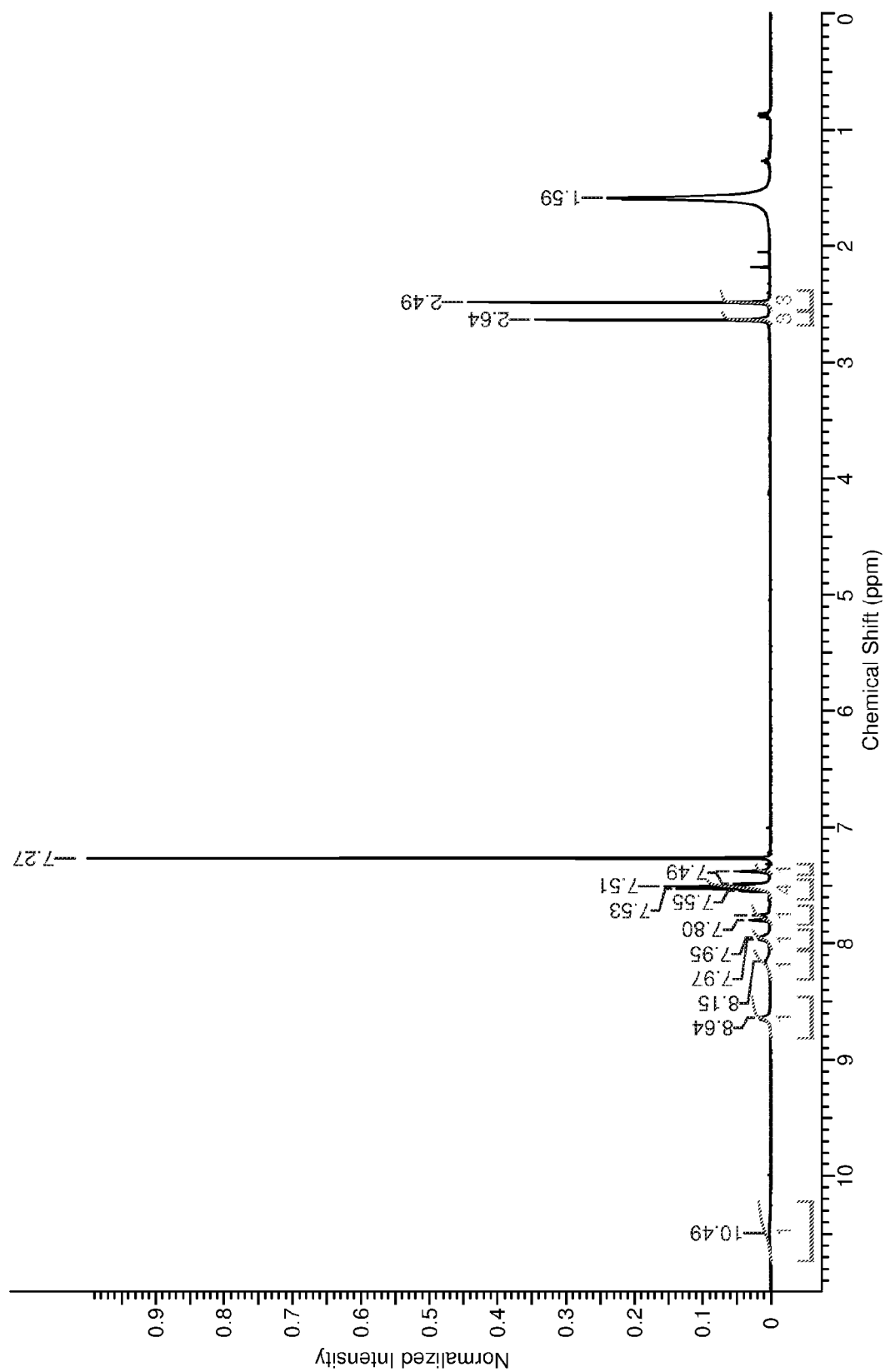
FIG. 9 shows the $^1$H NMR characterisation data for compound 236.

FIG. 9 shows spectroscopic ($^1$H NMR) characterisation of compound 236.

Example 11—Compound 238

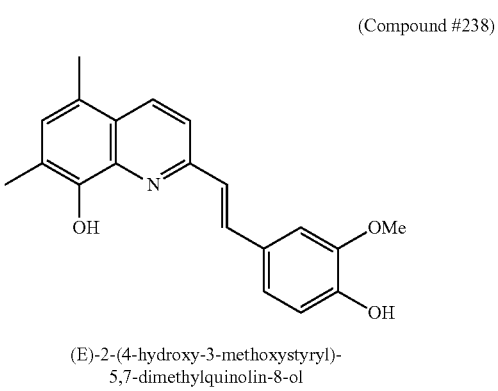 [SMILES: COc1cc(/C=C/c2ccc3c(C)cc(C)c(O)c3n2)ccc1O]

(Compound #238)

(E)-2-(4-hydroxy-3-methoxystyryl)-5,7-dimethylquinolin-8-ol

Figure 10A:
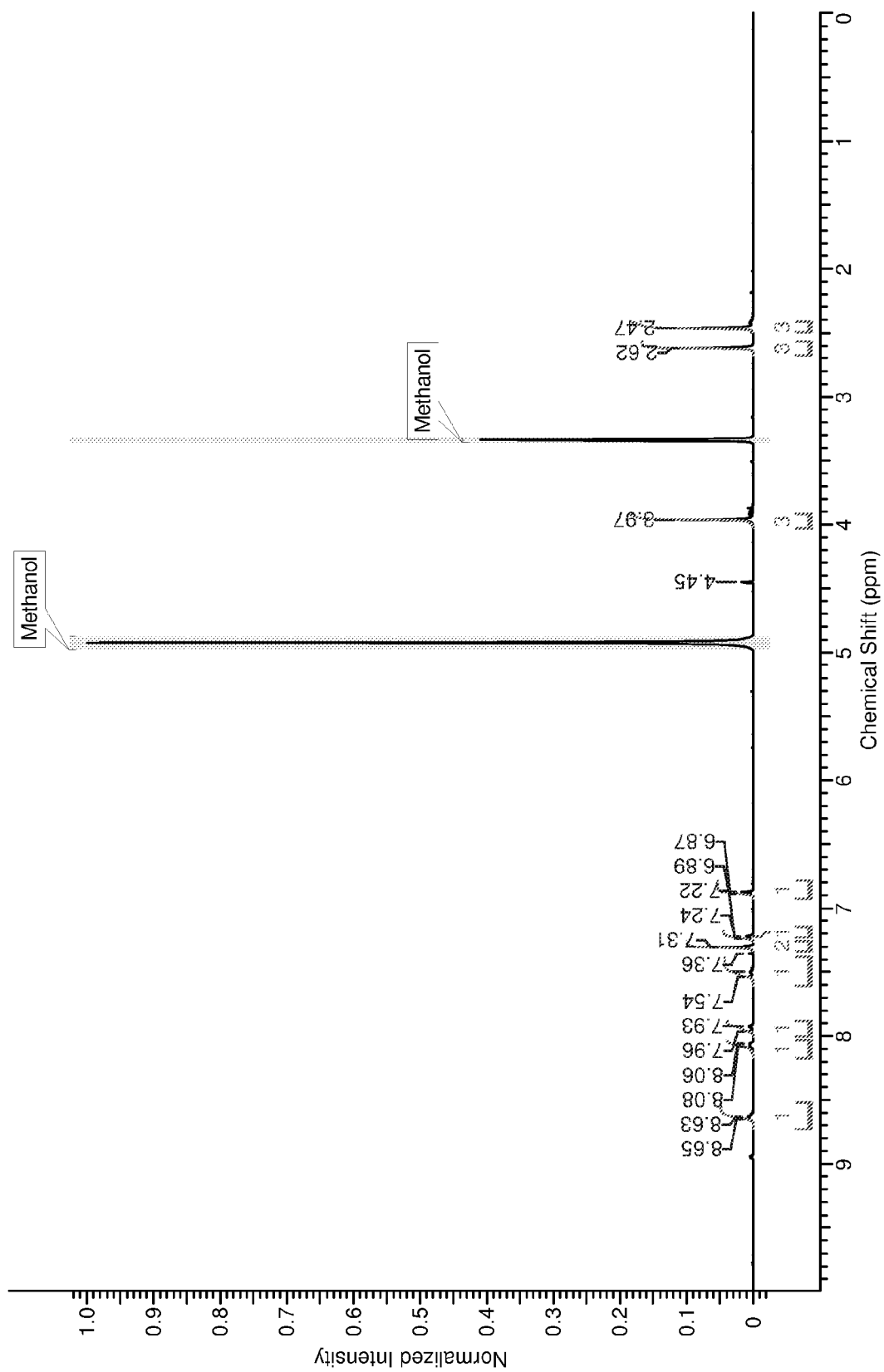
FIG. 10 shows the a) $^1$H NMR characterisation data and b) mass spectrometry characterisation data for compound 238.
Figure 10B:
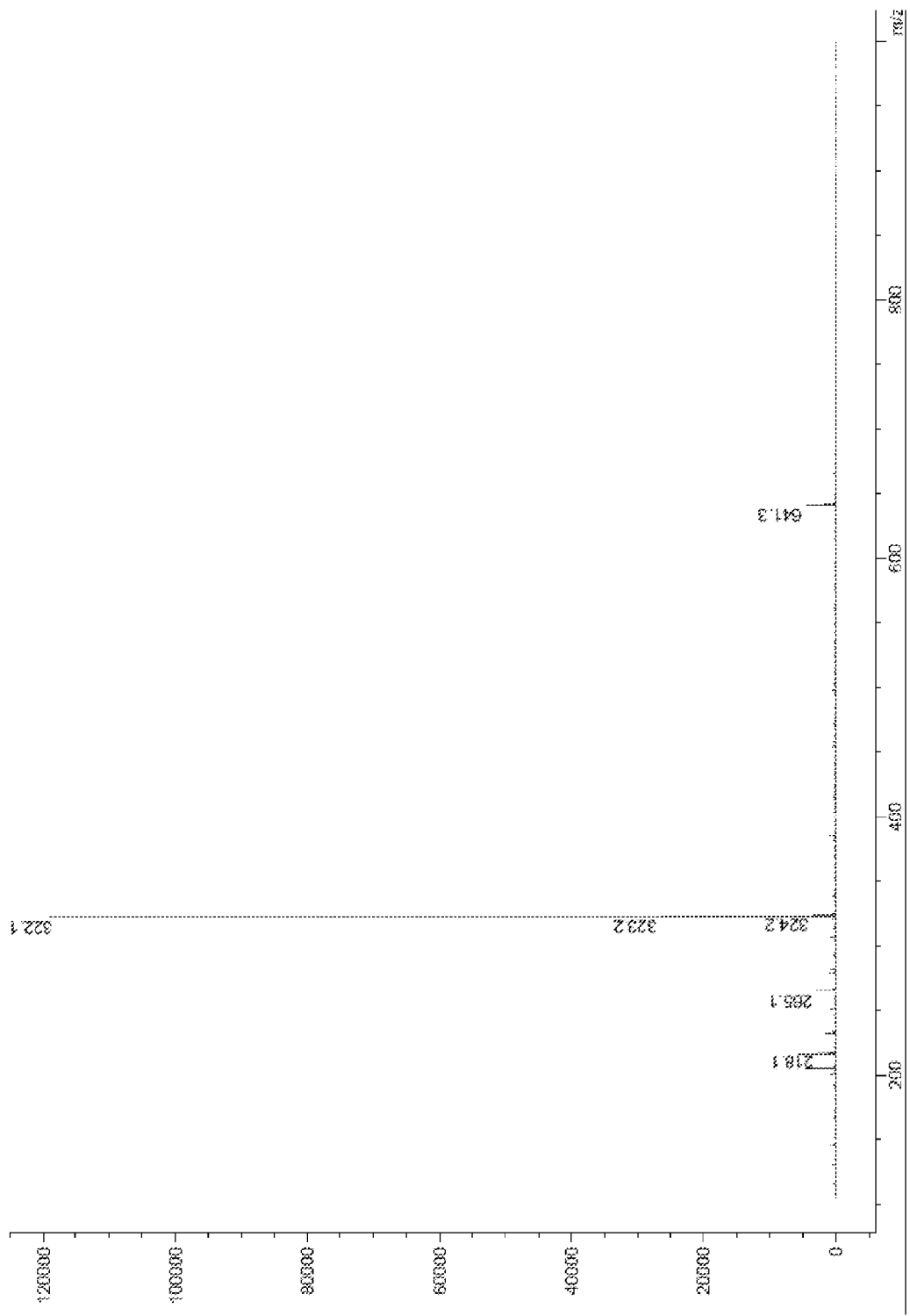
Figure 11:
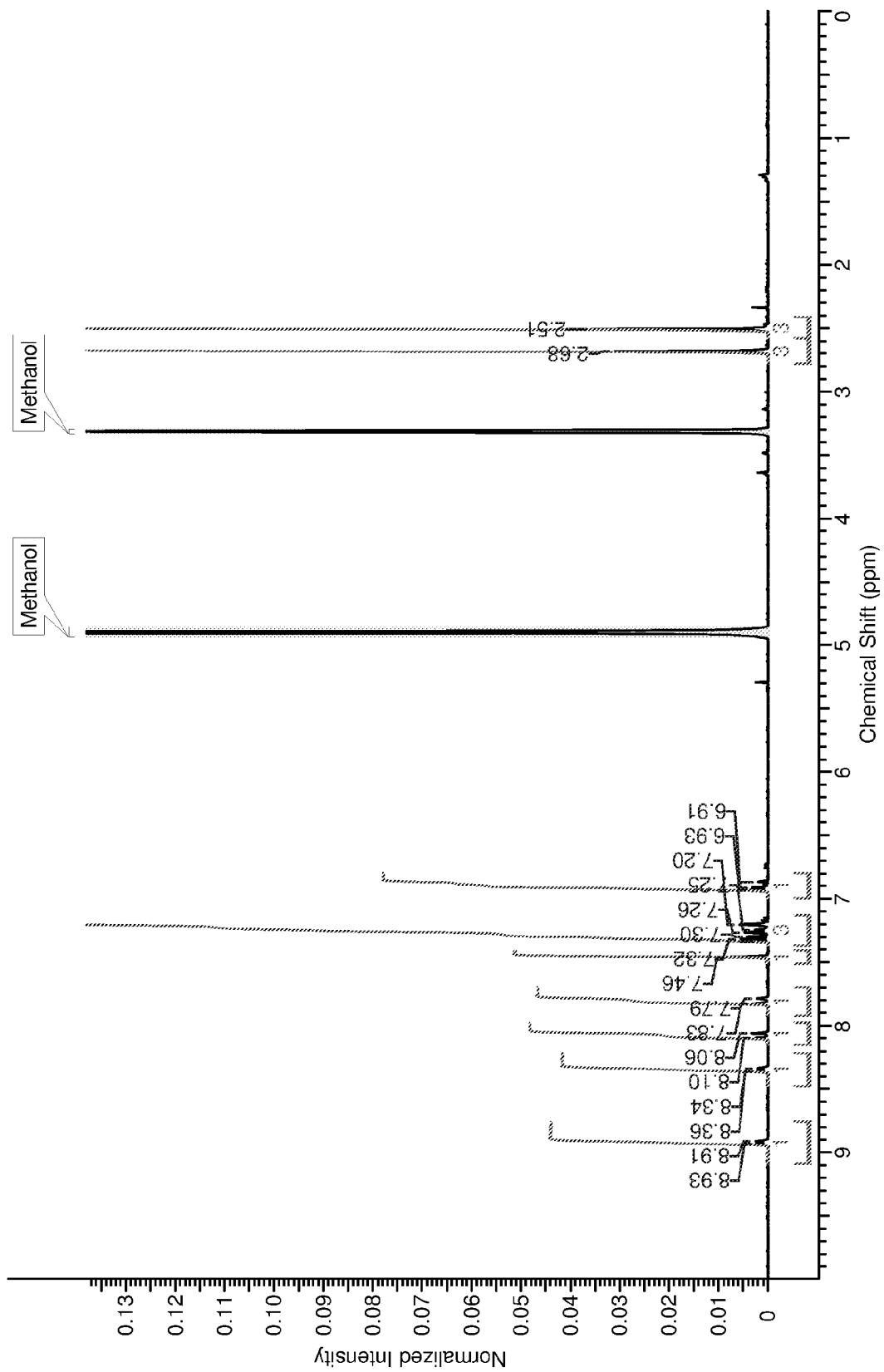
FIG. 11 shows the $^1$H NMR characterisation data for compound 239.

FIG. 10 shows spectroscopic ($^1$H NMR) and spectrometric (mass spec) characterisation of compound 238.

Example 12—Compound 239

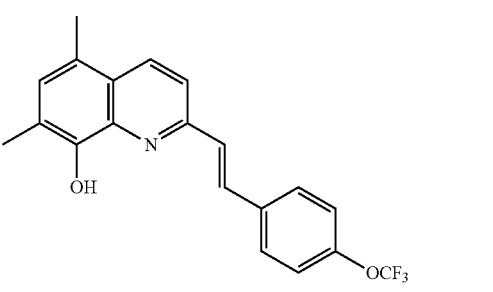

(Compound #239)

(E)-5,7-dimethyl-2-(4-(trifluoromethoxy)styryl)quinoline-8-ol

Example 13—Compound 241

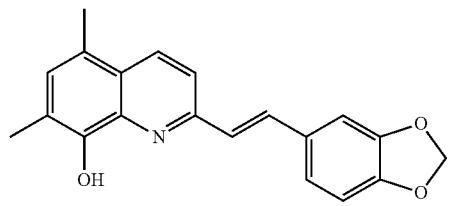

(Compound #241)

(E)-2-(2-(benzo[d][1,3]dioxol-5-yl)vinyl)-
5,7-dimethylquinolin-8-ol

Figure 12A:
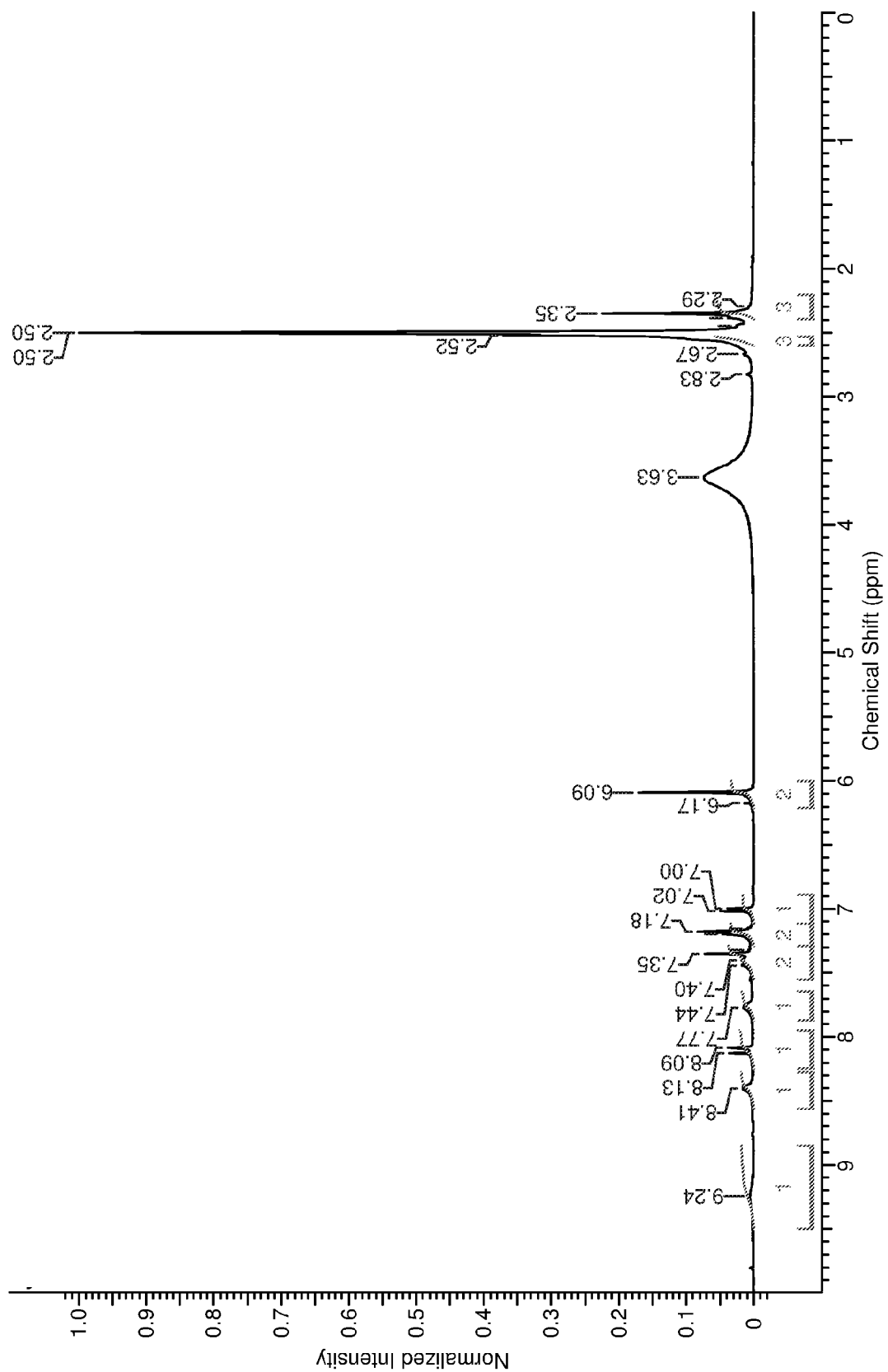
FIG. 12 shows the a) $^1$H NMR characterisation data and b) mass spectrometry characterisation data for compound 241.
Figure 12B:
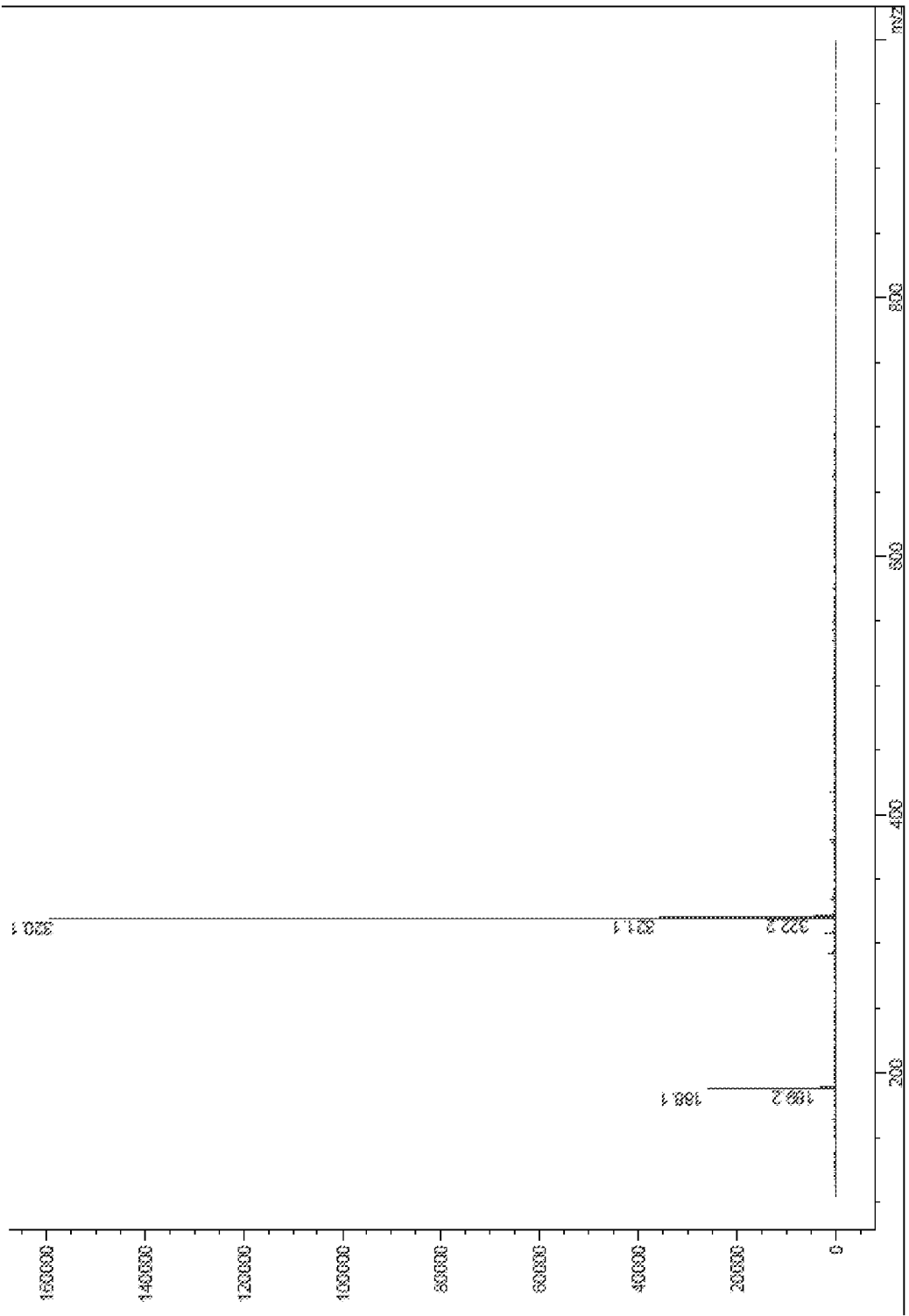

FIG. 12 shows spectroscopic (¹H NMR) and spectrometric (mass spec) characterisation of compound 241.

Example 14—Compound 245

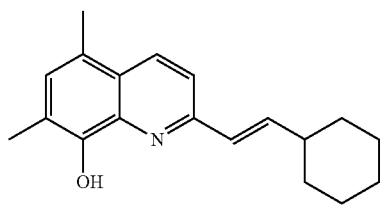

(Compound #245)

(E)-2-(2-(cyclohexylvinyl)-5,7-
dimethylquinolin-8-ol

Example 15—Compound 249

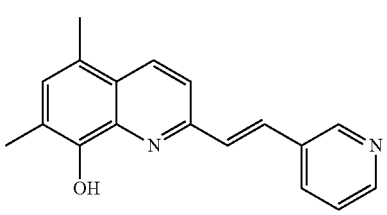

(Compound #249)

(E)-5,7-dimethyl-2-(2-(pyridin-3-
yl)vinyl)quinolin-8-ol

Figure 13A:
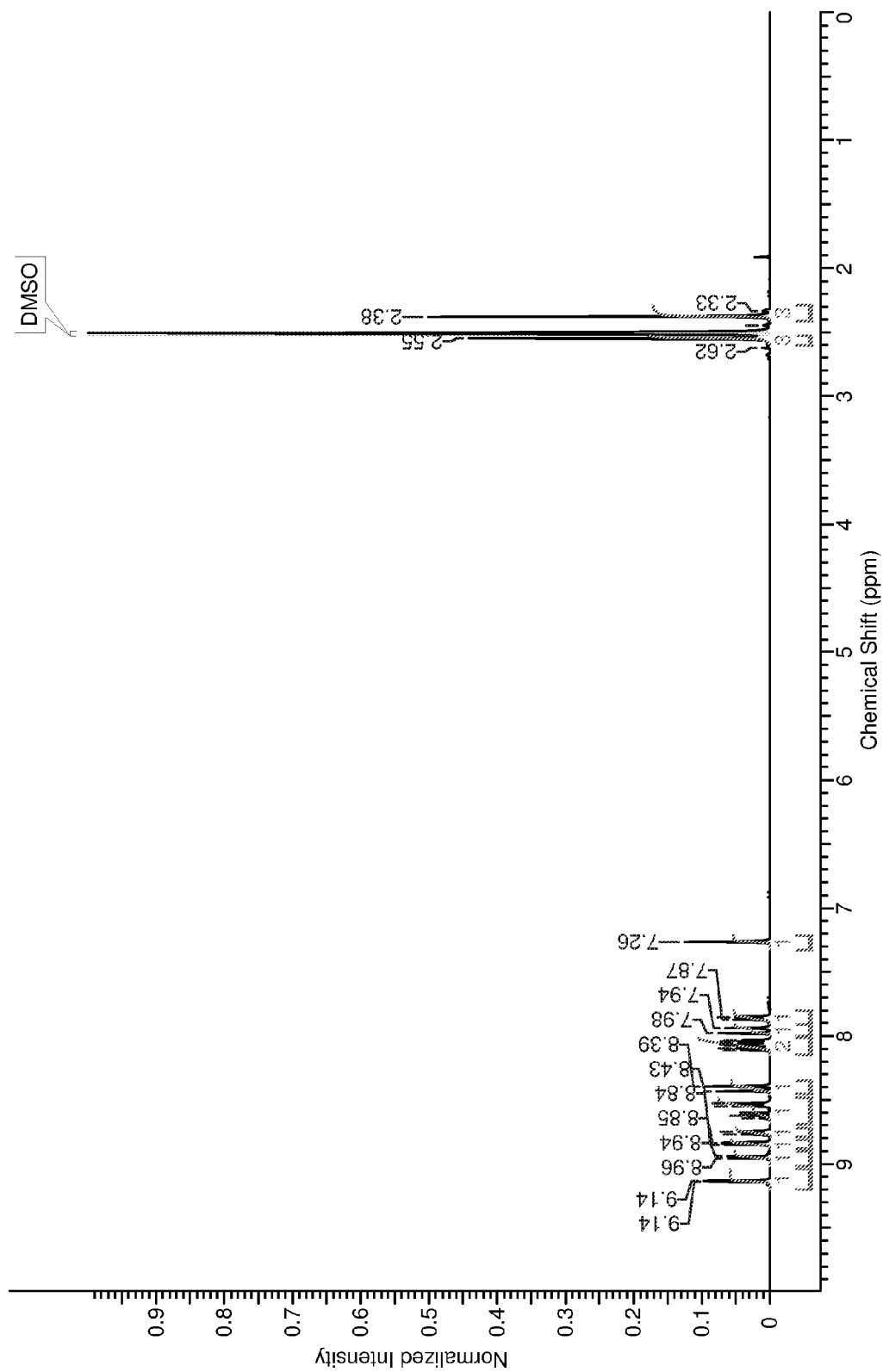
FIG. 13 the a) $^1$H NMR characterisation data and b) mass spectrometry characterisation data for compound 249.
Figure 13B:
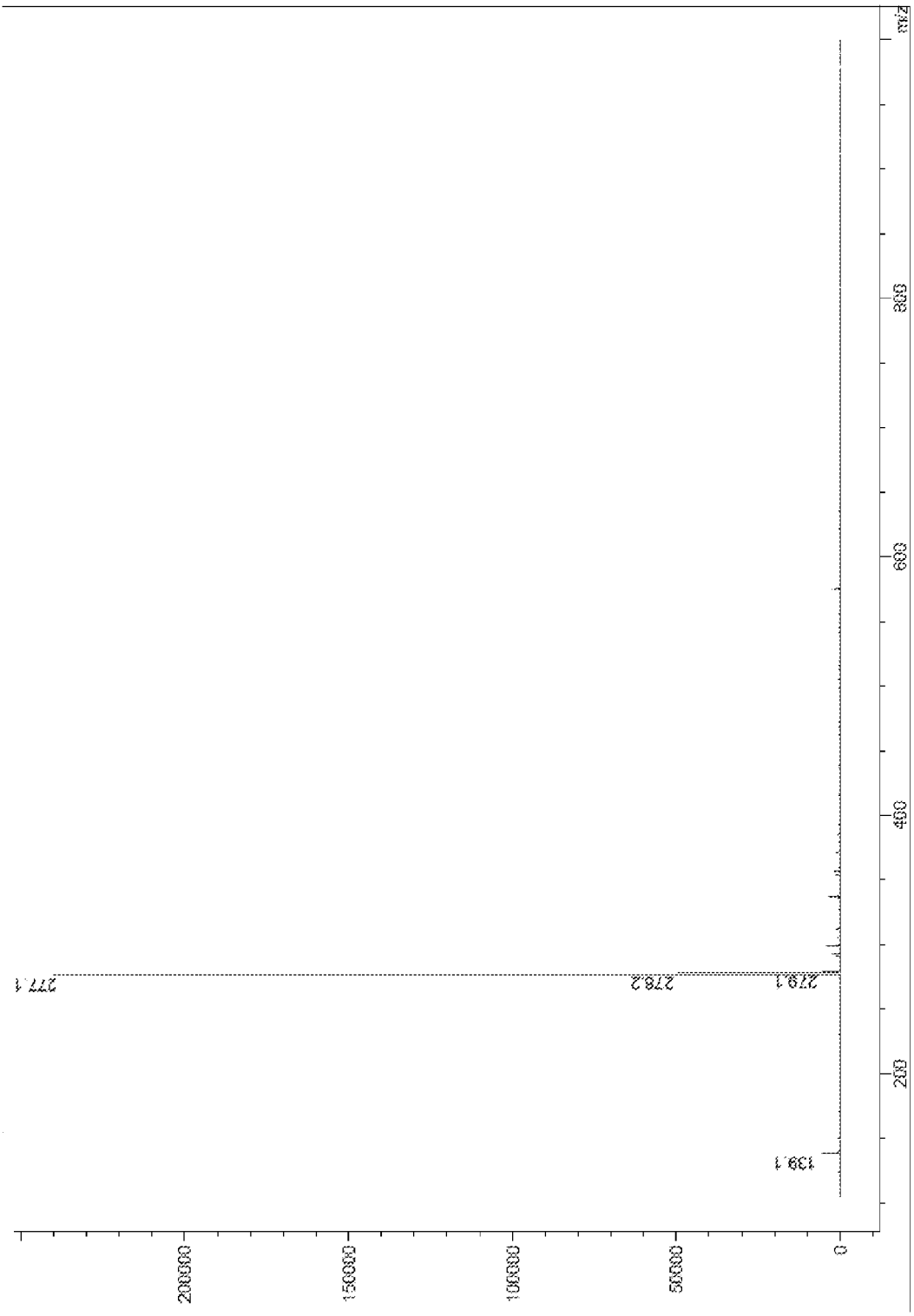

FIG. 13 shows spectroscopic (¹H NMR) and spectrometric (mass spec) characterisation of compound 249.

Example 16—Compound 251

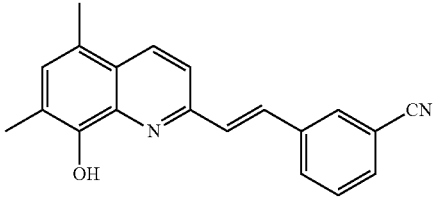

(Compound #251)

(E)-3-(2-(8-hydroxy-5,7-
dimethylquinolin-2-yl)vinyl)benzonitrile

Figure 14A:
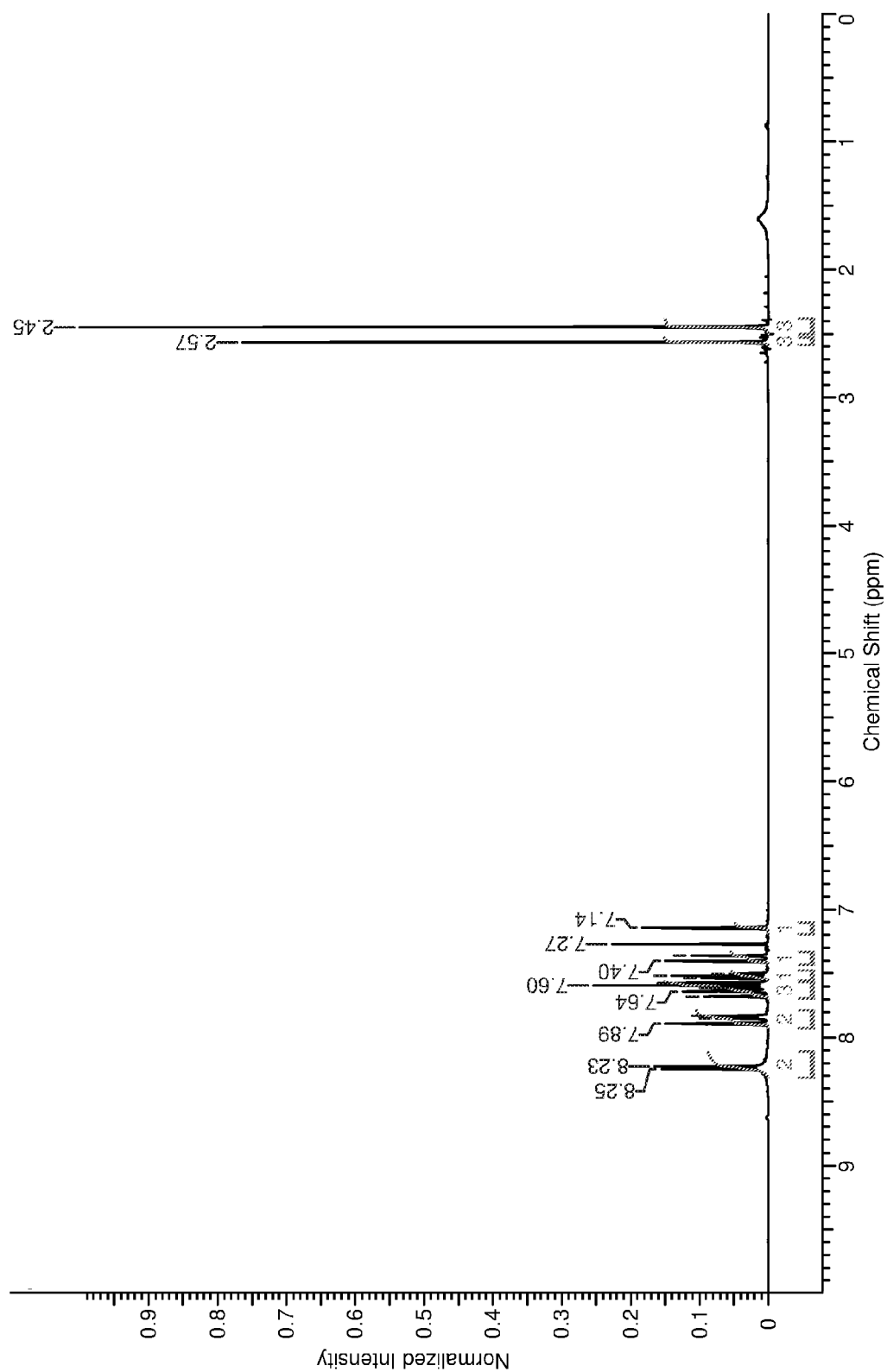
FIG. 14 shows the a) $^1$H NMR characterisation data and b) mass spectrometry characterisation data for compound 251.
Figure 14B:
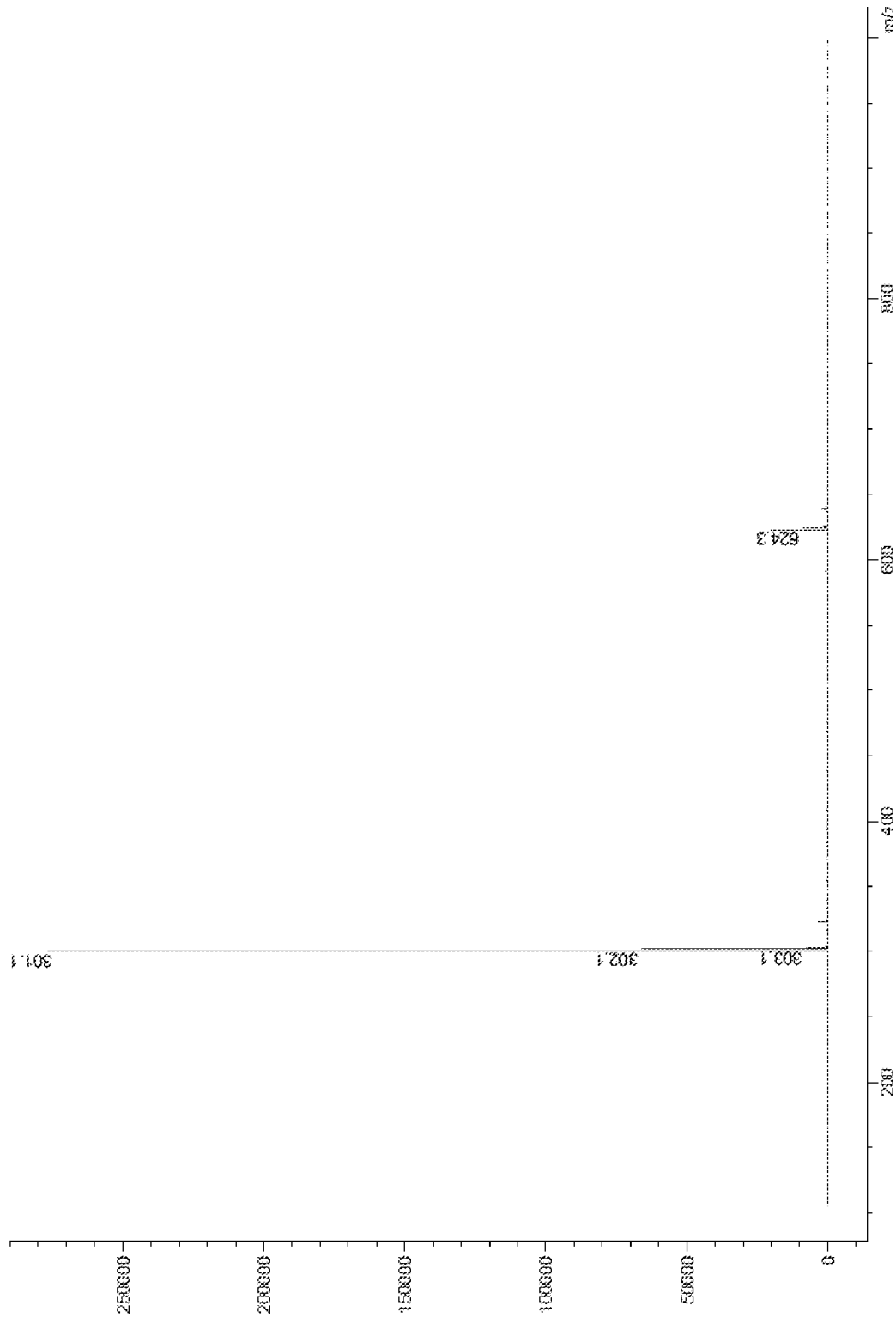

FIG. 14 shows spectroscopic (¹H NMR) and spectrometric (mass spec) characterisation of compound 251.

Example 17—Compound 252

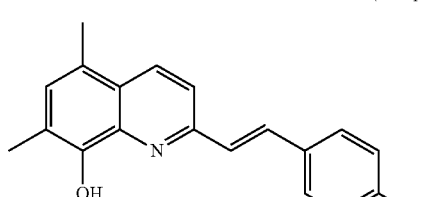

(Compound #252)

(E)-2-(4-bromostyryl)-5,7-
dimethylquinolin-8-ol

Example 18—Compound 311

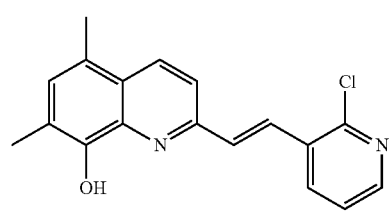

(Compound #311)

(E)-2-(2-(2-chloropyridin-3-yl)vinyl)-
5,7-dimethylquinolin-8-ol

Example 19—Compound 312

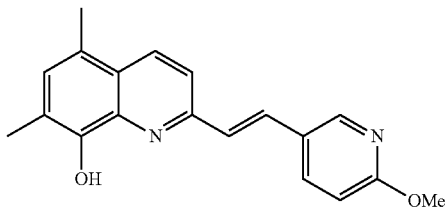

(E)-2-(2-(6-methoxypyridin-3-yl)vinyl)-
5,7-dimethylquinolin-8-ol

Figure 15:
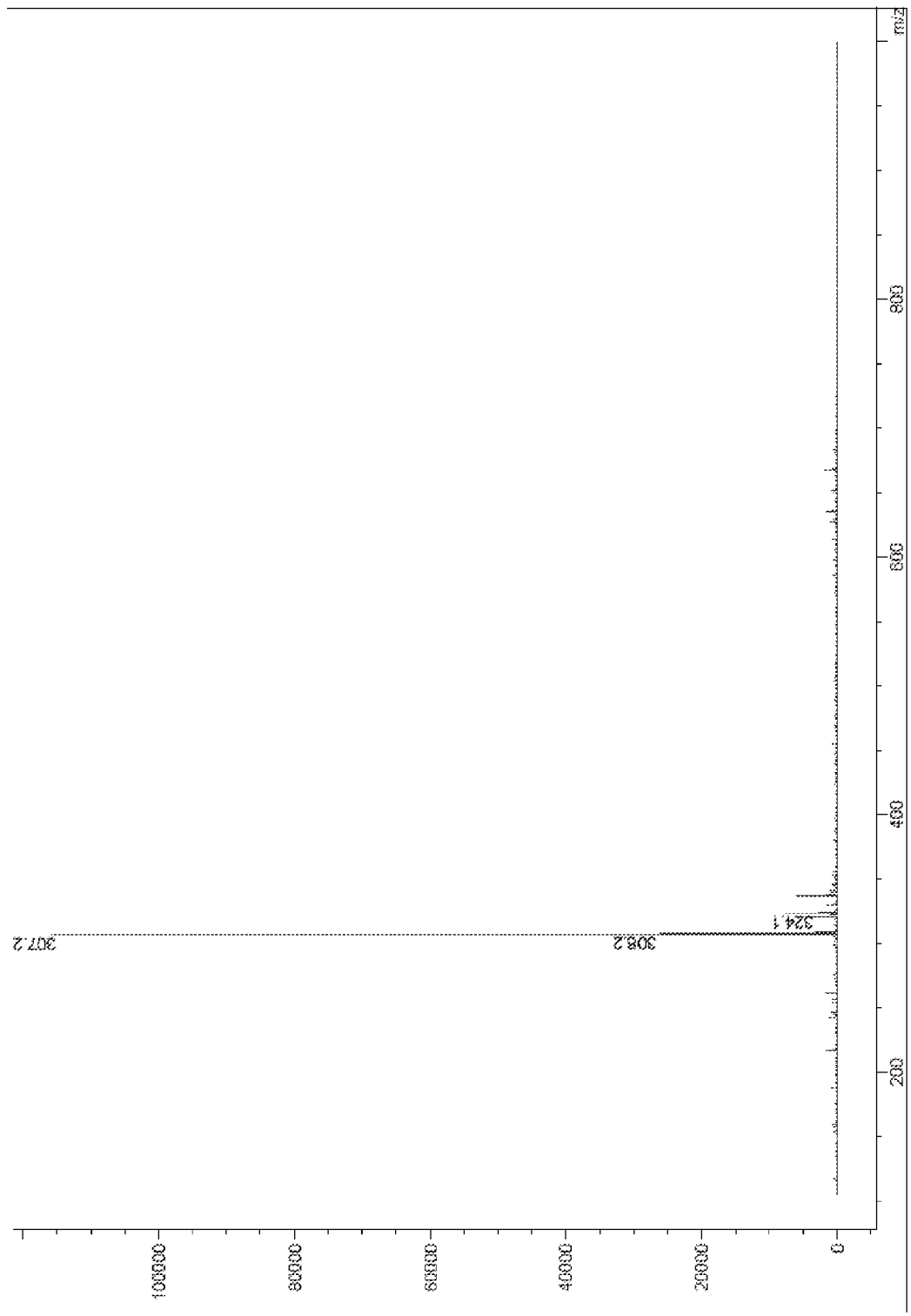
FIG. 15 shows the mass spectrometry characterisation data for compound 312.

FIG. 15 shows spectrometric (mass spec) characterisation of compound 312.

Example 20—Compound 313

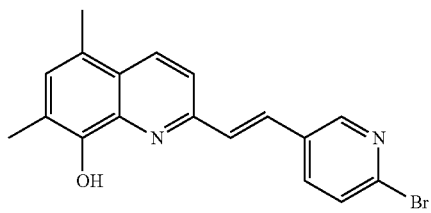

(E)-2-(2-(6-bromopyridin-3-
yl)vinyl)-5,7-dimethylquinolin-8-ol

Figure 16:
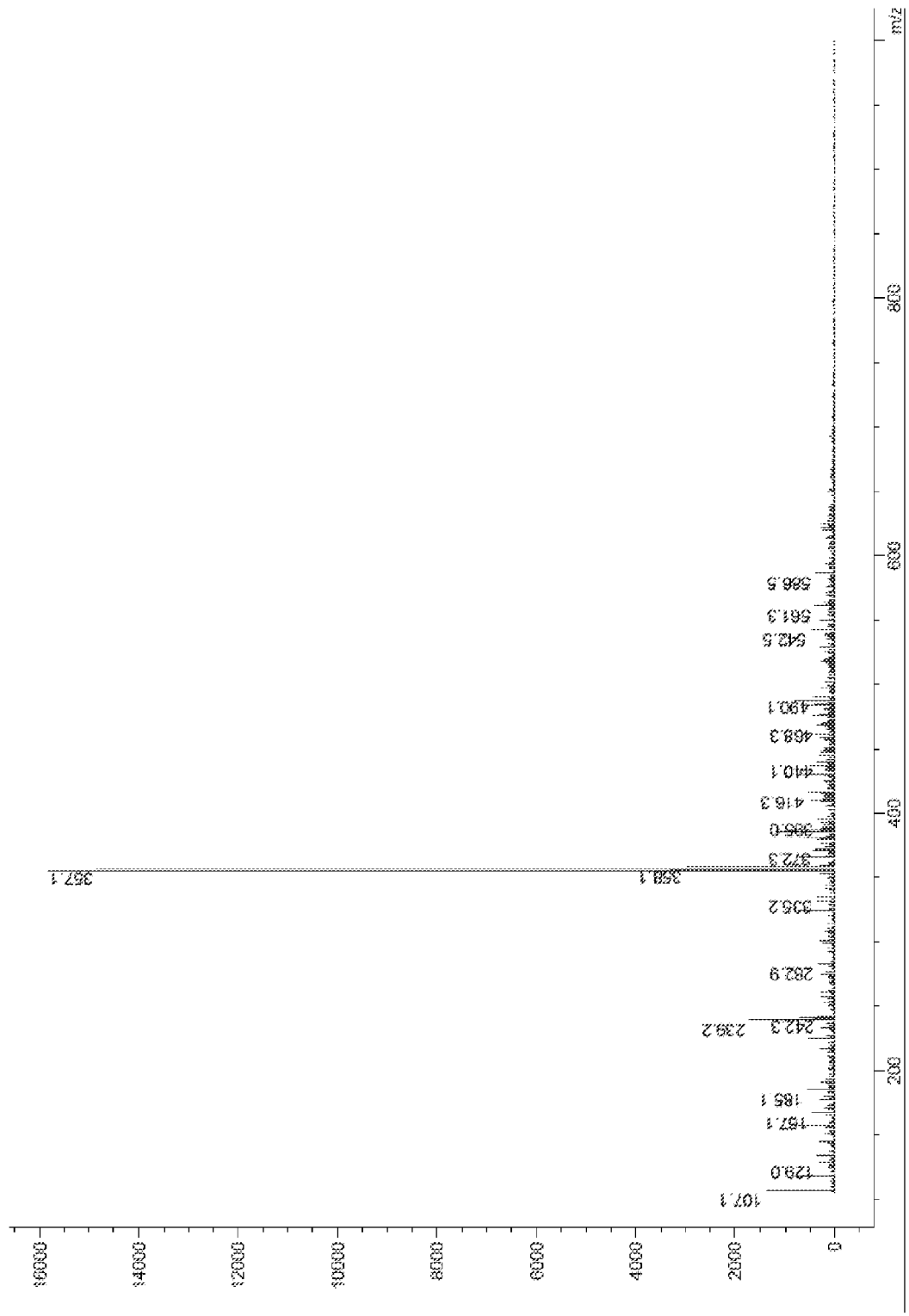
FIG. 16 shows the mass spectrometry characterisation data for compound 313.

FIG. 16 shows spectrometric (mass spec) characterisation of compound 313.

Example 21—Compound 314

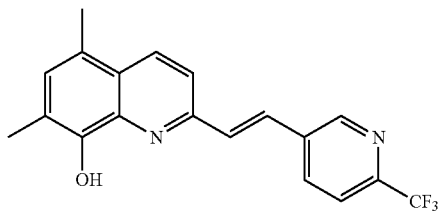

(E)-5,7-dimethyl-2-(2-(6-
(trifluoromethyl)pyridin-3-
yl)vinyl)-quinolin-8-ol

Figure 17A:
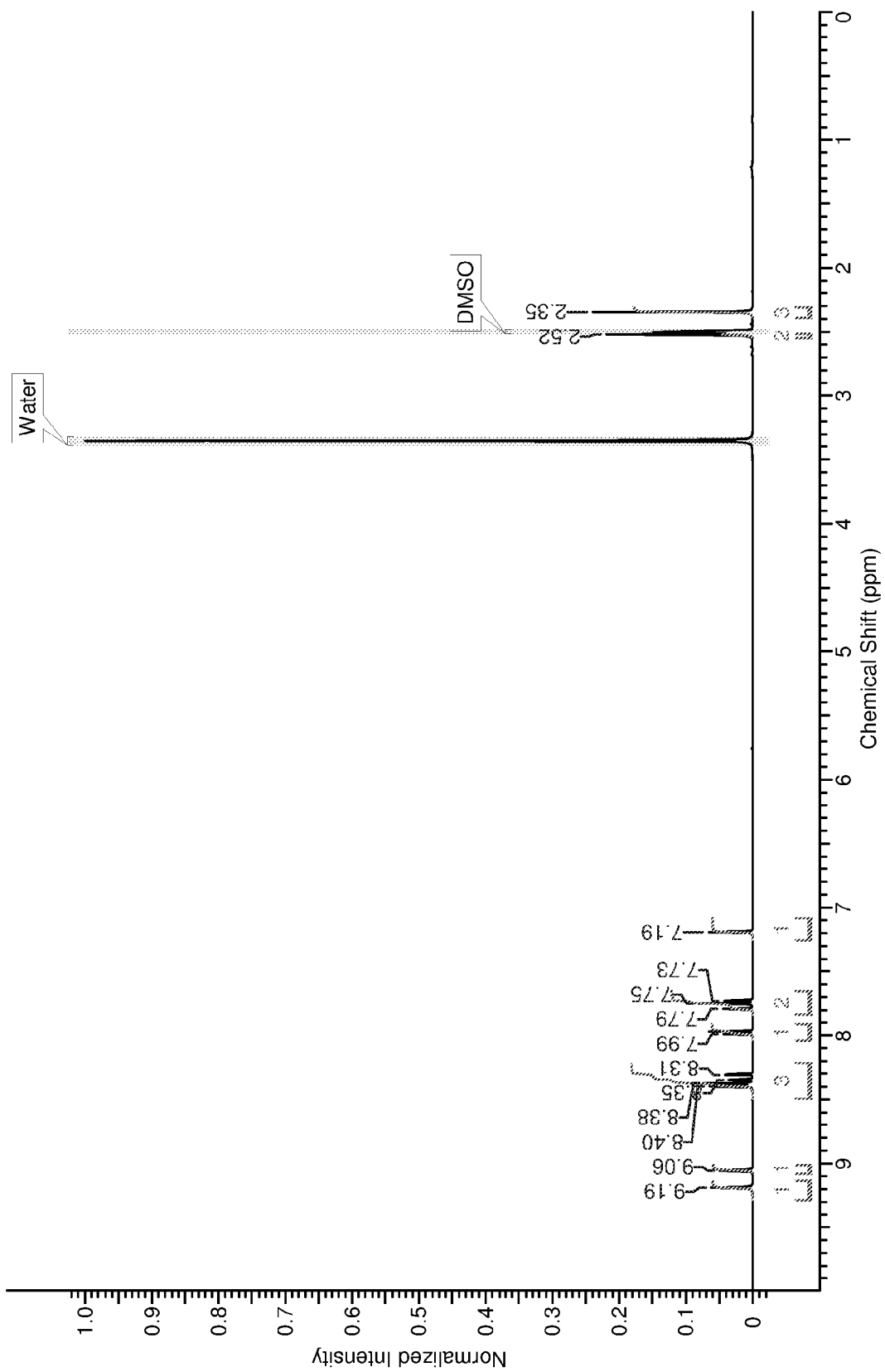
FIG. 17 shows the a) $^1$H NMR characterisation data and b) mass spectrometry characterisation data for compound 314.
Figure 17B:
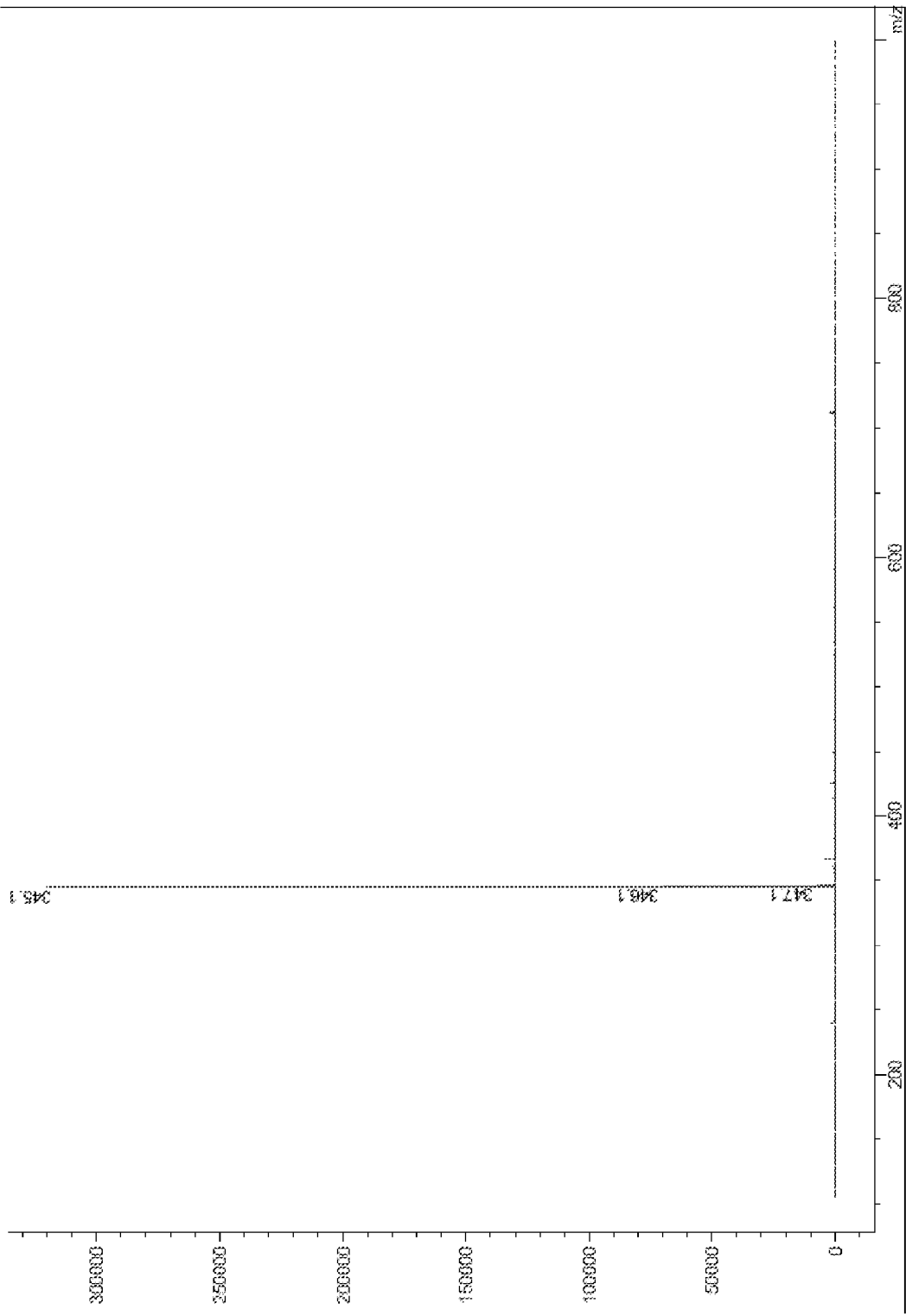

FIG. 17 shows spectroscopic ($^1$H NMR) and spectrometric (mass spec) characterisation of compound 314.

Example 22—Compound 315

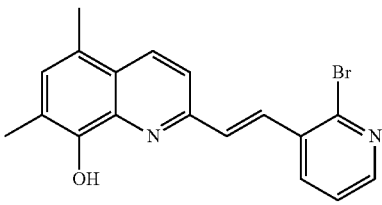

(E)-2-(2-(2-bromopyridin-3-yl)vinyl)-
5,7-dimethylquinolin-8-ol

Figure 18A:
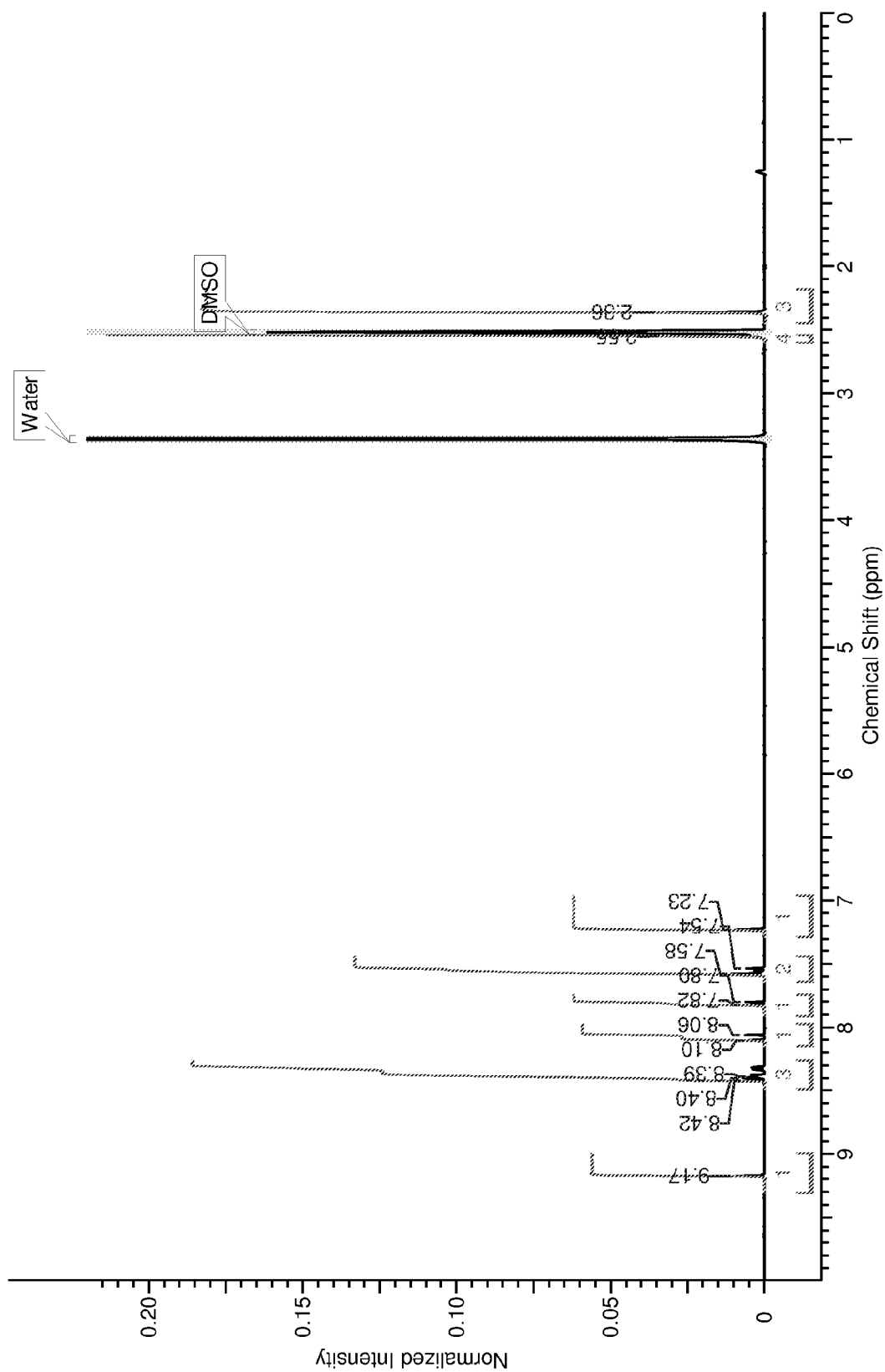
FIG. 18 shows the a) $^1$H NMR characterisation data and b) mass spectrometry characterisation data for compound 315.
Figure 18B:
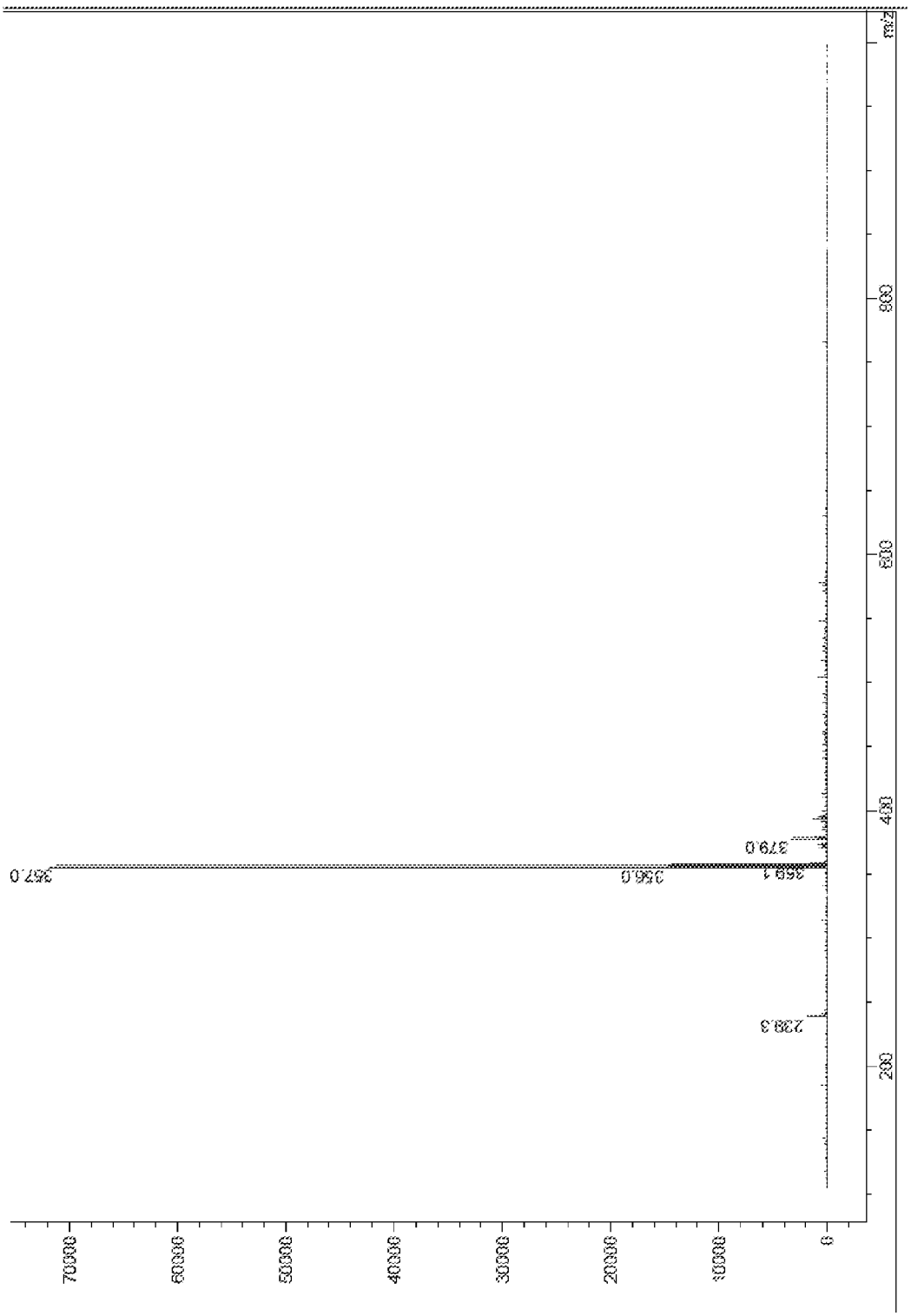

FIG. 18 shows spectroscopic ($^1$H NMR) and spectrometric (mass spec) characterisation of compound 315.

Example 23—Compound 316

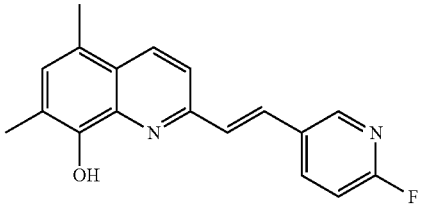

(E)-2-(2-(6-fluoropyridin-3-yl)vinyl)-5,7-
dimethylquinolin-8-ol

Example 24—Compound 317

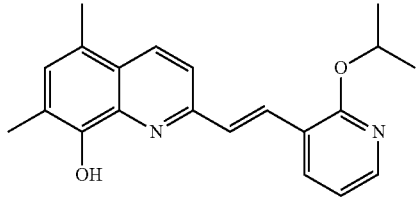

(E)-2-(2-(2-isopropoxypyridin-3-
yl)vinyl)-5,7-dimethylquinolin-8-ol

Figure 19A:
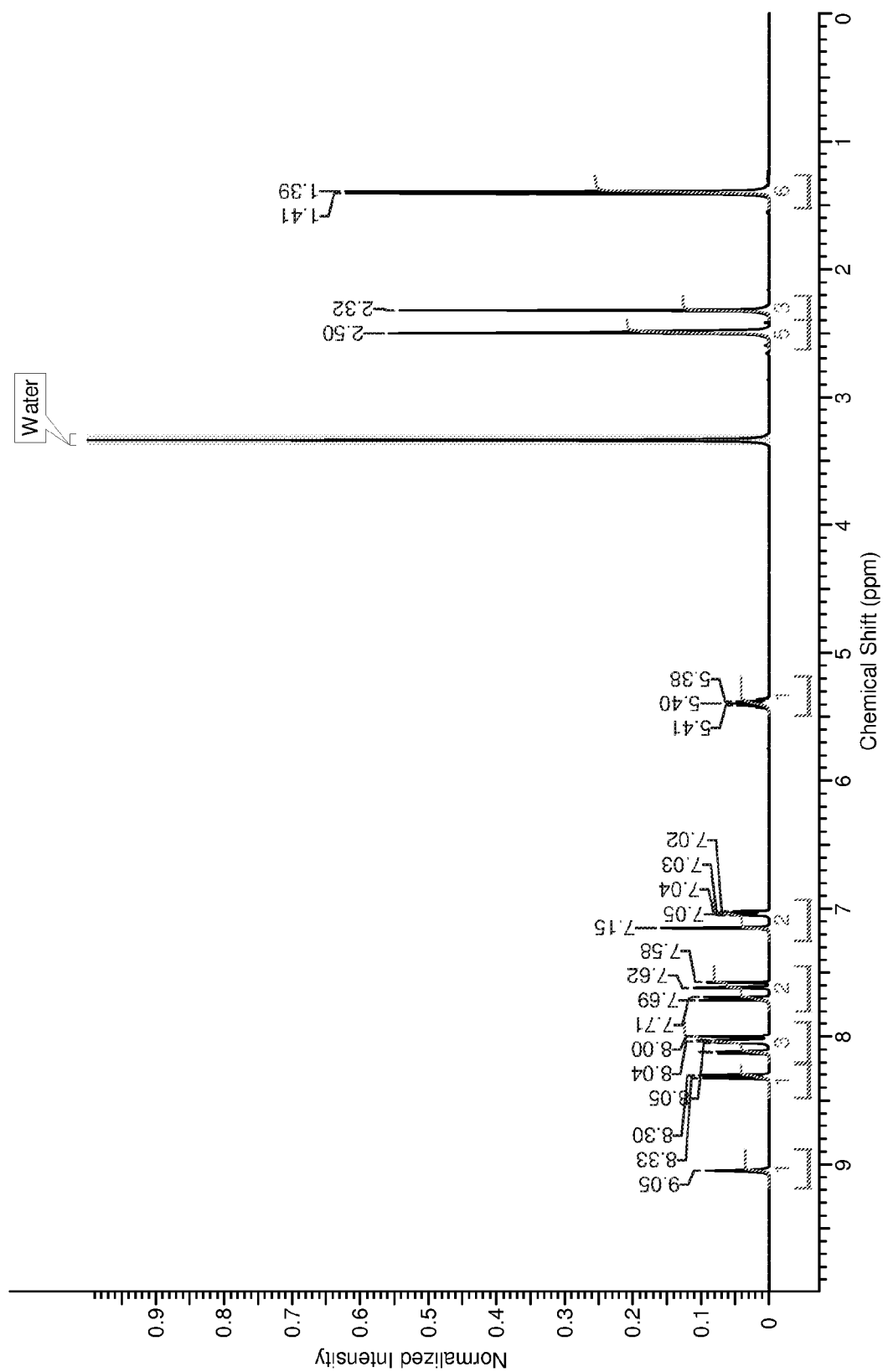
FIG. 19 shows the a) $^1$H NMR characterisation data and b) mass spectrometry characterisation data for compound 317.
Figure 19B:
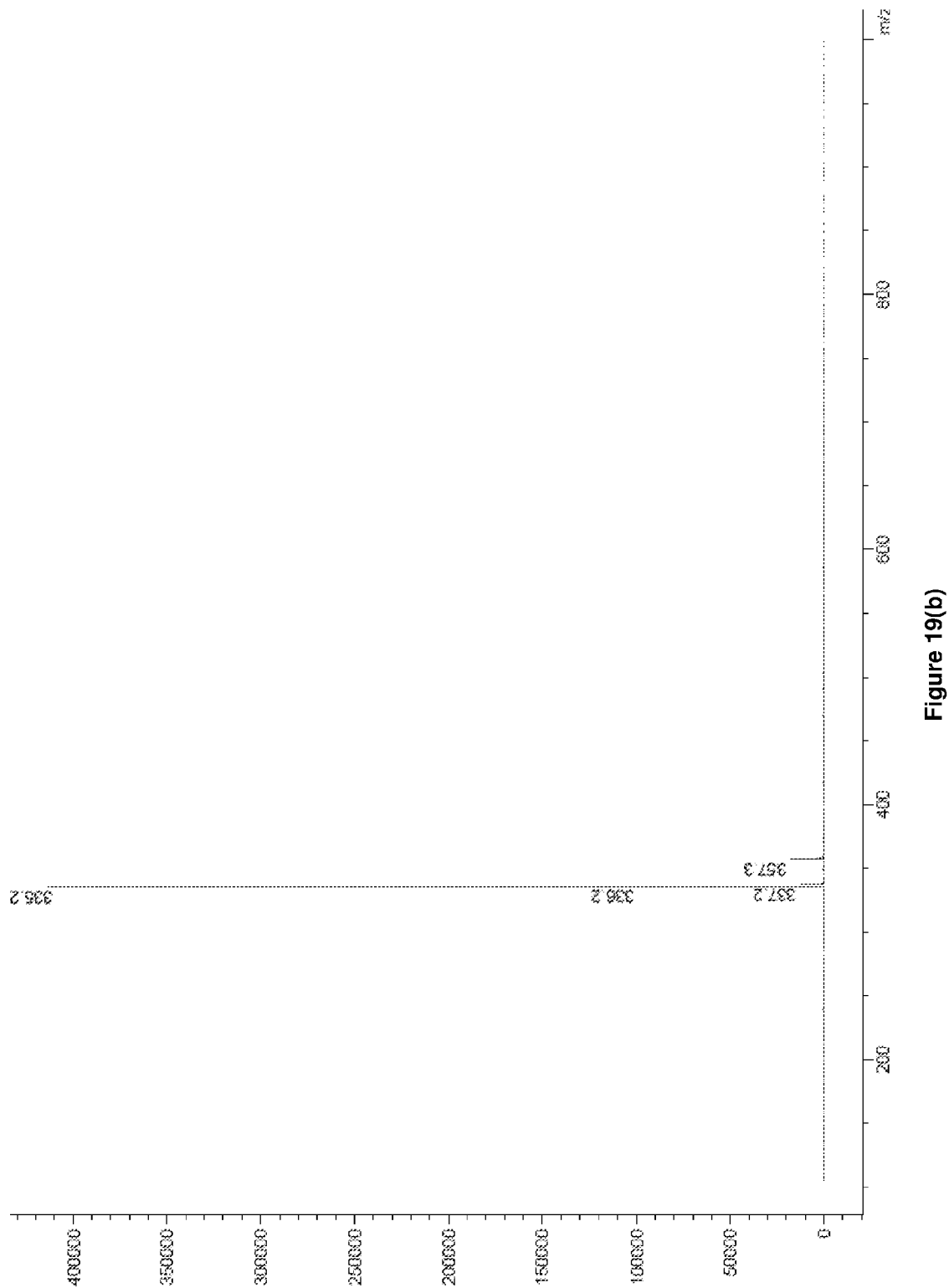

FIG. 19 shows spectroscopic ($^1$H NMR) and spectrometric (mass spec) characterisation of compound 317.

Example 25—Compound 318

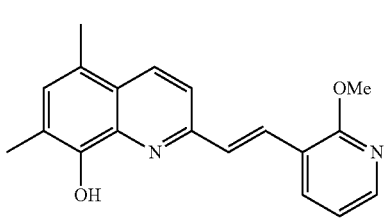

(Compound #318)

(E)-2-(2-(2-methoxypyridin-3-yl)vinyl)-5,7-dimethylquinolin-8-ol

Figure 20A:
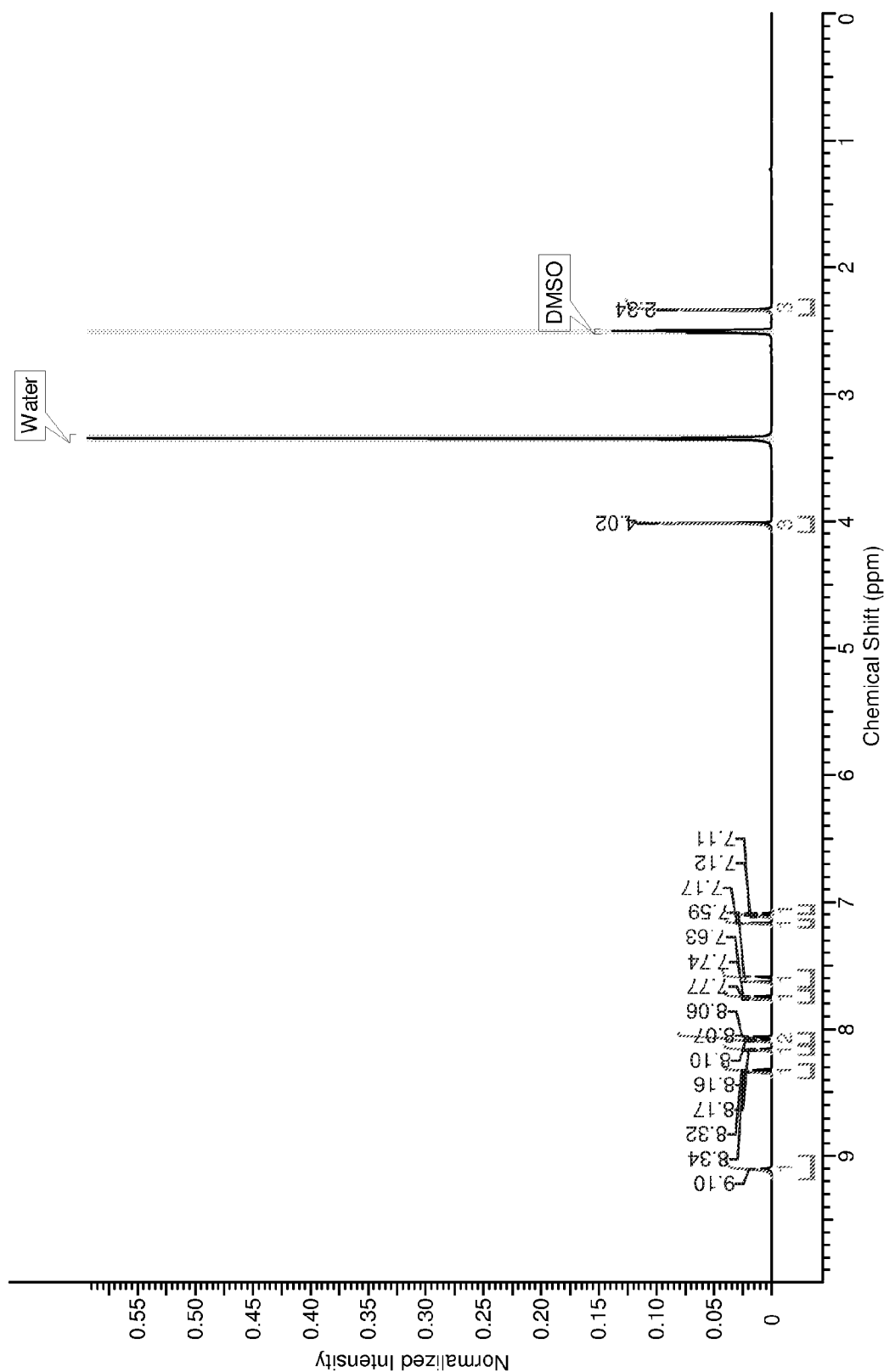
FIG. 20 shows the a) $^1$H NMR characterisation data and b) mass spectrometry characterisation data for compound 318.
Figure 20B:
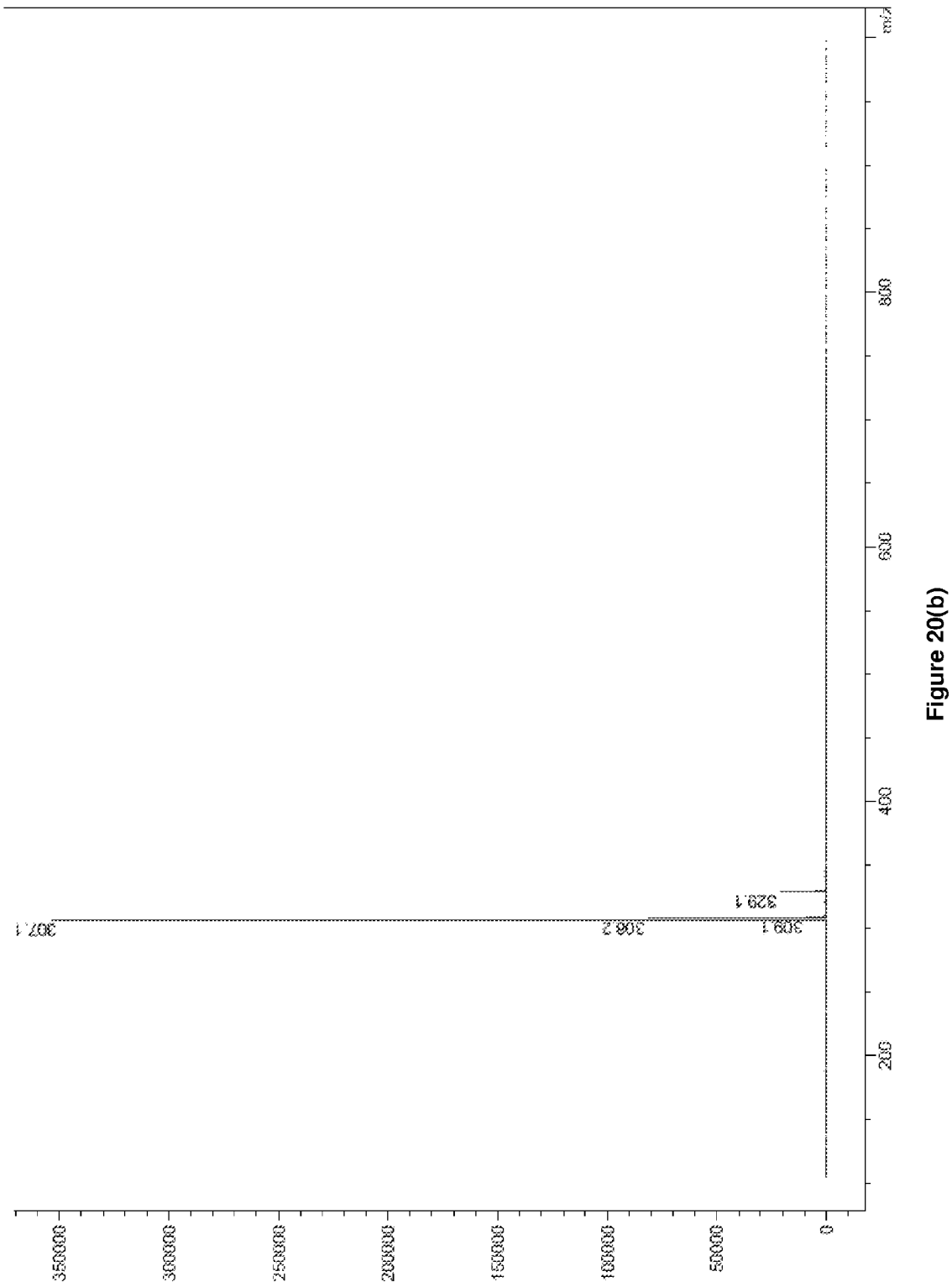

FIG. 20 shows spectroscopic ($^1$H NMR) and spectrometric (mass spec) characterisation of compound 318.

Example 26—Compound 319

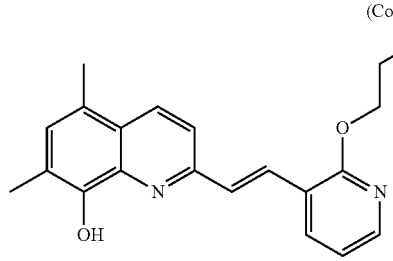

(Compound #319)

(E)-5,7-dimethyl-2-(2-(2-propoxypyridin-3-yl)vinyl)quinolin-8-ol

Figure 21A:
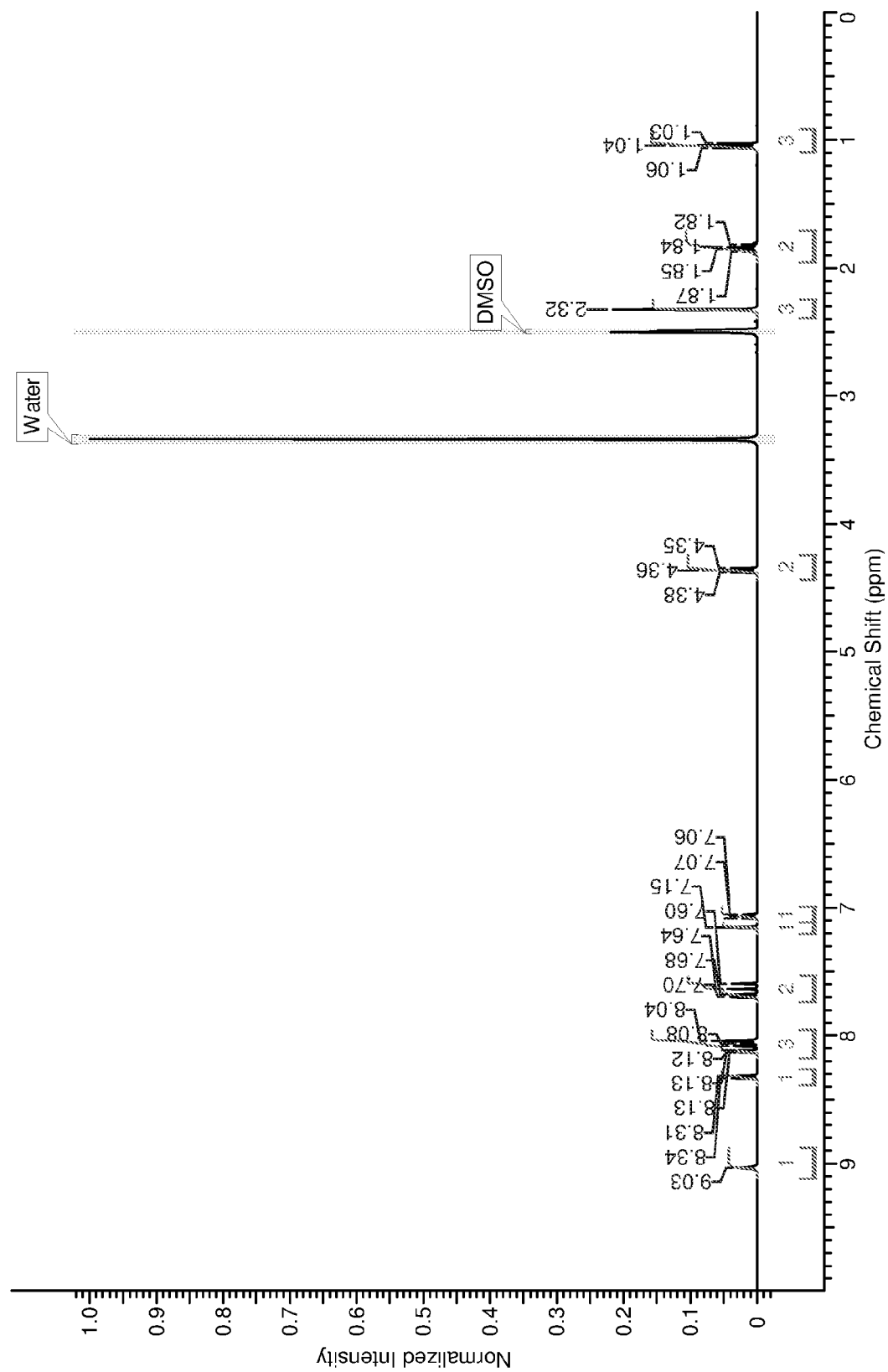
FIG. 21 shows the a) $^1$H NMR characterisation data and b) mass spectrometry characterisation data for compound 319.
Figure 21B:
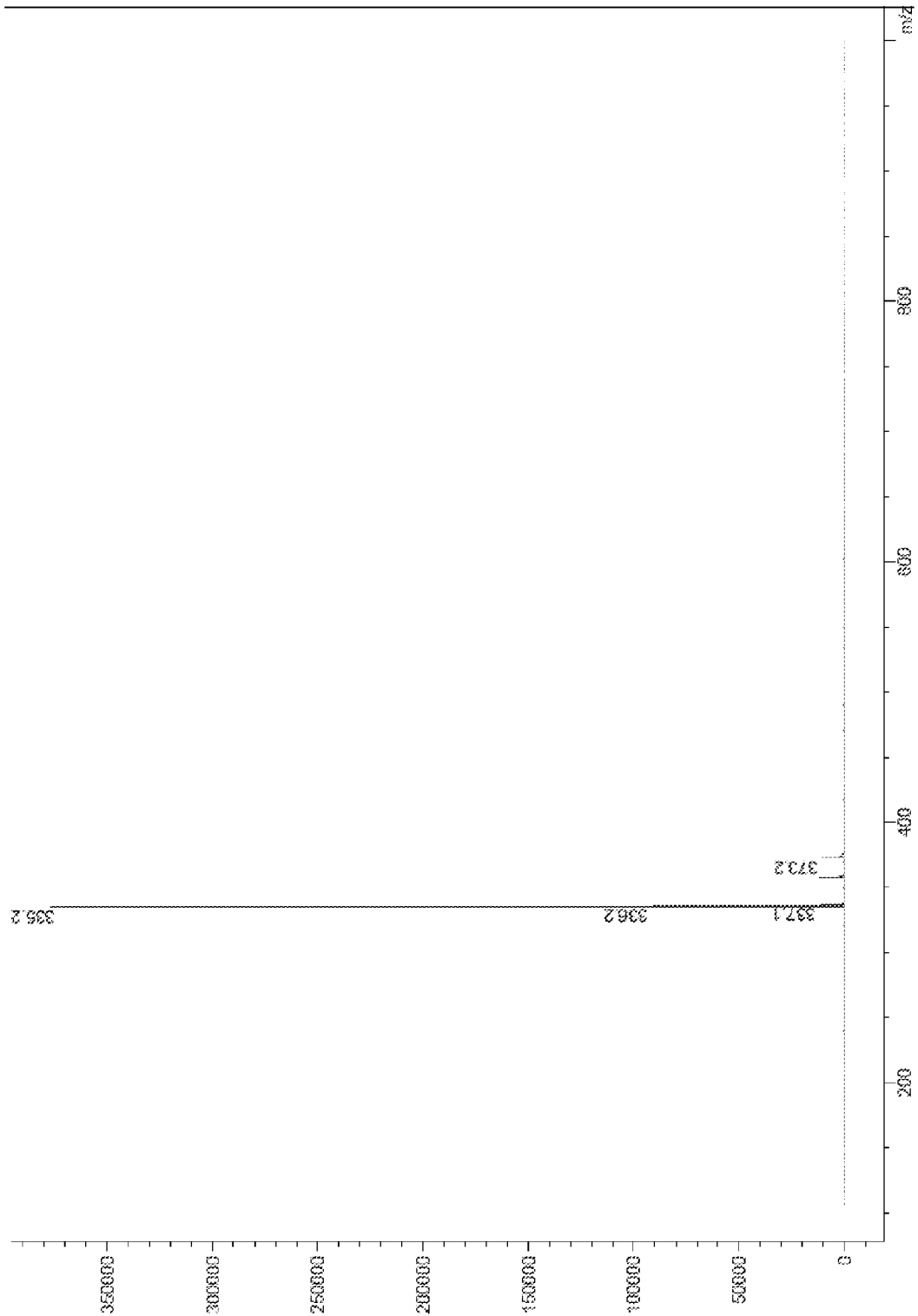

FIG. 21 shows spectroscopic ($^1$H NMR) and spectrometric (mass spec) characterisation of compound 319.

Example 27—Compound 321

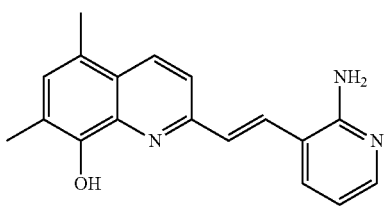

(Compound #321)

(E)-2-(2-(2-aminopyridin-3-yl)vinyl)-5,7-dimethylquinolin-8-ol

Figure 22A:
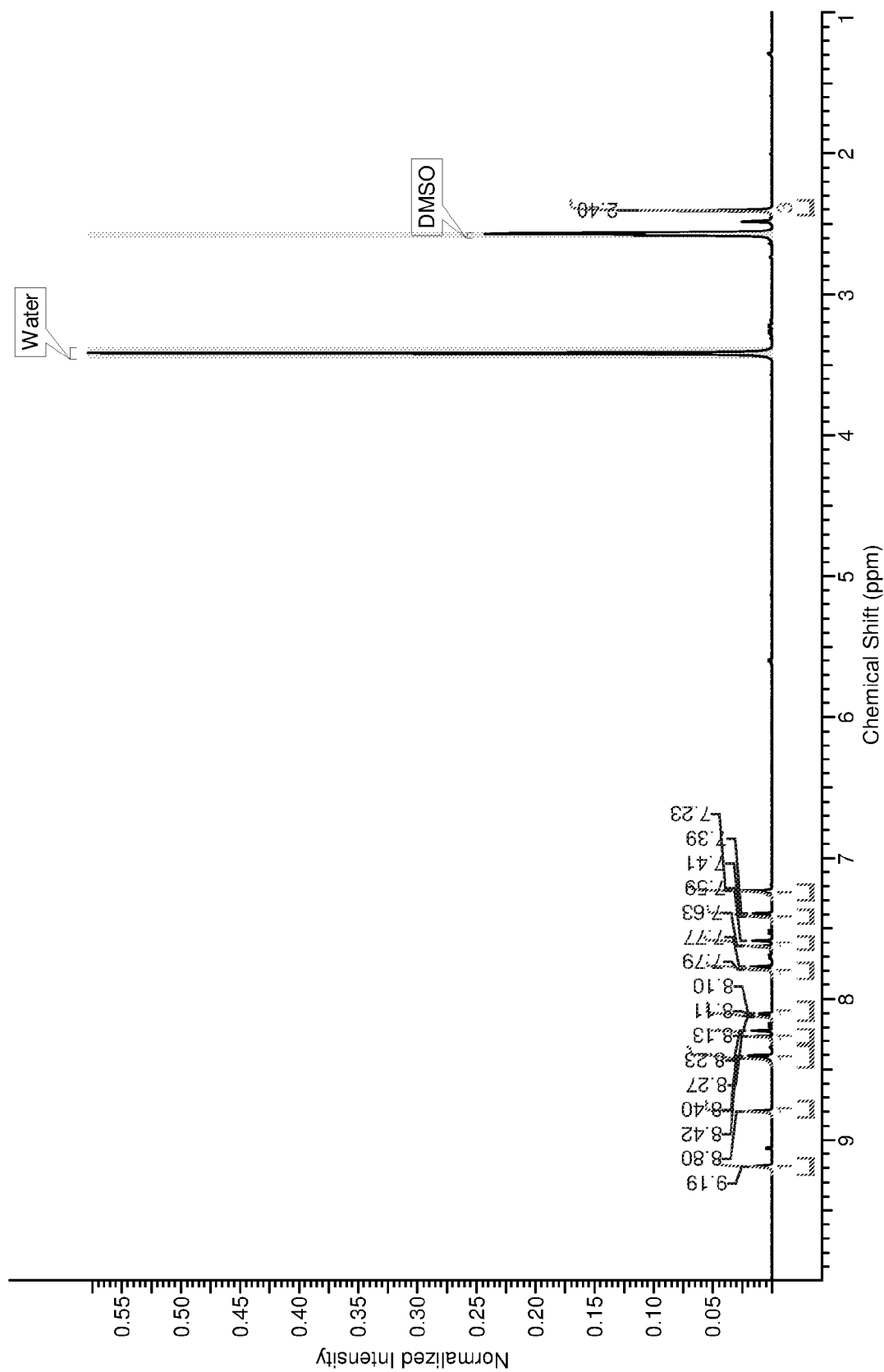
FIG. 22 shows the a) $^1$H NMR characterisation data and b) mass spectrometry characterisation data for compound 321.
Figure 22B:
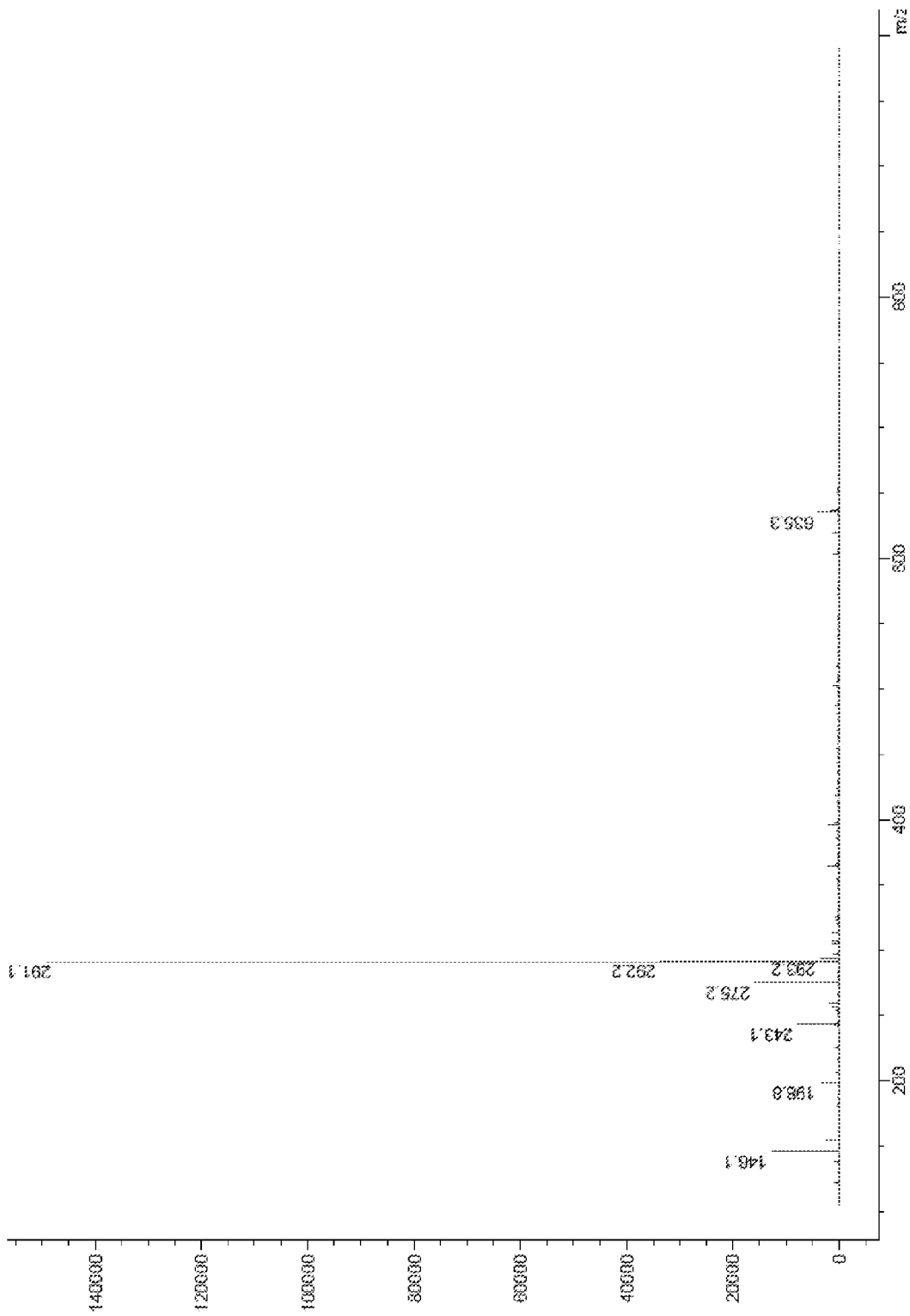

FIG. 22 shows spectroscopic ($^1$H NMR) and spectrometric (mass spec) characterisation of compound 321.

Example 28—Compound 322

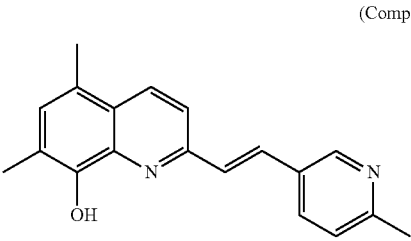

(Compound #322)

(E)-5,7-dimethyl-2-(2-(6-methylpyridin-3-yl)vinyl)quinolin-8-ol

Figure 23A:
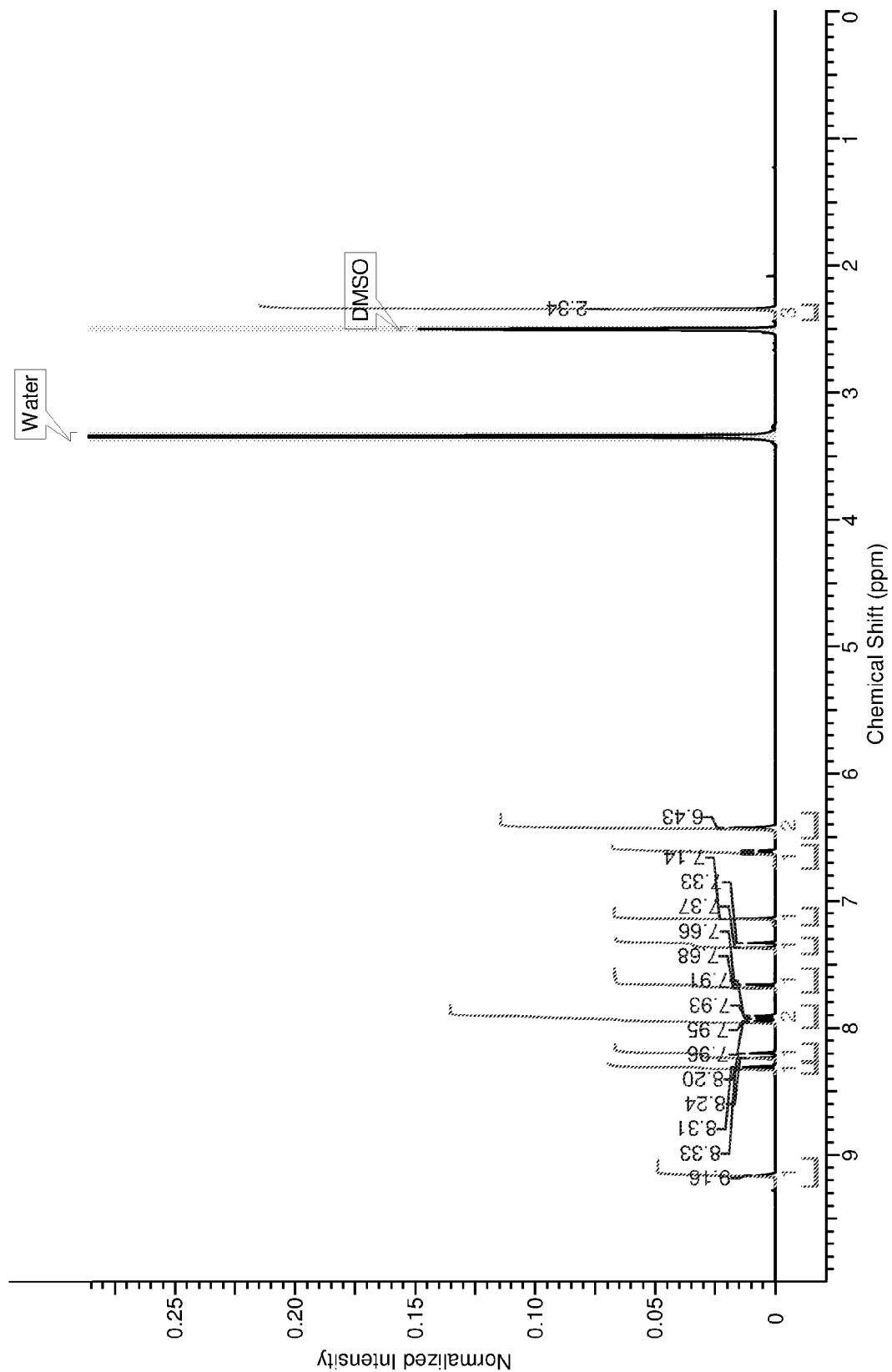
FIG. 23 the a) $^1$H NMR characterisation data and b) mass spectrometry characterisation data for compound 322.
Figure 23B:
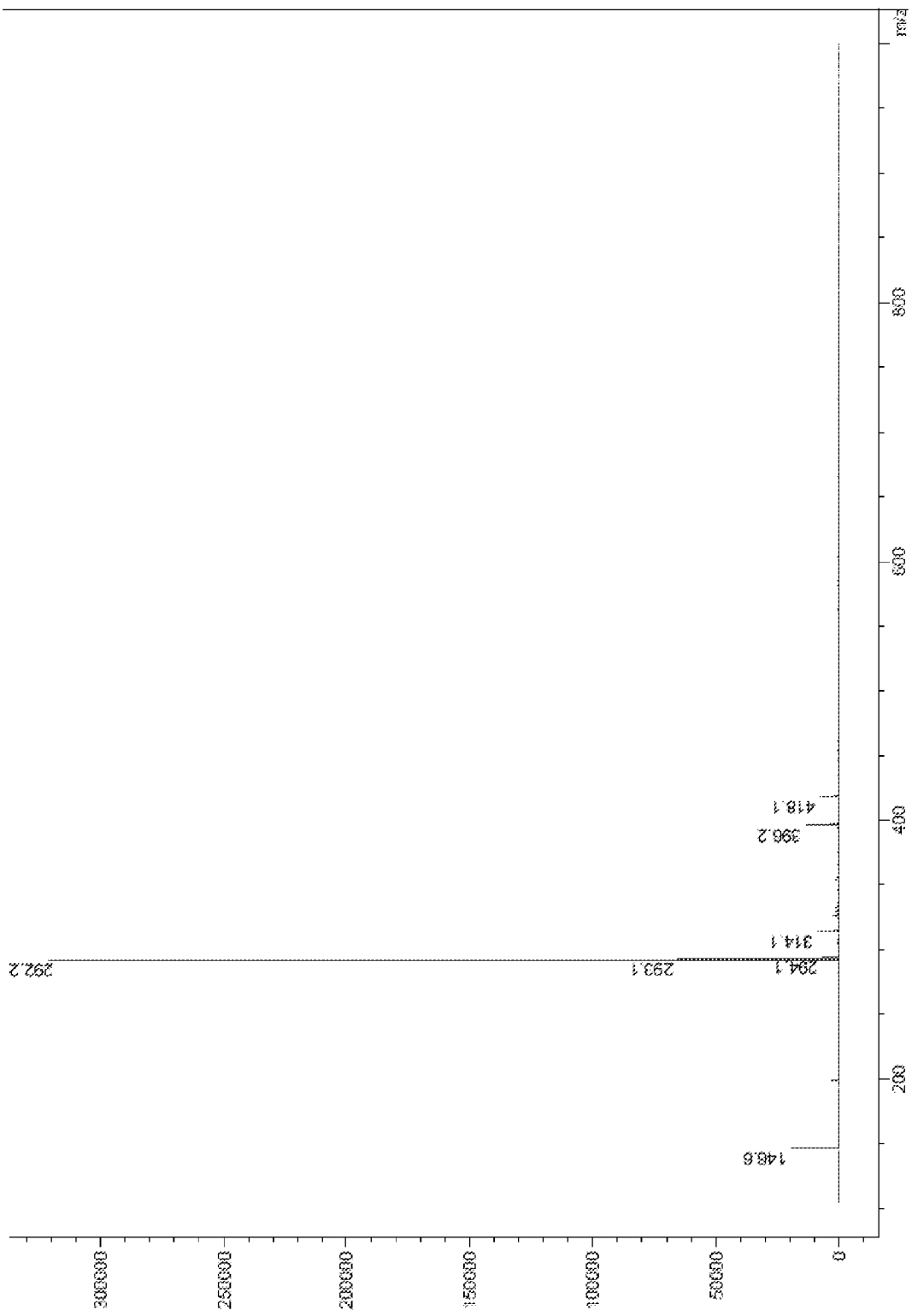

FIG. 23 shows spectroscopic ($^1$H NMR) and spectrometric (mass spec) characterisation of compound 322.

Example 29—Compound 323

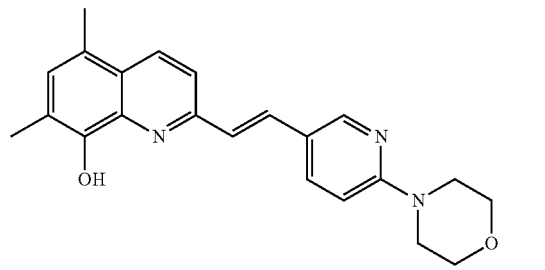

(Compound #323)

(E)-5,7-dimethyl-2-(2-(6-morpholinopyridin-3-yl)vinyl)quinolin-8-ol

Figure 24:
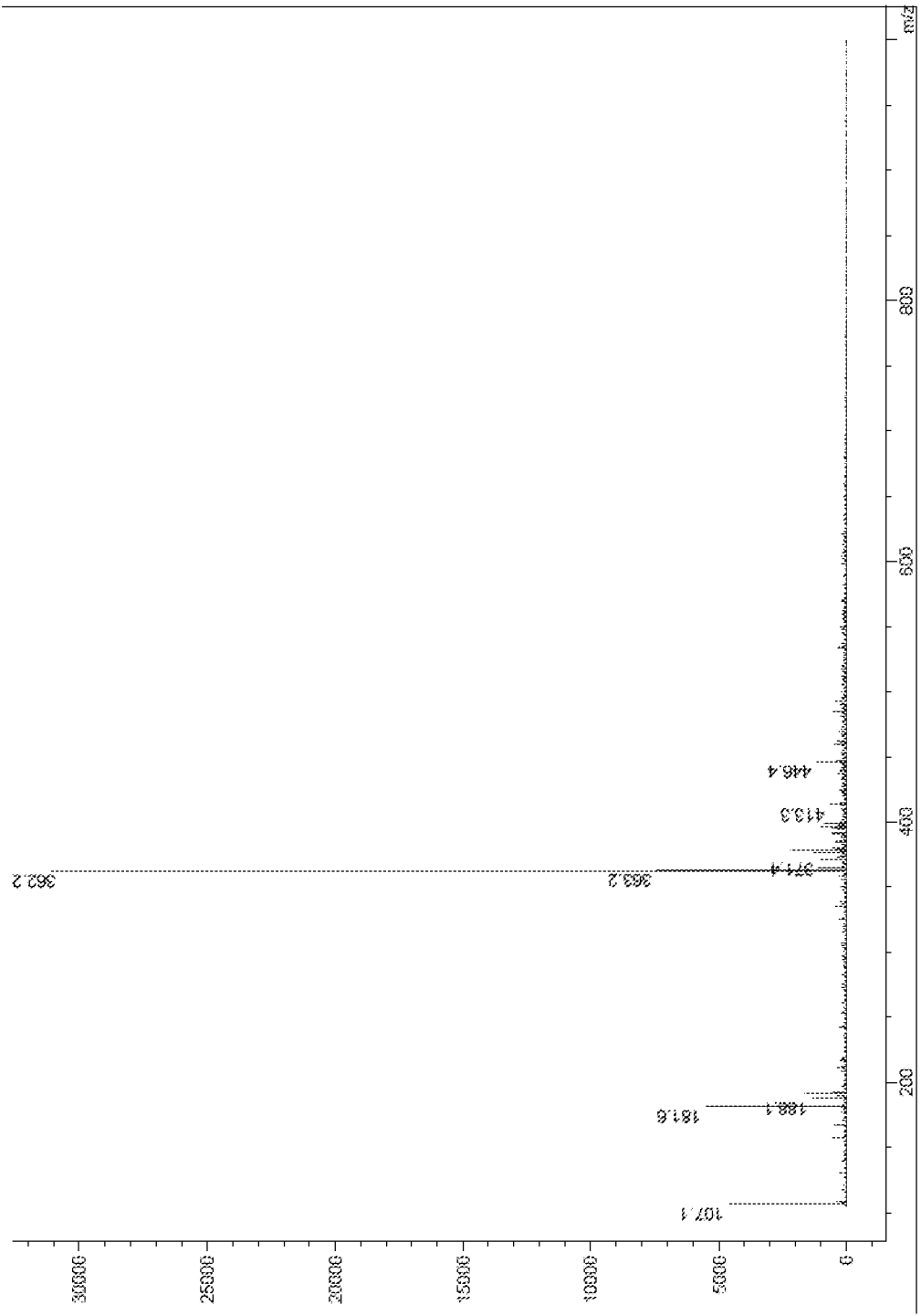
FIG. 24 shows the mass spectrometry characterisation data for compound 323.

FIG. 24 shows spectrometric (mass spec) characterisation of compound 323.

Example 30—Compound 324

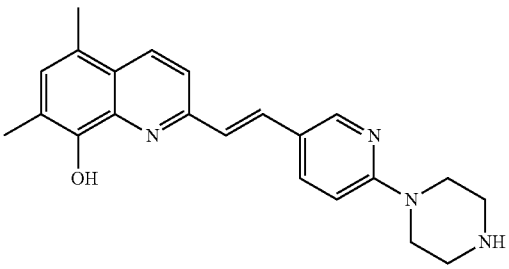

(Compound #324)

(E)-5,7-dimethyl-2-(2-(6-(piperazin-1-yl)pyridin-3-yl)vinyl)quinolin-8-ol

Figure 25:
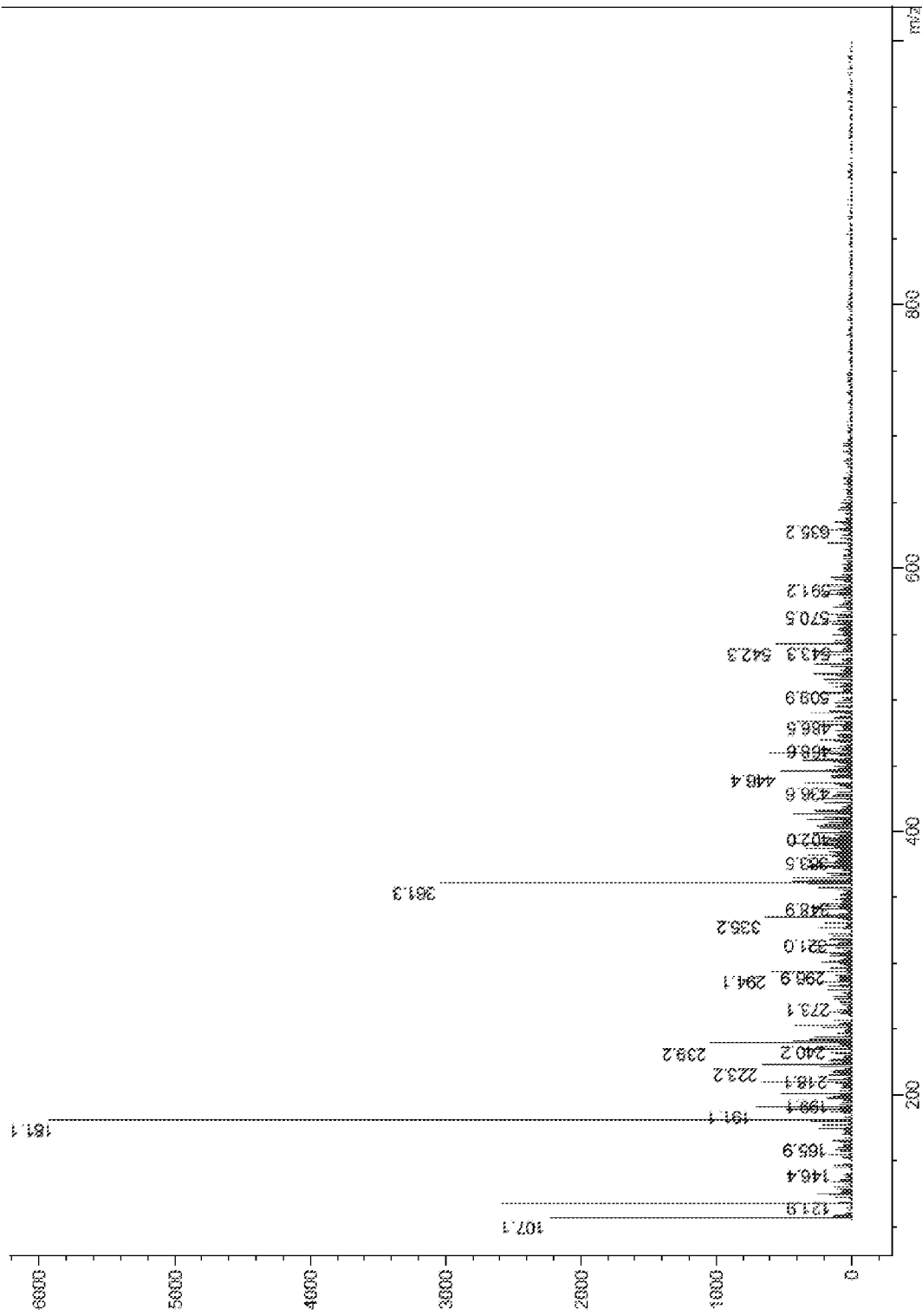
FIG. 25 shows the mass spectrometry characterisation data for compound 324.

FIG. 25 shows spectrometric (mass spec) characterisation of compound 324.

Example 31—Compound 325

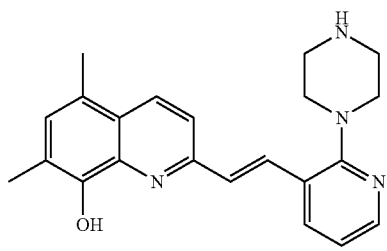

(Compound #325)

(E)-5,7-dimethyl-2-(2-(2-(piperazin-1-yl)pyridin-3-yl)vinyl)quinolin-8-ol

Figure 26:
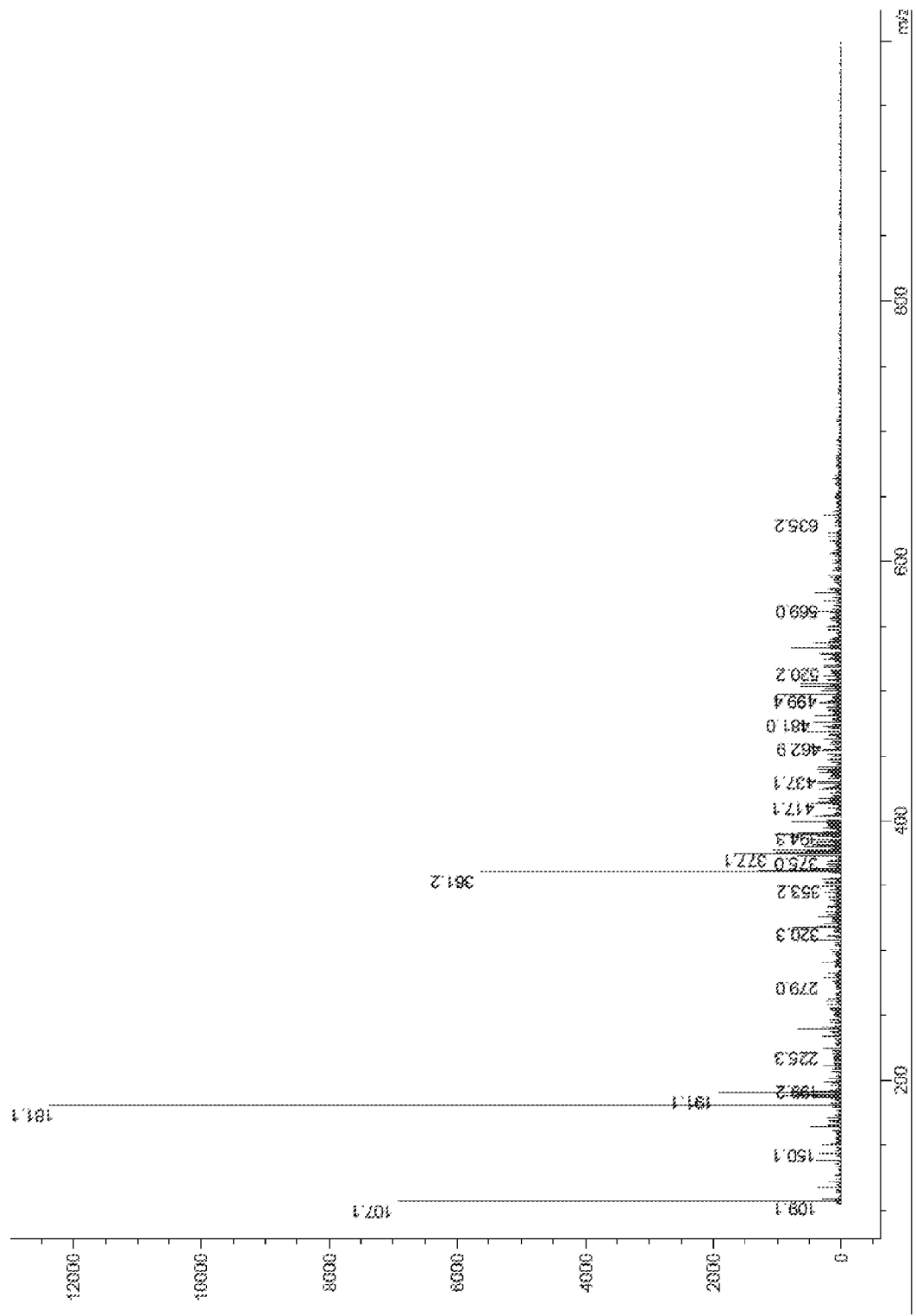
FIG. 26 shows the mass spectrometry characterisation data for compound 325.

FIG. 26 shows spectrometric (mass spec) characterisation of compound 325.

Example 32—Compound 326

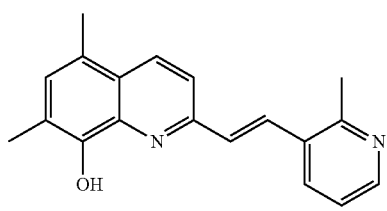

(Compound #326)

(E)-5,7-dimethyl-2-(2-(2-methylpyridin-3-yl)vinyl)quinolin-8-ol

Pharmacological Testing and Biological Assays

Example A—In Vitro Assembly Assay (IAPP and Aβ Assays)

The assay is based upon the altered fluorescent properties of the dye thioflavin T when it is intercalated into stacked beta-strand structures, which includes amyloid fibrils. The assay is carried out in multi-well plates in which the air-water interface (AWI) can be independently occluded at any time in the assay by the insertion in any well of a hydrophilic poly-methyl-methacrylate cylinder (Perspex). The cylinder consists of a rod of 6.6 mm in diameter and 6 mm in height with a hemispherical tip. This provides a close fit for the circular cross-section of the well, minimising residual air-water interface, and the hemispherical contour on the inserted end serves to ensure that no air bubbles are trapped on insertion.

The assay has a final volume of 100 μl and contains a buffered isotonic solution (Phosphate Buffered Saline pH 7.4), 32 μM Thioflavin T (ThT), an amyloidogenic precursor peptide (Islet amyloid precursor polypeptide, IAPP at 4 μM, or Abeta1-40 at 12 μM, final concentration) and added compounds at indicated concentrations (dissolved in dimethyl sulphoxide, DMSO) or DMSO alone. Purified synthetic peptides corresponding to IAPP (Bachem, Weil am Rhein, Germany) and $A\beta_{1-40}$ (EZBiolab, Carmel, Ind., USA) were dissolved in DMSO, sonicated, and centrifuged for 1 hour at 15,000 g and 4° C. before use (to remove any pre-aggregated species).

The ThT fluorescence signal was measured at 1 minute intervals (excitation 450 nm, emission 480 nm) in a 96-well plate (black wall, clear bottom; Greiner Bio-One, Stonehouse, Gloucestershire, UK) without shaking at 37° C. on a Polarstar plate reader (BMG Labtech, Aylesbury, Buckinghamshire, UK).

Any compound or physical device (e.g., Perspex cylinder) used was introduced at the same time in test (containing IAPP) and control wells (buffer and ThT without IAPP). Control values (with or without compounds or physical device) were subtracted from test values. At least 3 independent assays, with every assay done in duplicate wells, were performed and analyzed with the 2-sample t test.

The basic assay and its validation and reproducibility, together with the demonstration of liposome-mediated acceleration of assembly, are described in Jean et al (2010) *FASEB J* 24 309-317. A more detailed description of the IAPP and Aβ thioflavin/cylinder assay is given in Jean et al (2012) *Biophysical Journal* 102 1154-11.

The kinetics parameters were calculated from the ThT data as follows; the elongation rate was calculated from the slope at the inflection point of the sigmoidal curve; the plateau height was calculated by averaging the highest curve values (minimum of five values) attained at the end of the experiment; and the lag phase was calculated from the intercept on the time axis of the line formed tangent to the inflection point. At least three independent assays were performed, with every assay performed in duplicate wells. Statistical analysis was performed with the two-sample t-test. Details of the method of calculation of lag phase, elongation rate and plateau height are described in Trigg et al (2013) *Biochemical Journal* 456 67-80.

Results of Pharmacological Tests and Biological Assays

The pharmacological properties of compounds of the invention were studied by way of a dose response and IC50 against IAPP, and a screen against Amyloid-beta (Aβ) peptides. The results are shown in Table 1 below.

TABLE 1

Results of in vitro and in vivo assays

| Cmpd # | Ratio +AWI Lag phase | IAPP $IC_{50}$ (μm)/ −AWI elongation | Active against Aβ |
|---|---|---|---|
| 131 | 8 | 4 | |
| 214 | 32 | 3 | ✓ (rate) |
| 221 | 32 | 16 | |
| 222 | 11 | 3 | |
| 225 | 3 | 4 | |
| 226 | 1 | 3 | |
| 227 | 32 | 31 | ✓ (rate) |
| 229 | 32 | 32 | ✓ (rate) |
| 234 | 21 | 21 | |
| 236 | 8 | 11 | ✓ |
| 238 | 32 | 4 | |
| 239 | 11 | 32 | |
| 241 | 3 | 11 | No |
| 245 | 32 | 32 | ✓ |
| 249 | 32 | 12 | ✓ |
| 251 | 21 | 21 | ✓ |
| 252 | 1 | 3 | |
| 311 | 4 | 1 | ND |
| 312 | 2 | 1 | ND |
| 321 | 3 | >1 | ND |
| 322 | 4 | 1 | ND |
| 323 | 11 | 2.5 | ND |
| 324 | 21 | 4 | ND |

TABLE 1-continued

Results of in vitro and in vivo assays

| Cmpd # | Ratio +AWI Lag phase | IAPP IC$_{50}$ (μm)/ −AWI elongation | Active against Aβ |
|---|---|---|---|
| 325 | 1 | 5 | ND |
| 326 | 1 | 1 | ND |

Suitably, a compound is considered active where it displays a ratio of IC$_{50+AWI}$/IC$_{50-AWI}$ of greater than or equal to 1, suitably greater than or equal to 5, most suitably greater than or equal to 8, especially for the lag phase, though preferably also for the elongation rate.

Compounds 214, 236, 241, 249 and 251 also showed activity in an in vivo *C. elegans* model.

REFERENCES

Ariola F S et al (2006) "Interfacial rheology of blood proteins adsorbed to the aqueous-buffer/air interface." *Biomaterials* 27 3404

Bolisetty S et al (2012) "Gelation, phase behavior, and dynamics of beta-lactoglobulin amyloid fibrils at varying concentrations and ionic strengths." *Biomacromol* 13 3241

Butterfield S M and Lashuel H A (2010) "Amyloidogenic protein-membrane interactions: mechanistic insight from model systems" *Angew Chem Int Ed* 49 5628

Chi E Y et al (2008) "Amyloid-β Fibrillogenesis Seeded by Interface-Induced Peptide Misfolding and Self-Assembly" *Proteins* 72 1

Cottingham M G et al (2002) "Amyloid fibril formation by a synthetic peptide from a region of human acetylcholinesterase that is homologous to the Alzheimer's amyloid-β peptide" *Biochemistry* 41 13539

Cottingham M G et al (2003) "The intact human acetylcholinesterase C-terminal oligomerization domain is α-helical in situ and in isolation, but a shorter fragment forms β-sheet-rich amyloid fibrils and protofibrillar oligomers" *Biochemistry* 42 10863

Cottingham M G et al (2004) "Rapid method for measurement of surface tension in multiwell plates" *Lab Invest* 84 523

Cox A R et al (2007) "Surface properties of class ii hydrophobins from *Trichoderma reesei* and influence on bubble stability" *Langmuir* 23 7995

Demuro A et al (2005) "Calcium dysregulation and membrane disruption as a ubiquitous neurotoxic mechanism of soluble amyloid oligomers" *J Biol Chem* 280 17294

Graham D E et al (1979) "Proteins at liquid interfaces: II. Adsorption isotherms" *J Colloid and Interface Sci* 70 415

Jean L et al (2007) "Heterologous amyloid seeding: revisiting the role of acetylcholinesterase in Alzheimer's disease" *PLoS ONE* 2(7): e652.

Jean L et al. (2008) "Structural elements regulating amyloidogenesis: a cholinesterase model system" *PLoS ONE* 3(3):e1834.

Jean L et al (2010) "Competing discrete interfacial effects are critical for amyloidogenesis" *FASEB J.* 24 309

Jean L et al (2012) "Enrichment of amyloidogenesis at an air-water interface" *Biophys J* 102 1154

Jin S and Verkman A S (2007) "Single Particle Tracking of Complex Diffusion in Membranes: Simulation and Detection of Barrier, Raft, and Interaction Phenomena" *J Phys Chem* 111 3625

Kayed R et al (2004) "Permeabilization of lipid bilayers is a common conformation-dependent activity of soluble amyloid oligomers in protein misfolding diseases" *J Biol Chem* 279 46363

Knight J D and Miranker A D (2004) "Phospholipid catalysis of diabetic amyloid assembly" *J Mol Biol* 341 1175

Knight J D et al (2006) "Conserved and cooperative assembly of membrane-bound alpha-helical states of islet amyloid polypeptide" *Biochemistry* 45 9496

Krysmann M J et al (2008) "Self-assembly and hydrogelation of an amyloid peptide fragment" *Biochemistry* 47 4597

Lakshmanan A et al (2013) "Aliphatic peptides show similar self-assembly to amyloid core sequences, challenging the importance of aromatic interactions in amyloidosis" *PNAS* 110 519

Lee C F et al (2012) "Combined effects of agitation, macromolecular crowding, and interfaces on amyloidogenesis" *J Biol Chem* 287: 38006

Lepere M et al (2007) "Multiscale surface self-assembly of an amyloid-like peptide" *Langmuir* 23 8150

Lopes D H et al (2007) "Mechanism of islet amyloid polypeptide fibrillation at lipid interfaces studied by infrared reflection absorption spectroscopy" *Biophys J* 93 3132

Lublin A L, Link C D (2013) "Alzheimer's disease drug discovery: in vivo screening using *C. elegans* as a model for β-amyloid peptide-induced toxicity" *Drug Discov Today Technol.* 10:e115-9.

Manno M et al (2010) "Amyloid gels: precocious appearance of elastic properties during the formation of an insulin fibrillar network" *Langmuir* 26 1424

Quist A et al (2005) "Amyloid ion channels: a common structural link for protein-misfolding disease" *Proc Natl Acad Sci USA* 102 10427

Rijkers D T S et al (2002) "Inhibition of amyloid fibril formation of human amylin by N-alkylated amino acid and alpha-hydroxy acid residue containing peptides" *Chem Eur J* 8 4285

Schmidt et al (1990) "Multilayer adsorption of lysozyme on a hydrophobic substrate" *Biophys J* 57 577

Soderlund T et al (2003) "Comparison of the effects of surface tension and osmotic pressure on the interfacial hydration of a fluid phospholipid bilayer" *Biophysical J* 85 2333

Soreghan B et al (1994) "Surfactant properties of Alzheimer's A beta peptides and the mechanism of amyloid aggregation" *J Biol Chem* 269 28551

Terzi E et al (1997) "Interaction of Alzheimer beta-amyloid peptide (1-40) with lipid membranes" *Biochemistry* 36 14845

Trigg B et al (2013) "The air-water interface determines the outcome of seeding during amyloidogenesis" *Biochem J* 456 67

Wu H et al (1993) "Induction of changes in the secondary structure of globular proteins by a hydrophobic surface" *Eur Biophys J* 22 201

Wu C et al (2012) "Quantitative analysis of amyloid-integrated biofilms formed by uropathogenic *Escherichia coli* at the air-liquid interface" *Biophys J* 103 464

Yang Y et al (2012) "Behavior of silk protein at the air-water interface" *Soft Matter* 8 9705

The invention claimed is:

1. A compound of Formula Ib:

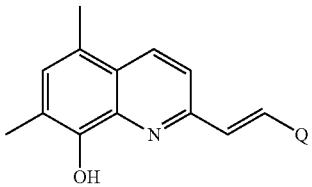

Formula Ib wherein:
Q is a ring system selected from a 5- or 6-membered heteroaryl, or (5-7C)cycloalkyl, each of which is optionally fused to a 5- or 6-membered heterocyclyl ring, and wherein the Q ring system is optionally substituted by: one, two, or three $R_Q$ groups; wherein $R_Q$ is independently selected from halo, hydroxy, nitro, cyano, (1-4C)alkyl, (1-4C)haloalkyl, (1-4C)alkoxy, (1-4C)haloalkoxy, $NR_cR_c$, $C(O)R_c$, $C(O)OR_c$, $OC(O)R_c$, $C(O)N(R_d)R_c$, $N(R_c)C(O)R_d$, $S(O)_pR_c$ (where p is 0, 1 or 2), $SO_2N(R_c)R_d$, $N(R_c)SO_2R_d$, or a 4-, 5-, 6-membered heterocyclyl,
wherein $R_c$ and $R_d$ are each independently selected from H or (1-4C)alkyl;
or a pharmaceutically acceptable salt, hydrate or solvate thereof.

2. The compound as claimed in claim 1, wherein Q is a ring system selected from a 5- or 6-membered heteroaryl, or (5-7C)cycloalkyl, each of which is optionally fused to a 5-membered heterocyclyl ring to form a methylenedioxy-substituted ring system, and wherein the Q ring system is optionally substituted by one or two $R_Q$ groups; wherein $R_Q$ is independently selected from halo, hydroxy, nitro, cyano, (1-3C)alkyl, trifluoromethyl, (1-3C)alkoxy, trifluoromethoxy, $NH_2$, $C(O)OR_c$, or a 6-membered heterocyclyl.

3. The compound as claimed in claim 1, wherein Q is a ring system selected from furanyl, pyridyl, or cyclohexyl, each of which is optionally fused to a 5- or 6-membered heterocyclyl ring, and wherein the Q ring system is optionally substituted by one, two, or three $R_Q$ groups; wherein $R_Q$ is independently selected from halo, hydroxy, nitro, cyano, (1-4C)alkyl, (1-4C)haloalkyl, (1-4C)alkoxy, (1-4C)haloalkoxy, $NR_cR_c$, $C(O)R_c$, $C(O)OR_c$, $OC(O)R_c$, $C(O)N(R_d)R_c$, $N(R_c)C(O)R_d$, $S(O)_pR_c$ (where p is 0, 1 or 2), $SO_2N(R_c)R_d$, $N(R_c)SO_2R_d$, or a 4-, 5-, 6-membered heterocyclyl, wherein $R_c$ and $R_d$ are each independently selected from H or (1-4C)alkyl.

4. The compound as claimed in claim 3, wherein Q is pyridyl, which is optionally fused to a 5- or 6-membered heterocyclyl ring, and wherein the Q ring system is optionally substituted by one, two, or three $R_Q$ groups; wherein $R_Q$ is independently selected from halo, hydroxy, nitro, cyano, (1-4C)alkyl, (1-4C)haloalkyl, (1-4C)alkoxy, (1-4C)haloalkoxy, $NR_cR_c$, $C(O)R_c$, $C(O)OR_c$, $OC(O)R_c$, $C(O)N(R_d)R_c$, $N(R_c)C(O)R_d$, $S(O)_pR_c$ (where p is 0, 1 or 2), $SO_2N(R_c)R_d$, $N(R_c)SO_2R_d$, or a 4-, 5-, 6-membered heterocyclyl, wherein $R_c$ and $R_d$ are each independently selected from H or (1-4C)alkyl.

5. The compound as claimed in claim 4, wherein Q is a 3-pyridyl ring system, which is optionally fused to a 5- or 6-membered heterocyclyl ring, and wherein the Q ring system is optionally substituted by one, two, or three $R_Q$ groups; wherein $R_Q$ is independently selected from halo, hydroxy, nitro, cyano, (1-4C)alkyl, (1-4C)haloalkyl, (1-4C)alkoxy, (1-4C)haloalkoxy, $NR_cR_c$, $C(O)R_c$, $C(O)OR_c$, $OC(O)R_c$, $C(O)N(R_d)R_c$, $N(R_c)C(O)R_d$, $S(O)_pR_c$ (where p is 0, 1 or 2), $SO_2N(R_c)R_d$, $N(R_c)SO_2R_d$, or a 4-, 5-, 6-membered heterocyclyl, wherein $R_c$ and $R_d$ are each independently selected from H or (1-4C)alkyl.

6. The compound as claimed in claim 1, wherein the compound has the structural formula Ic shown below:

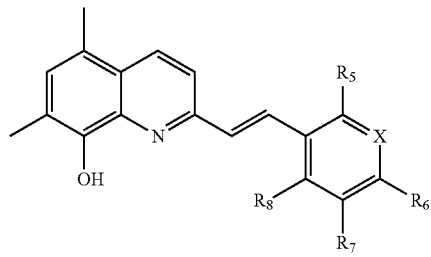

Formula Ic wherein X is N, and $R_5$, $R_6$, $R_7$ and $R_8$ are each independently hydrogen, halo, hydroxy, nitro, cyano, (1-4C)alkyl, (1-4C)haloalkyl, (1-4C)alkoxy, (1-4C)haloalkoxy, $NR_cR_c$, $C(O)R_c$, $C(O)OR_c$, $OC(O)R_c$, $C(O)N(R_d)R_c$, $N(R_c)C(O)R_d$, $S(O)_pR_c$ (where p is 0, 1 or 2), $SO_2N(R_c)R_d$, $N(R_c)SO_2R_d$, or a 4-, 5-, 6-membered heterocyclyl, wherein $R_c$ and $R_d$ are each independently selected from H or (1-4C);
or a pharmaceutically acceptable salt, hydrate and/or solvate thereof.

7. The compound as claimed in claim 6, having a structure of structural formula Id shown below:

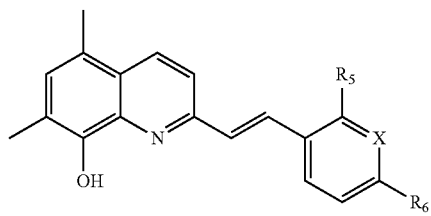

Formula Id or a pharmaceutically acceptable salt, hydrate and/or solvate thereof.

8. The compound as claimed in claim 1, wherein the compound is selected from any of the following:

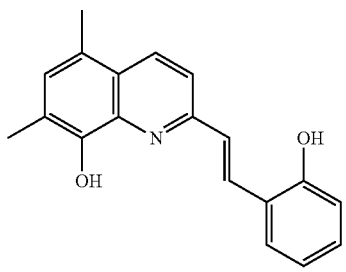

(Compound #214)

(E)-2-(2-hydroxystyryl)-5,7-dimethylquinolin-8-ol (Compound #221)

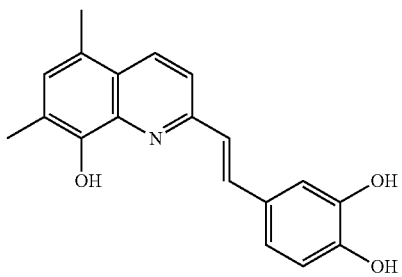

(E)-4-(2-(8-hydroxy-5,7-dimethylquinolin-2-yl)vinyl)benzene-1,2-diol (Compound #222)

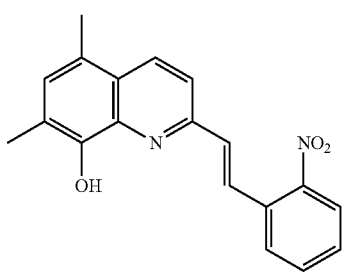

(E)-5,7-dimethyl-2-(2-nitrostyryl)quinolin-8-ol (Compound #225)

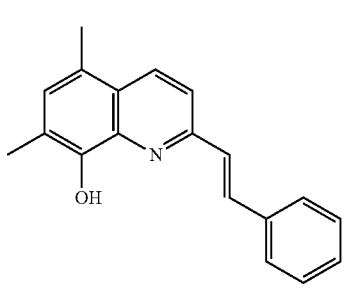

(E)-5,7-dimethyl-2-styrylquinolin-8-ol (Compound #226)

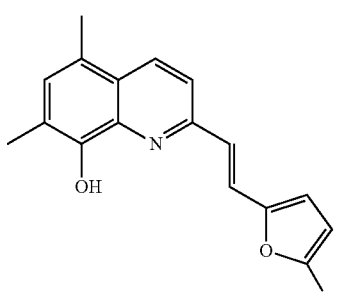

(E)-2-(2-(5-bromofuran-2-yl)vinyl)-5,7-dimethylquinolin-8-ol (Compound #227)

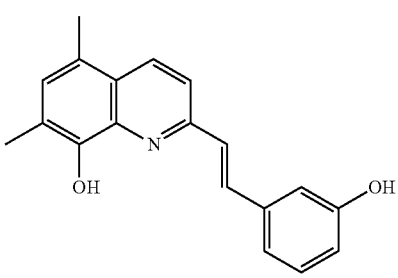

(E)-2-(3-hydroxystyryl)-5,7-dimethylquinolin-8-ol (Compound #229)

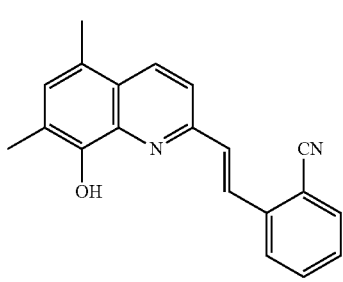

(E)-2-(2-(8-hydroxy-5,7-dimethylquinolin-2-yl)vinyl)benzonitrile (Compound #234)

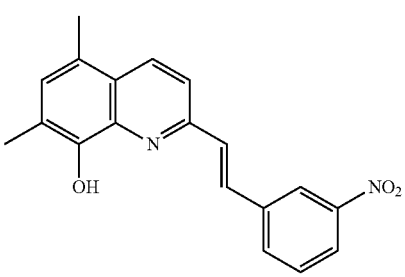

(E)-5,7-dimethyl-2-(3-nitrostyryl)quinolin-8-ol (Compound #236)

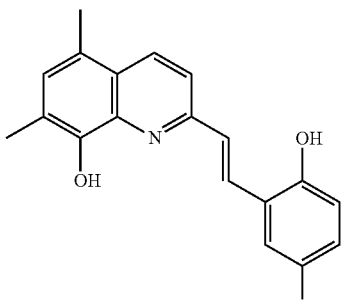

(E)-4-hydroxy-3-(2-(8-hydroxy-5,7-dimethylquinolin-2-yl)vinyl)benzoic acid (Compound #238)

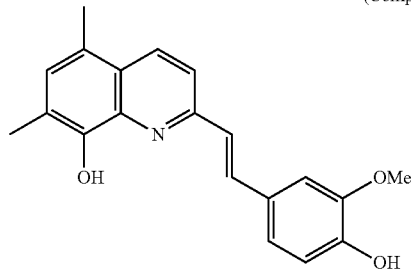

(E)-2-(4-hydroxy-3-methoxystyryl)-
5,7-dimethylquinolin-8-ol (Compound #239)

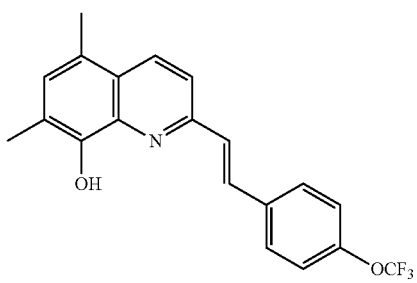

(E)-5,7-dimethyl-2-(4-
(trifluoromethoxy)styryl)quinolin-8-ol (Compound #241)

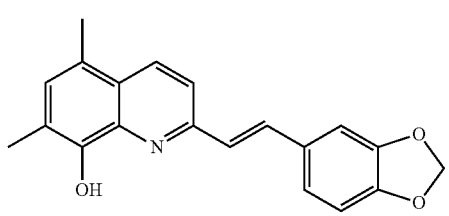

(E)-2-(2-(benzo[d][1,3]dioxol-5-yl)vinyl)-
5,7-dimethylquinolin-8-ol (Compound #245)

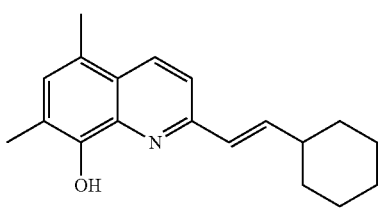

(E)-2-(2-cyclohexylvinyl)-
5,7-dimethylquinolin-8-ol (Compound #249)

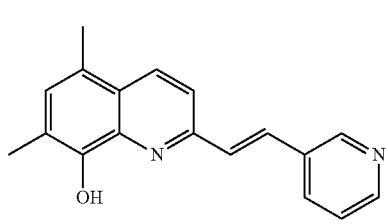

(E)-5,7-dimethyl-2-(2-(pyridin-3-
yl)vinyl)quinolin-8-ol (Compound #251)

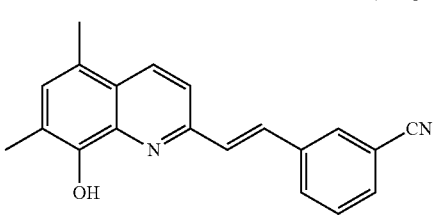

(E)-3-(2-(8-hydroxy-5,7-
dimethylquinolin-2-yl)vinyl)benzonitrile (Compound #252)

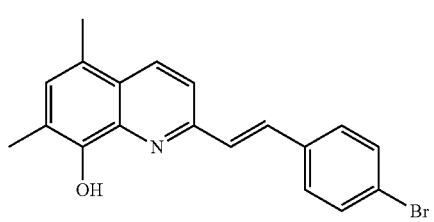

(E)-2-(4-bromostyryl-5,7-
dimethylquinolin-8-ol (Compound #311)

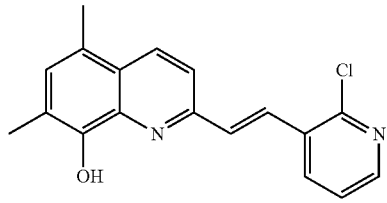

(E)-2-(2-(2-chloropyridin-3-yl)vinyl)-
5,7-dimethylquinolin-8-ol (Compound #312)

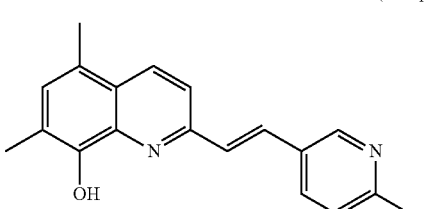

(E)-2-(2-(6-methoxypyridin-3-yl)vinyl)-
5,7-dimethylquinolin-8-ol (Compound #313)

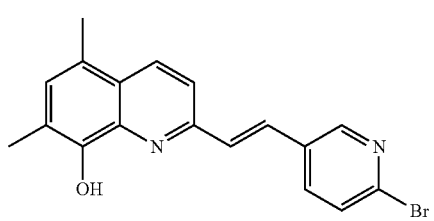

(E)-2-(2-(6-bromopyridin-3-
yl)vinyl)-5,7-dimethylquinolin-8-ol (Compound #314)

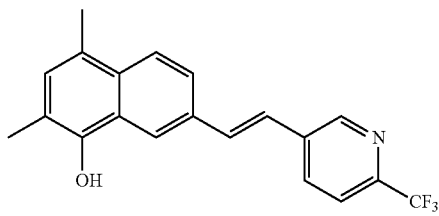

(E)-5,7-dimethyl-2-(2-(6-
(trifluoromethyl)pyridin-3-
yl)vinyl)quinolin-8-ol (Compound #315)

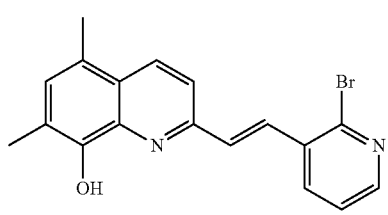

(E)-2-(2-(2-bromopyridin-3-yl)vinyl)-
5,7-dimethylquinolin-8-ol (Compound #316)

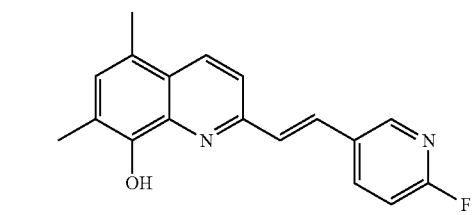

(E)-2-(2-(6-fluoropyridin-3-yl)vinyl)-
5,7-dimethylquinolin-8-ol (Compound #317)

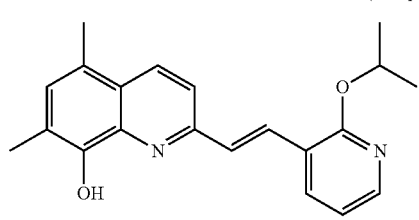

(E)-2-(2-(2-isopropoxypyridin-3-yl)vinyl)-
5,7-dimethylquinolin-8-ol (Compound #318)

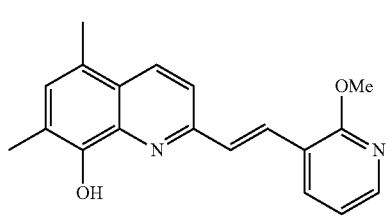

(E)-2-(2-(2-methoxypyridin-3-yl)vinyl)-
5,7-dimethylquinolin-8-ol (Compound #319)

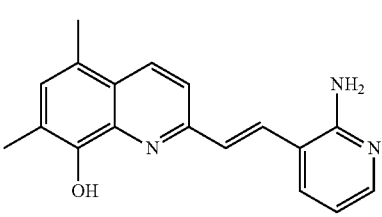

(E)-5,7-dimethyl-2-(2-(2-propoxypyridin-3-
yl)vinyl)quinolin-8-ol (Compound #321)

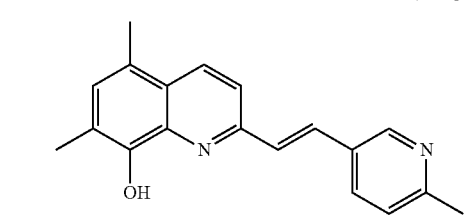

(E)-2-(2-(2-aminopyridin-3-yl)vinyl)-
5,7-dimethyquinolin-8-ol (Compound #322)

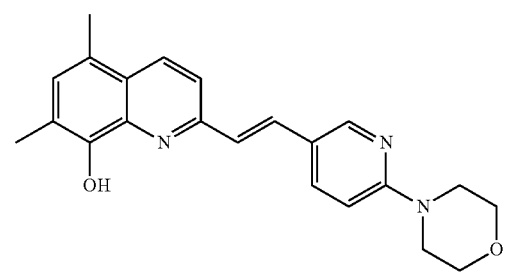

(E)-5,7-dimethyl-2-(2-(6-methylpyridin-3-
yl)vinyl)quinolin-8-ol (Compound #323)

(E)-5,7-dimethyl-2-(2-(6-
morpholinopyridin-3-yl)vinyl)quinolin-8-ol (Compound #324)

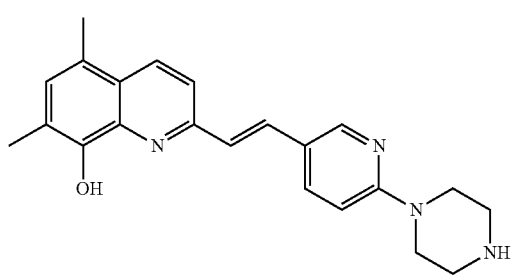

(E)-5,7-dimethyl-2-(2-(6-(piperazin-1-
yl)pyridin-3-yl)vinyl)quinolin-8-ol

-continued

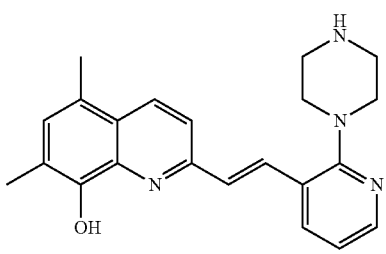

(Compound #325)

(E)-5,7-dimethyl-2-(2-(2-(piperazin-1-yl)pyridin-3-yl)vinyl)quinolin-8-ol

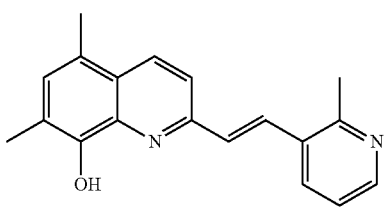

(Compound #326)

(E)-5,7-dimethyl-2-(2-(2-(methylpyridin-3-yl)vinyl)quinolin-8-ol or a pharmaceutically acceptable salt, hydrate or solvate thereof.

9. The compound as claimed in claim 8, wherein the compound is:

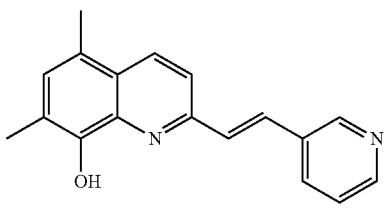

(Compound #249)

(E)-5,7-dimethyl-2-(2-(pyridin-3-yl)vinyl)quinolin-8-ol or a pharmaceutically acceptable salt, hydrate or solvate thereof.

10. A process for preparing a compound of formula Ib as defined in claim 1, the process comprising the steps of:

reacting a compound of formula A:

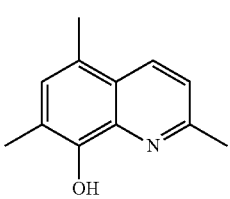

Formula A with a compound of formula B:

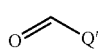

Formula B to form a compound of formula Ib':

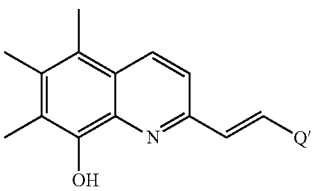

Formula Ib' wherein either:
a) Q' has the meanings defined in claim 1 in relation to the Q group of Formula Ib such that the compound of Formula Ib' is a compound of Formula Ib; or
b) Q' is a precursor to the corresponding Q group in formula Ib as defined in claim 1, in which case said compound of Formula Ib' is thereafter transformed into the compound of Formula Ib by further reaction to convert any such precursor groups into a group Q of Formula Ib;

and optionally thereafter:
(i) transforming the compound of Formula Ib into another compound of Formula Ib;
(ii) removing any protecting groups present;
(iii) forming a pharmaceutically acceptable salt, hydrate or solvate thereof; and/or
(iv) forming a prodrug thereof.

11. A pharmaceutical composition comprising a compound of Formula Ib:

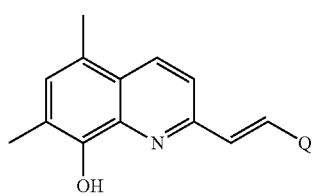

Formula Ib wherein:
Q is a ring system selected from a 5- or 6-membered heteroaryl, or (5-7C)cycloalkyl, each of which is optionally fused to a 5- or 6-membered heterocyclyl ring, and wherein the Q ring system is optionally substituted by: one, two, or three $R_Q$ groups; wherein $R_Q$ is independently selected from halo, hydroxy, nitro, cyano, (1-4C)alkyl, (1-4C)haloalkyl, (1-4C)alkoxy, (1-4C)haloalkoxy, $NR_cR_c$, $C(O)R_c$, $C(O)OR_c$, $OC(O)R_c$, $C(O)N(R_d)R_c$, $N(R_c)C(O)R_d$, $S(O)_pR_c$ (where p is 0, 1 or 2), $SO_2N(R_c)R_d$, $N(R_c)SO_2R_d$, or a 4-, 5-, 6-membered heterocyclyl, wherein $R_c$ and $R_d$ are each independently selected from H or (1-4C)alkyl;

or a pharmaceutically acceptable salt, hydrate or solvate thereof, in admixture with a pharmaceutically acceptable diluent or carrier.

12. A method of inhibiting the formation of amyloid deposits, comprising administering the pharmaceutical composition as claimed in claim 11.

13. A method of inhibiting apoptotic or excitotoxic cell-death, comprising administering the pharmaceutical composition as claimed in claim 11.

\* \* \* \* \*

UNITED STATES PATENT AND TRADEMARK OFFICE
CERTIFICATE OF CORRECTION

PATENT NO.      : 9,822,078 B2
APPLICATION NO. : 15/121973
DATED           : November 21, 2017
INVENTOR(S)     : David Vaux et al.

Page 1 of 13

It is certified that error appears in the above-identified patent and that said Letters Patent is hereby corrected as shown below:

In the Claims

Column 56, Line 50, to Column 63, Line 25:

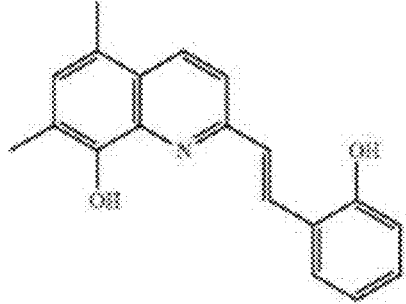

(Compound #214)

(E)-2-(2-hydroxystyryl)-5,7-dimethylquinolin-8-ol

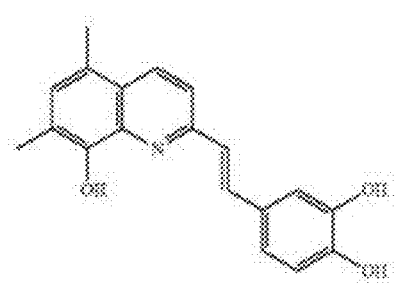

(Compound #231)

"   (E)-4-(2-(8-hydroxy-5,7-dimethylquinolin-2-yl)vinyl)benzene-1,2-diol

Signed and Sealed this
Twenty-second Day of May, 2018

Andrei Iancu
*Director of the United States Patent and Trademark Office*

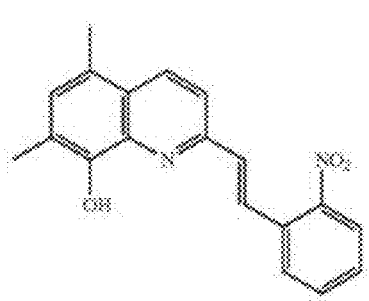
(Compound #223)
(E)-5,7-dimethyl-2-(2-nitrostyryl)quinolin-8-ol
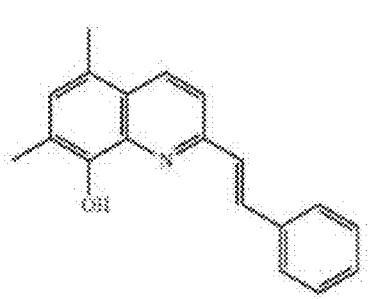
(Compound #225)
(E)-5,7-dimethyl-2-styrylquinolin-8-ol
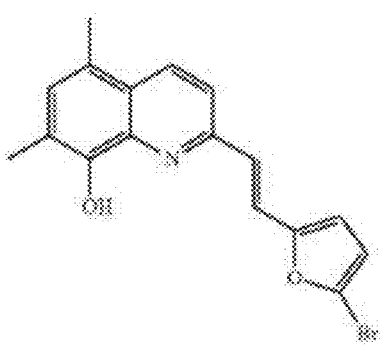
(Compound #226)
(E)-2-(2-(5-bromofuran-2-yl)vinyl)-5,7-dimethylquinolin-8-ol
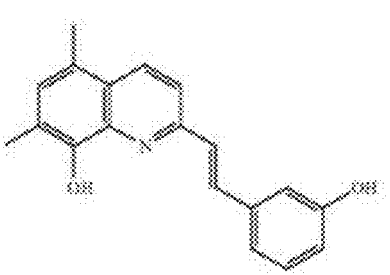
(Compound #227)
(E)-2-(3-hydroxystyryl)-5,7-dimethylquinolin-8-ol

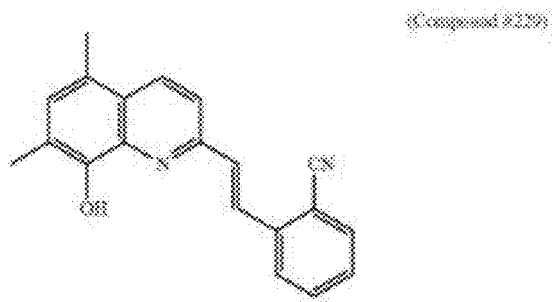
(Compound #229)
(E)-2-(2-(8-hydroxy-5,7-dimethylquinolin-2-yl)vinyl)benzonitrile
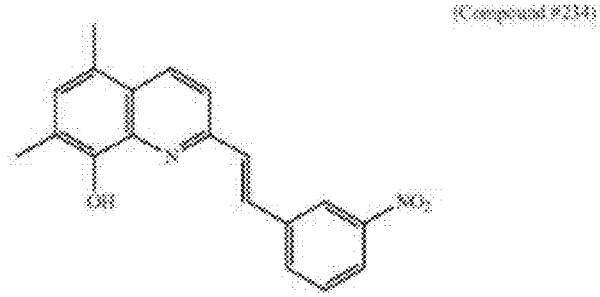
(Compound #234)
(E)-5,7-dimethyl-2-(3-nitrostyryl)quinolin-8-ol
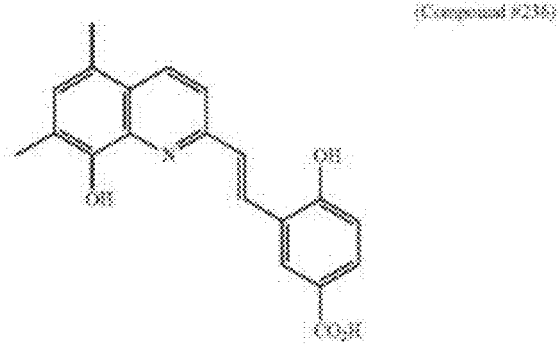
(Compound #236)
(E)-4-hydroxy-3-(2-(8-hydroxy-5,7-dimethylquinolin-2-yl)vinyl)benzoic acid
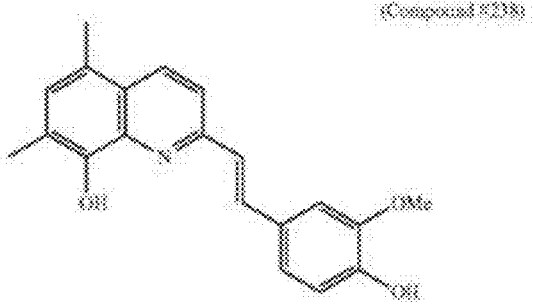
(Compound #238)
(E)-2-(4-hydroxy-3-methoxystyryl)-5,7-dimethylquinolin-8-ol

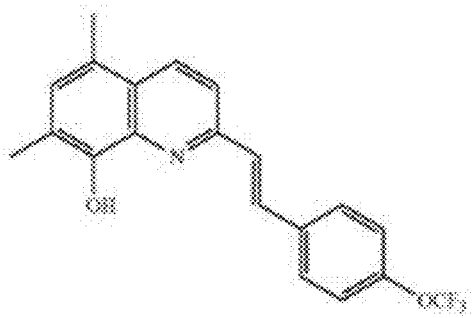
(Compound #239)
(E)-5,7-dimethyl-2-(4-(trifluoromethoxy)styryl)quinolin-8-ol
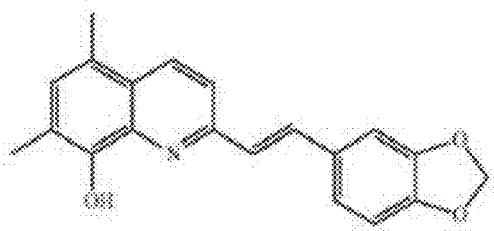
(Compound #241)
(E)-2-(2-(benzo[d][1,3]dioxol-5-yl)vinyl)-5,7-dimethylquinolin-8-ol
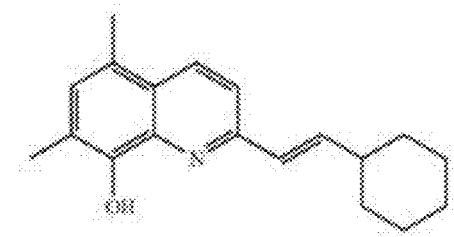
(Compound #245)
(E)-2-(2-cyclohexylvinyl)-5,7-dimethylquinolin-8-ol
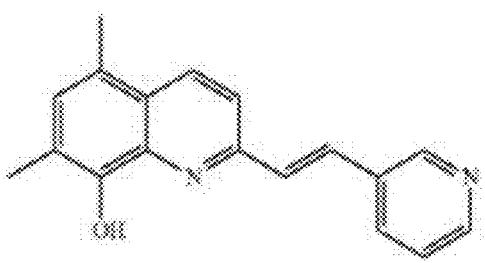
(Compound #249)
(E)-5,7-dimethyl-2-(2-(pyridin-3-yl)vinyl)quinolin-8-ol

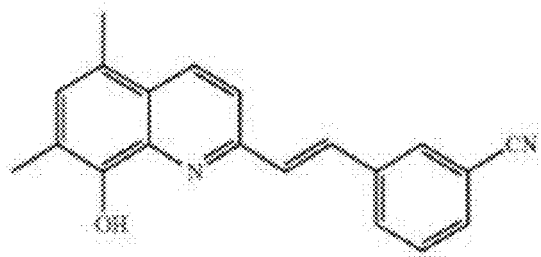
(Compound #281)
(E)-3-(2-(8-hydroxy-5,7-dimethylquinolin-2-yl)vinyl)benzonitrile
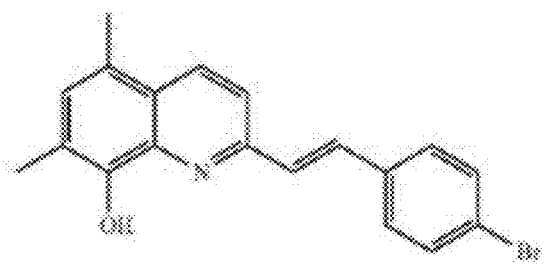
(Compound #282)
(E)-2-(4-bromostyryl)-5,7-dimethylquinolin-8-ol
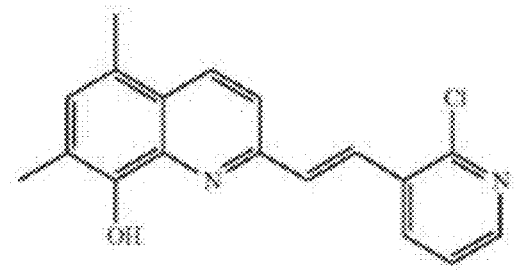
(Compound #311)
(E)-2-(2-(2-chloropyridin-3-yl)vinyl)-5,7-dimethylquinolin-8-ol
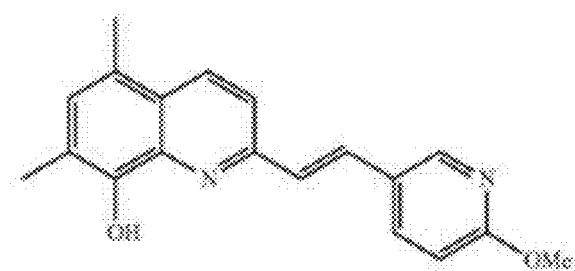
(Compound #312)
(E)-2-(2-(6-methoxypyridin-3-yl)vinyl)-5,7-dimethylquinolin-8-ol

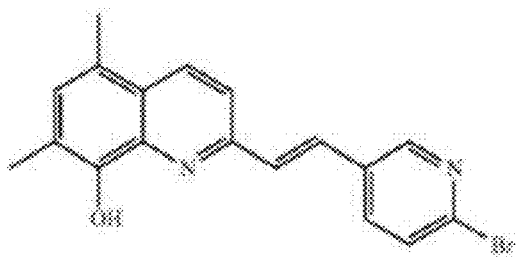
(Compound #313)
(E)-2-(2-(6-bromopyridin-3-yl)vinyl)-5,7-dimethylquinolin-8-ol
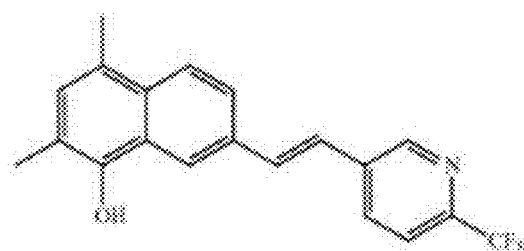
(Compound #314)
(E)-5,7-dimethyl-2-(2-(6-(trifluoromethyl)pyridin-3-yl)vinyl)quinolin-8-ol
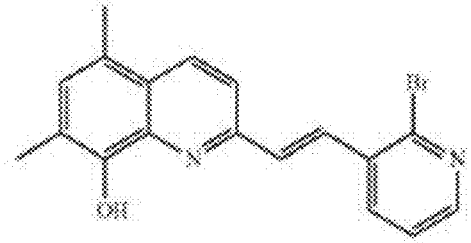
(Compound #315)
(E)-2-(2-(2-bromopyridin-3-yl)vinyl)-5,7-dimethylquinolin-8-ol
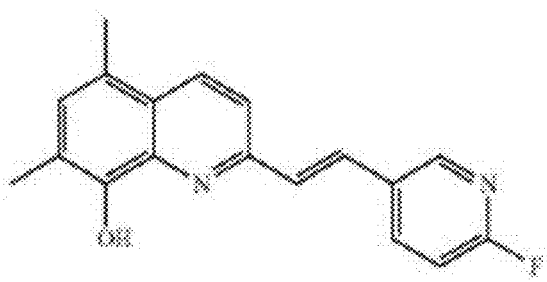
(Compound #316)
(E)-2-(2-(6-fluoropyridin-3-yl)vinyl)-5,7-dimethylquinolin-8-ol

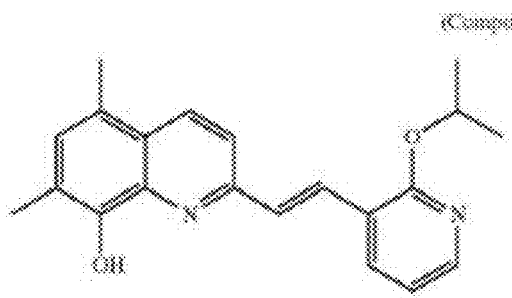
(Compound #317)
(E)-2-(2-(2-isopropoxypyridin-3-yl)vinyl)-5,7-dimethylquinolin-8-ol
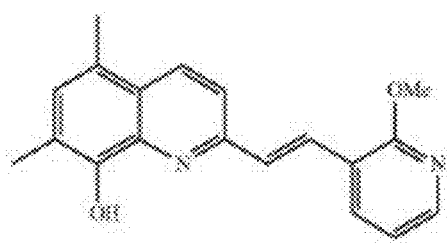
(Compound #318)
(E)-2-(2-(2-methoxypyridin-3-yl)vinyl)-5,7-dimethylquinolin-8-ol
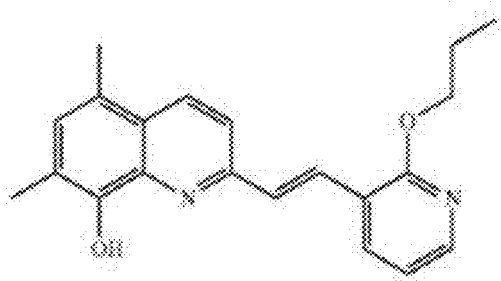
(Compound #319)
(E)-5,7-dimethyl-2-(2-(2-propoxypyridin-3-yl)vinyl)quinolin-8-ol
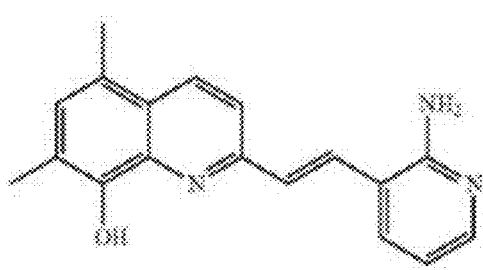
(Compound #321)
(E)-2-(2-(2-aminopyridin-3-yl)vinyl)-5,7-dimethylquinolin-8-ol

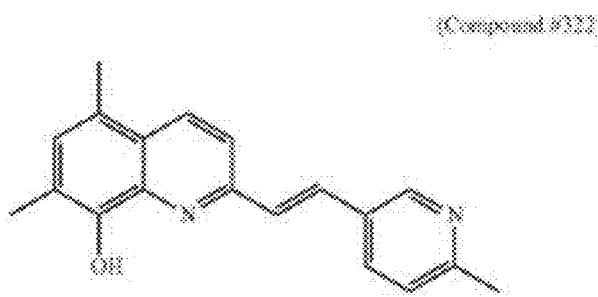
(Compound #332)
(E)-5,7-dimethyl-2-(2-(6-methylpyridin-3-yl)vinyl)quinolin-8-ol
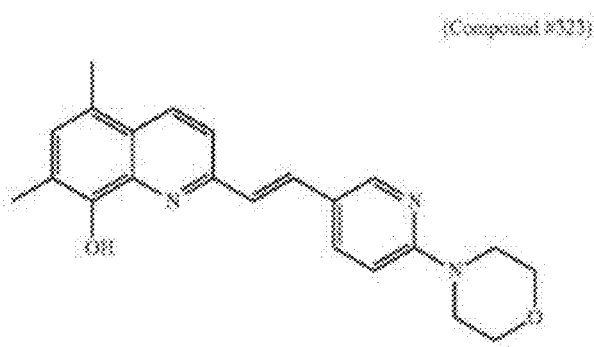
(Compound #333)
(E)-5,7-dimethyl-2-(2-(6-morpholinopyridin-3-yl)vinyl)quinolin-8-ol
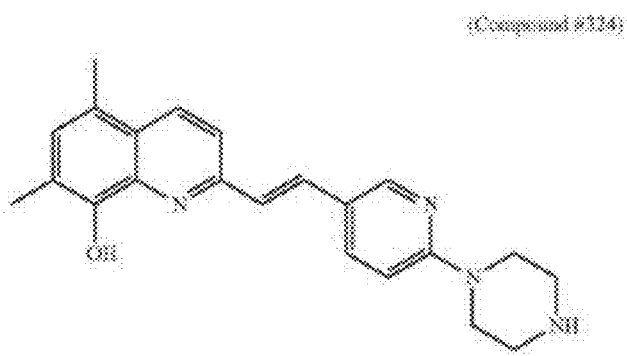
(Compound #334)
(E)-5,7-dimethyl-2-(2-(6-(piperazin-1-yl)pyridin-3-yl)vinyl)quinolin-8-ol
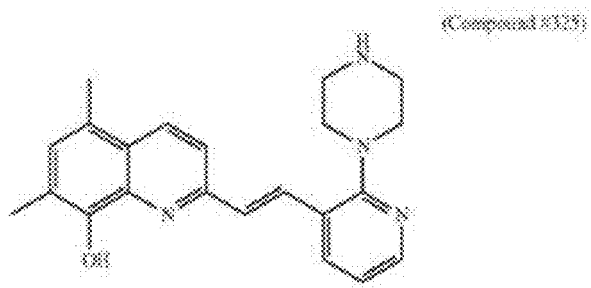
(Compound #335)
(E)-5,7-dimethyl-2-(2-(2-(piperazin-1-yl)pyridin-3-yl)vinyl)quinolin-8-ol

CERTIFICATE OF CORRECTION (continued)
U.S. Pat. No. 9,822,078 B2

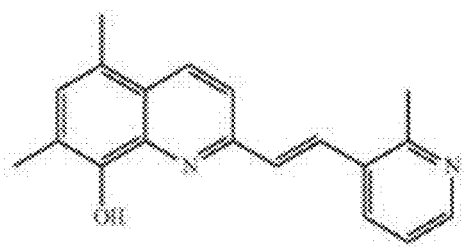

Should read:

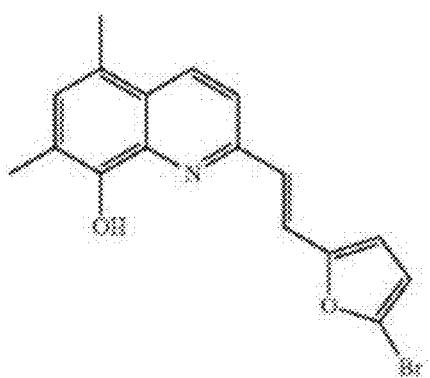

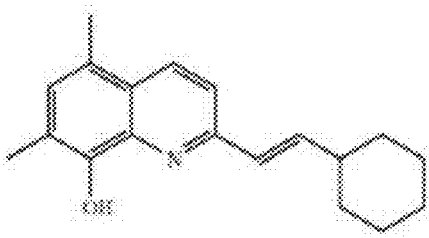

--

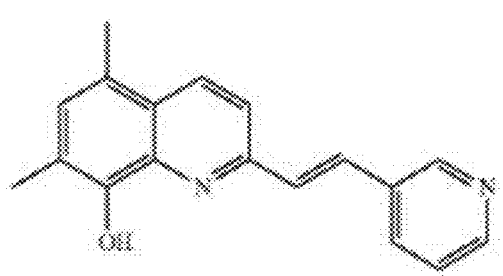
(Compound #249)
(E)-5,7-dimethyl-2-(2-(pyridin-3-yl)vinyl)quinolin-8-ol
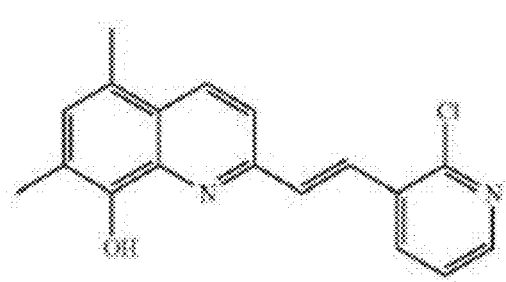
(Compound #311)
(E)-2-(2-(2-chloropyridin-3-yl)vinyl)-5,7-dimethylquinolin-8-ol
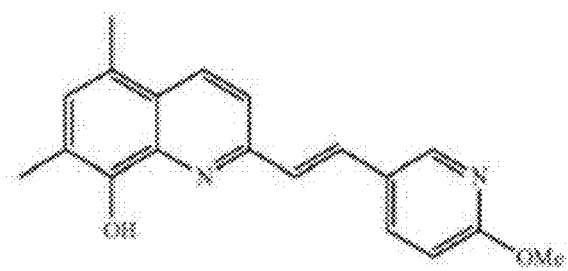
(Compound #312)
(E)-2-(2-(6-methoxypyridin-3-yl)vinyl)-5,7-dimethylquinolin-8-ol
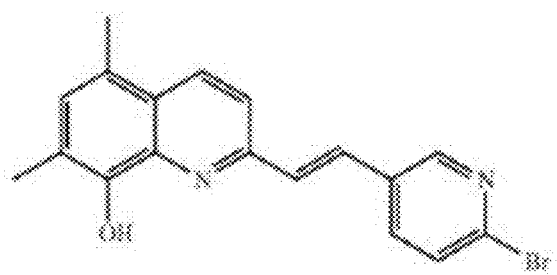
(Compound #313)
(E)-2-(2-(6-bromopyridin-3-yl)vinyl)-5,7-dimethylquinolin-8-ol

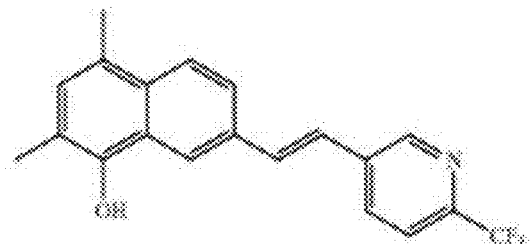
(Compound #314)
(E)-5,7-dimethyl-2-(2-(6-trifluoromethyl)pyridin-3-yl)vinyl)quinolin-8-ol
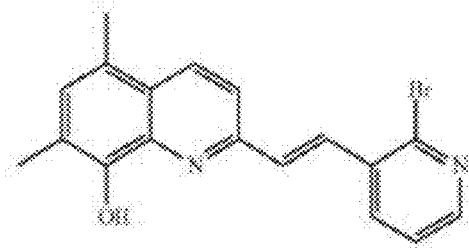
(Compound #315)
(E)-2-(2-(2-bromopyridin-3-yl)vinyl)-5,7-dimethylquinolin-8-ol
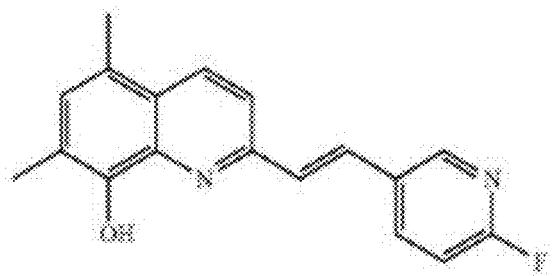
(Compound #316)
(E)-2-(2-(6-fluoropyridin-3-yl)vinyl)-5,7-dimethylquinolin-8-ol
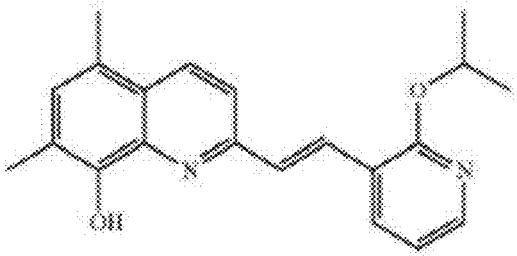
(Compound #317)
(E)-2-(2-(2-isopropoxypyridin-3-yl)vinyl)-5,7-dimethylquinolin-8-ol

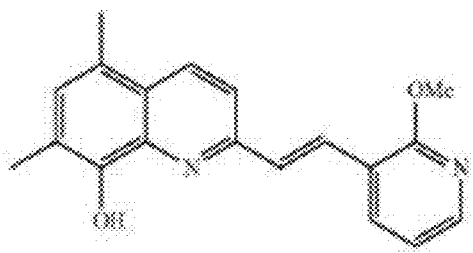
(Compound #318)
(E)-2-(2-(2-methoxypyridin-3-yl)vinyl)-5,7-dimethylquinolin-8-ol
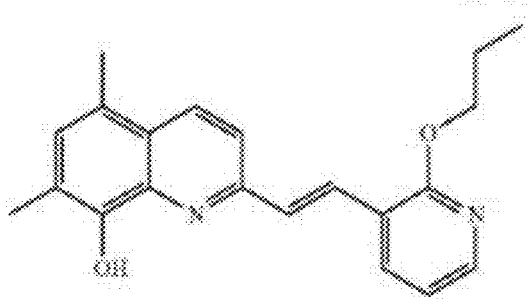
(Compound #319)
(E)-5,7-dimethyl-2-(2-(2-propoxypyridin-3-yl)vinyl)quinolin-8-ol
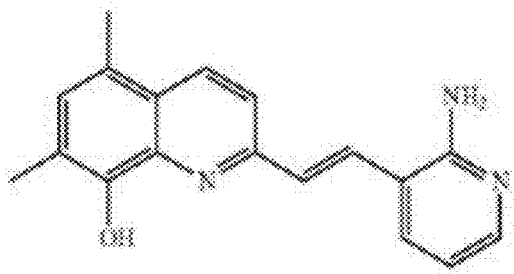
(Compound #321)
(E)-2-(2-(2-aminopyridin-3-yl)vinyl)-5,7-dimethylquinolin-8-ol
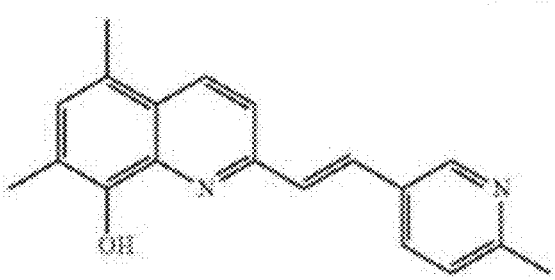
(Compound #322)
(E)-5,7-dimethyl-2-(2-(6-methylpyridin-3-yl)vinyl)quinolin-8-ol

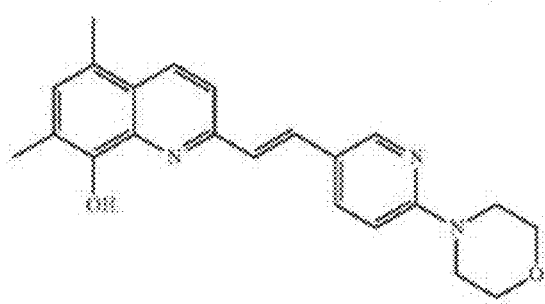
(Compound #323)
(E)-5,7-dimethyl-2-(2-(6-morpholinopyridin-3-yl)vinyl)quinolin-8-ol
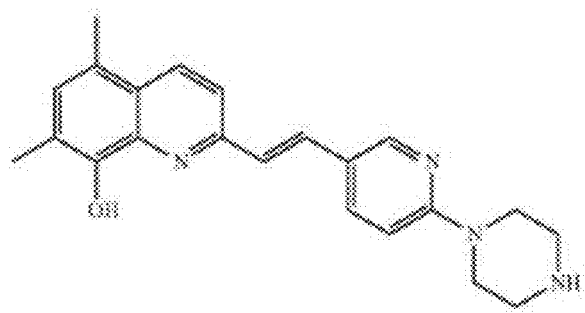
(Compound #324)
(E)-5,7-dimethyl-2-(2-(6-(piperazin-1-yl)pyridin-3-yl)vinyl)quinolin-8-ol
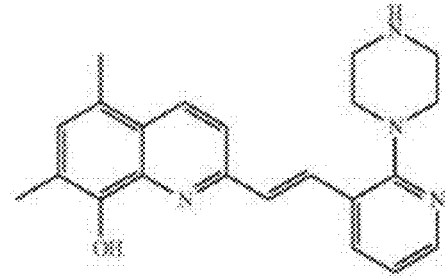
(Compound #325)
(E)-5,7-dimethyl-2-(2-(2-(piperazin-1-yl)pyridin-3-yl)vinyl)quinolin-8-ol
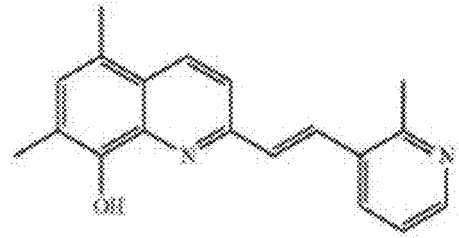
(Compound #326)
(E)-5,7-dimethyl-2-(2-(2-methylpyridin-3-yl)vinyl)quinolin-8-ol